United States Patent
Toczko et al.

(10) Patent No.: US 12,134,619 B2
(45) Date of Patent: Nov. 5, 2024

(54) CRYSTALLINE SALTS OR CO-CRYSTALS OF 2',6-DIFLUORO-5'-[3-(1-HYDROXY-1-METHYLETHYL)-IMIDAZO[1,2-B][1,2,4]TRIAZIN-7-YL]BIPHENYL-2-CARBONITRILE WITH P-TOLUENESULOFONIC ACID AS GABAA POSITIVE ALLOSTERIC MODULATORS

(71) Applicant: NeuroCycle Therapeutics, Inc., San Diego, CA (US)

(72) Inventors: Matthew Toczko, Raleight, NC (US); Jed Hubbs, Cambridge, MA (US)

(73) Assignee: NEUROCYCLE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 18/089,661

(22) Filed: Dec. 28, 2022

(65) Prior Publication Data
US 2023/0139418 A1   May 4, 2023

Related U.S. Application Data

(60) Division of application No. 17/072,282, filed on Oct. 16, 2020, now Pat. No. 11,542,263, which is a continuation of application No. PCT/US2019/027880, filed on Apr. 17, 2019.

(60) Provisional application No. 62/659,226, filed on Apr. 18, 2018.

(51) Int. Cl.
A61K 31/53     (2006.01)
C07D 487/04    (2006.01)

(52) U.S. Cl.
CPC ........ *C07D 487/04* (2013.01); *C07B 2200/13* (2013.01)

(58) Field of Classification Search
CPC .............................. A61K 31/53; C07D 487/04
USPC .......................................... 514/243; 544/184
See application file for complete search history.

(56) References Cited

U.S. PATENT DOCUMENTS

| 6,630,471 B1   | 10/2003 | Carling et al.   |
|----------------|---------|------------------|
| 2011/0082147 A1| 4/2011  | Harbeson et al.  |
| 2011/0195950 A1| 8/2011  | Hintermann et al.|
| 2017/0258800 A1| 9/2017  | Weng et al.      |

FOREIGN PATENT DOCUMENTS

| CL | 200901250   | 5/2009  |
|----|-------------|---------|
| EA | 0003332     | 4/2003  |
| EP | 2960234     | 12/2015 |
| JP | 2002-518501 | 1/1976  |
| JP | 2011-520976 | 7/1977  |
| JP | 2004-523584 | 8/1985  |
| JP | 2004170323  | 6/2004  |
| JP | 2004-536862 | 12/2004 |
| WO | 2002/074773 | 9/2002  |
| WO | 03/008418   | 1/2003  |
| WO | 2011/011712 | 1/2011  |
| WO | 2015/072853 | 5/2015  |
| WO | 2017/129801 | 8/2017  |
| WO | WO-2019204446 A1 * | 10/2019 | ............. A61K 31/53 |

OTHER PUBLICATIONS

Jordan, V. C. Nature Reviews: Drug Discovery, 2, 2003, 205.*
Hackam, et al. JAMA, 296(14), 2006, 1731-1732.*
Russian Office Action dated Apr. 10, 2023 for App. No. 2020134403/04(063141) (27 pages).
Richard J. Bastin et al., "Salt selection and Optimisation Procedures for Pharmaceutical New Chemical Entities", Organic Process Research & Development, 2000, vol. 4, pp. 427-435 (abstract, Table 1).
Ranjit Thakuria et al., "Pharmaceutical cocrystals and poorly soluble drugs", International Journal of Pharmaceutics, 2013, vol. 453(1), 101-125 (full document, in particular, sections 1, 4-5, 7(7.1-7.2), Fig. 17)); doi: 10.1016/j.ijpharm.2012.10.043.
A. V. Yadav et al., "Co-crystals: A novel approach to modify physicochemical properties of active pharmaceutical ingredients", Indian Journal of Pharmaceutical Science, 2009, Jul.-Aug., pp. 359-370 (see full document, in particular, "Advantages of co-crystals", p. 361 to p. 363; doi: 10.4103/0250-474X.57283).
Naga K. Duggirala et al., "Pharmaceutical cocrystals: along the path to improved medicines", Chem. Commun., 2016, vol. 52, pp. 640-655 (p. 649 bottom paragraph 2 to p. 652); doi: 10.1039/c5cc08216a).
Mino R. Caira, "Crystalline Polymorphism of Organic Compounds", Topics in Current Chemistry, 1998, vol. 198, pp. 163-208 (pp. 64-166, section 3.1).

(Continued)

*Primary Examiner* — Douglas M Willis
(74) *Attorney, Agent, or Firm* — K&L Gates LLP

(57) ABSTRACT

Described herein are polymorphs comprising 2',6-difluoro-5'-[3-(1-hydroxy-1-methylethyl)-imidazo[1,2-b][1,2,4]triazin-7-yl]biphenyl-2-carbonitrile (TPA023B) or salts thereof. In one aspect, disclosed herein is a crystalline polymorphic salt or co-crystal of TPA023B with p-toluenesulfonic acid of the following formula:

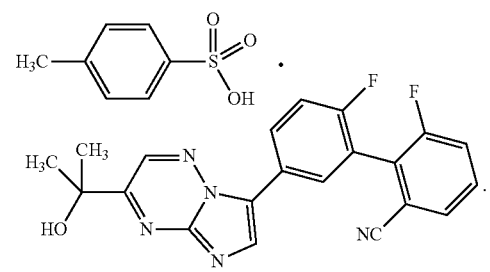

Also described herein are methods of making and using the same.

21 Claims, 35 Drawing Sheets

(56) References Cited

OTHER PUBLICATIONS

Sherry L. Morissette et al., "High-through put crystallization: polymorphs, salts, co-crystals and solvates of pharmaceutical solids", Advanced Drug Delivery Reviews, 2004, vol. 56, pp. 275-300, section 1, 3.1, 3.5; doi:10.1016/j.addr.2003.10.020.
Office Action for Japanese App. No. 2021-506619 dated Apr. 19, 2023 (8 pages with translation).
Organic Process Research & Development, Polymorphism in Processes of Crystallization in Solution: A Practical Review; Mangin et al.; 2009, vol. 13, No. 6, pp. 1241-1253 (document showing well known art).
Hirayama, Noriaki, Yuuki kagoubutsu kesshou sakusei handobukku, 2008, pp. 17-23, 37-40, 45-51, 57-65(document showing well known art).
The Chemical Society of Japan, Kagakubinran Ouyou-kagaku Hen, 6th ed., Chapter 4 Chemical Synthesis Technology, Maruzen, Jan. 30, 2003, p. 178 (document showing well known art).
Ashizawa, Kazuhide, Optimization and Crystalization Technology of Salt and Crystal Forms, Physico-Chemical Studies on the Molecular Details of Drug Crystals; Pharm Tech Japan, 2002, vol. 18, No. 10, pp. 81-96 (document showing well known art).
Takada, Noriyuki, Bulk Drug Form Screening and Selection in Drug Development Stage, M STAGE, API form screening in drug discovery stage; vol. 6, No. 10, Jan. 15, 2007, pp. 20-25(document showing well known art).
Brazil Office Action for App. No. BR112020021104-4 dated Mar. 15, 2023 (4 pages).
European Examination Report for App. No. 19 788 410.9-1110 dated May 5, 2023 (5 pages).
Taiwan Office Action for Application No. 108113441 dated Apr. 12, 2023 (11 pages).
Office Action for Russian App. No. 2018128905 dated May 5, 2021 (28 pages with translation).
Thomsen, J. S. et al.: Suppression of Spontaneous Scratching in Hairless Rats by Sedatives but Not by Antipruritics, Skin Pharmacology and Physiology, 15 (4), 2002, pp. 218-224 (doi: 10.1159 000065968) (abstract, p. 222, fig. 2).
Jh Xu et al.: "An animal model for screening of antiallergic and antipruritic drugs", Jan. 1, 1996, retrieved from the Internet https://www.ncbi.nlm.nih.gov/pubmed/9275721 (abstract).
Da Settimo, F., et al. "GABAA/Bz Receptor Subtypes as Targets for Selective Drugs" Current Medicinal Chemistry, 14 (25), 2007, pp. 2680-2701, doi: 10.2174 / 0929867707782023190 (entire document, especially Fig. 7, 9, 10, 11, 20, 29).
Russell, M. G. N., et al.: "Discovery of Imidazo[1, 2-b] [1, 2,4]triazines as GABAA a2/3 Subtype Selective Agonists for the Treatment of Anxiety", Journal of Medicinal Chemistry, 49 (4), 2006, p. 1235-1238, doi: 10.1021/jm051200u (entire document, especially compounds 10 12 in table. 1, Scheme 2).
Gauthier et.al. Palladium-Catalyzed Regioselective Arylation of Imidazo[1,3-b][1,2,4]triazine: Synthesis of an alpha 2/3-selective GABA Agonist in Journal of Organic Chemistry, 2005, vol. 70, pp. 5938-5945. abstract; p. 5944, col. 2, para 3.
International Committee on Harmonization et.al. Guidance for Industry Q1A(R2) Stability testing of New Drug Substances and Products, Nov. 2003, pp. 1-25. pg. 5, Table.
Chile Office Action dated Apr. 5, 2022 for App. No. 202002663 (3 pages).
India Office Action for App. No. 202017048259 dated Apr. 29, 2022 (5 pages).
Search Report for European App. No. 19788410.9 dated Jan. 4, 2022 (14 pages).
Singapore Search Report for App. No. 11202010220Q dated Mar. 8, 2022 (11 pages).
European Search Report for App. No. 19788410.9 dated May 23, 2022 (13 pages).
European Search Report for App. No. 19788410.9 dated May 10, 2022 (13 pages).
Mexican Office Action for Application No. MX/a/2020/010878 dated Apr. 25, 2023 (10 pages).
Japanese Office Action for App. No. 2021-506619 dated Sep. 27, 2023 (18 pages).
Mexican Office Action for Application No. MX/a/2020/010878 dated Jul. 10, 2023 (6 pages).
Ukranian Office Action for App. No. 2020 06722 mailed Jun. 9, 2023 with translation (5 pages).
Chinese Office Action for App. No. 201980041321.7 dated Jul. 11, 2023 (9 pages).
Chinese Office Action for App. No. 201980041321.7 mailed Nov. 30, 2023 with translation 17 pages).

\* cited by examiner

CRYSTALLINE SALTS OR CO-CRYSTALS OF 2',6-DIFLUORO-5'-[3-(1-HYDROXY-1-METHYLETHYL)-IMIDAZO[1,2-B][1,2,4]TRIAZIN-7-YL]BIPHENYL-2-CARBONITRILE WITH P-TOLUENESULOFONIC ACID AS GABAA POSITIVE ALLOSTERIC MODULATORS

CROSS-REFERENCE

This application is a divisional of U.S. application Ser. No. 17/072,282, filed Oct. 16, 2020 which is a continuation of International Application No. PCT/US2019/27880, filed Apr. 17, 2019, which claims priority to U.S. Provisional Application No. 62/659,226, filed Apr. 18, 2018, each of which is hereby incorporated by reference in its entirety.

SUMMARY OF THE INVENTION

The present disclosure generally pertains to salts and polymorphs of 2',6-difluoro-5'-[3-(1-hydroxy-1-methylethyl)-imidazo[1,2-b][1,2,4]triazin-7-yl]biphenyl-2-carbonitrile (designated herein as TPA023B), including but not limited to stable polymorphs of the salt of TPA023B with phosphoric acid:

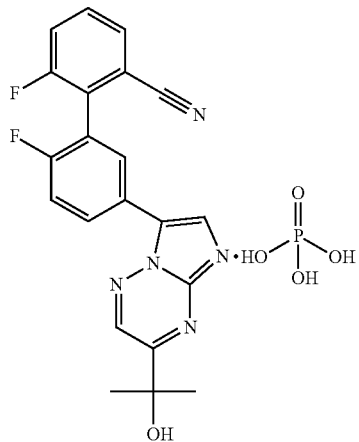

MW: 489.37 g·mol⁻¹
MF: $C_{21}H_{15}F_2N_5O \cdot H_3PO_4$

Polymorphs of the free base compound are also described. These polymorphs are suitable for use as the active pharmaceutical ingredient of products intended for therapeutic use in either humans or animals, and also as chemical intermediates in the synthesis of active pharmaceutical ingredients.

In one aspect, disclosed herein is a crystalline salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid, wherein the crystalline salt or co-crystal has at least one of the following properties: (a) an X-ray powder diffraction (XRPD) pattern substantially the same as shown in FIG. 19, when measured using the parameters described in Table 1; (b) an XRPD pattern substantially the same as shown in FIG. 1, when measured using the parameters described in Table 1; (c) an XRPD pattern having characteristic peak locations of at least three values selected from the group consisting of: about 6.4, 7.5, 10.2, 12.7, 13.3, 14.5, 16.0, 17.1, 17.4, 17.9, 18.5, 19.1, 19.7, 20.3, 20.9, 21.5, 22.6, 23.7, 26.2, 26.7, 26.9, 27.5, 28.4, 30.2, and 32.1±0.2 degrees, 2-theta, when measured using the parameters described in Table 1; (d) an XRPD pattern having characteristic peak locations of at least three values selected from the group consisting of: about 6.4, 7.5, 12.7, 13.3, 17.1, 17.4, 18.5, 19.1, 19.7, 26.7, 30.2, and 32.1±0.2 degrees, 2-Theta, when measured using the parameters described in Table 1; (e) a differential scanning calorimetry (DSC) thermogram substantially the same as shown in FIG. 2A; (f) a DSC thermogram with an endothermic peak at about 205° C.; (g) stable for at least a week at about 40° C.; and (h) stable for at least a week at about 25° C. In some embodiments, the crystalline salt or co-crystal provides an XRPD pattern substantially the same as shown in FIG. 19, when measured using the parameters described in Table 1. In some embodiments, the crystalline salt or co-crystal provides an XRPD pattern substantially the same as shown in FIG. 1, when measured using the parameters described in Table 1. In some embodiments, the crystalline salt or co-crystal provides an XRPD pattern having characteristic peak locations of at least three values selected from the group consisting of: about 6.4, 7.5, 10.2, 12.7, 13.3, 14.5, 16.0, 17.1, 17.4, 17.9, 18.5, 19.1, 19.7, 20.3, 20.9, 21.5, 22.6, 23.7, 26.2, 26.7, 26.9, 27.5, 28.4, 30.2, and 32.1±0.2 degrees, 2-theta, when measured using the parameters described in Table 1. In some embodiments, the crystalline salt or co-crystal provides an XRPD pattern having characteristic peak locations of at least six values selected from the group consisting of: about 6.4, 7.5, 10.2, 12.7, 13.3, 14.5, 16.0, 17.1, 17.4, 17.9, 18.5, 19.1, 19.7, 20.3, 20.9, 21.5, 22.6, 23.7, 26.2, 26.7, 26.9, 27.5, 28.4, 30.2, and 32.1±0.2 degrees, 2-theta, when measured using the parameters described in Table 1. In some embodiments, the crystalline salt or co-crystal provides an XRPD pattern having characteristic peak locations of at least three values selected from the group consisting of: about 6.4, 7.5, 12.7, 13.3, 17.1, 17.4, 18.5, 19.1, 19.7, 26.7, 30.2, and 32.1±0.2 degrees, 2-Theta, when measured using the parameters described in Table 1. In some embodiments, the crystalline salt or co-crystal provides a DSC thermogram substantially the same as shown in FIG. 2A. In some embodiments, the crystalline salt or co-crystal provides a DSC thermogram with an endothermic peak at about 205° C. In some embodiments, the crystalline salt or co-crystal is stable for at least a month at about 40° C. In some embodiments, the crystalline salt or co-crystal is stable for at least a month at about 25° C. In some embodiments, the crystalline salt or co-crystal provides substantially the same XRPD pattern post-storage at 40° C. and 75% RH for at least a week. In some embodiments, the crystalline salt or co-crystal provides substantially the same XRPD pattern post-storage at 40° C. and 75% RH for at least two weeks. In some embodiments, the crystalline salt or co-crystal is a salt. In some embodiments, the crystalline salt or co-crystal is a co-crystal.

In another aspect, disclosed herein is a crystalline polymorph of 2',6-difluoro-5'-[3-(1-hydroxy-1-methylethyl)-imidazo[1,2-b][1,2,4]triazin-7-yl]biphenyl-2-carbonitrile, of Form C, providing an X-ray Powder Diffraction (XRPD) pattern having characteristic peak locations of at least three values selected from the group consisting of about: 5.4, 10.8, 12.3, 12.6, 13.5, 14.8, 15.9, 16.3, 16.4, 17.3, 17.8, 19.3, 20.4, 21.5, 21.7, 22.7, 23.4, 24.4, 24.7, 25.0, 26.1, 26.6, 27.0, 27.2, 27.5, 28.4, 28.7, 29.0, 29.6, 30.2, and 32.3±0.2-degrees, 2-theta, when measured using the parameters described in Table 1. In some embodiments, the crystalline polymorph exhibits an XRPD pattern having characteristic peak locations of at least three values selected from the group consisting of about: 5.4, 10.8, 12.3, 12.6, 13.5, 14.8, 16.2, 17.3, 19.3, 20.4, 21.7, 22.7, 23.4, 24.4, 25.0, 27.2, 29.6, and 32.2±0.2 degrees, 2-theta, when measured using the parameters described in Table 1. In some embodiments, the crystalline polymorph provides an XRPD pattern substantially the same as an XRPD pattern labelled as Form C in FIG. 12. In some embodiments, the crystalline polymorph has a differential scanning calorimetry (DSC) thermogram comprising an endothermic peak at about 210° C. In some embodiments, the crystalline polymorph has a DSC thermogram substantially the same as shown in FIG. 13. A crystalline polymorph of 2',6-difluoro-5'-[3-(1-hydroxy-1-methylethyl)-imidazo[1,2-b][1,2,4]triazin-7-yl]biphenyl-2-carbonitrile, of Form B, providing an X-ray Powder Diffraction (XRPD) Pattern having characteristic peak locations of at least three values selected from the group consisting of about: 7.4, 7.7, 10.0, 13.2, 17.2, 20.4, and 29.9±0.2 degrees, 2-theta, when measured using the parameters described in Table 1. In some embodiments, the crystalline polymorph provides an XRPD pattern substantially the same as shown in FIG. 11. In some embodiments, the crystalline polymorph is an ethanol solvate.

In yet another aspect, disclosed herein is a crystalline salt or co-crystal of 2',6-difluoro-5'-[3-(1-hydroxy-1-methylethyl)-imidazo[1,2-b][1,2,4]triazin-7-yl]biphenyl-2-carbonitrile with toluenesulfonic acid providing an X-ray Powder Diffraction (XRPD) pattern having characteristic peak locations of at least three values selected from the group consisting of about: 7.0, 12.4, 12.6, 13.0, 14.1, 15.4, 15.7, 16.3, 17.5, 18.3, 19.0, 21.0, 22.3, 23.0, and 24.9±0.2 degrees, 2-theta, when measured using the parameters described in Table 1. In some embodiments, the crystalline salt or co-crystal provides an XRPD pattern substantially the same as shown in FIG. 17. In some embodiments, the crystalline salt or co-crystal is a hydrate or solvate. In some embodiments, the crystalline salt or co-crystal provides a differential scanning calorimetry (DSC) thermogram comprising an endothermic peak at about 170° C. In some embodiments, the crystalline salt or co-crystal provides a DSC thermogram substantially the same as shown in FIG. 18.

In one aspect, disclosed herein is a therapeutic or prophylactic composition comprising a described compound.

In another aspect, disclosed herein is a method of treating a condition or a disorder in a subject in need thereof, the method comprising administering a therapeutically effective amount of a compound or a composition described herein to said subject. In some embodiments, the condition or disorder is associated with α2/α3 GABAA receptor. In some embodiments, the condition or disorder is selected from: pain, anxiety, epilepsies, muscle spasms, pruritus, itch, cognitive impairment, alcohol dependence, drug addition, schizophrenia, depression, autism, panic disorder, and generalized anxiety disorder. In some embodiments, the condition or disorder is pain. In some embodiments, the pain is Fibromyalgia, Inflammatory pain, Neuropathic pain, Peripheral Diabetic Neuropathy, Chemotherapy induced pain, HIV associated Neuropathy, Post-herpetic neuralgia, Musculoskeletal pain, Rheumatoid arthritis, Osteoarthritis, Postoperative pain, Burn pain, Sunburn pain, or Phantom limb pain. In some embodiments, the condition or disorder is itch. In some embodiments, the itch is Chronic Itch, Neurogenic itch, Uremic Pruritus, Neurodermatitis, Atopic Dermatitis, Prurigo Nodularis, Notalgia Parasthetica, Psoriasis, Psychogenic itch or Aquagenic Itch. In some embodiments, the condition or disorder is epilepsy. In some embodiments, the epilepsy is Focal epilepsy, Generalized epilepsy, Dravet Syndrome, Childhood absence epilepsy (CEA), Juvenile absence epilepsy, Juvenile myoclonic epilepsy (JME), West Syndrome, Lennox-Gastaut syndrome (LGS), Sunflower Syndrome, Staticus epilepticus, Nerve agent induced seizures, Tremors from alcohol withdrawal, Traumatic Brain Injury, Tuberous Sclerosis Complex, Doose Syndrome, Rasmussen's Syndrome, Early myoclonic encephalopathy, Malignant migrating partial seizures of infancy, Epilepsy with continuous spike and waves during slow wave sleep, Landau-Kleffner syndrome, Benign epilepsy with centrotemporal spikes, Benign familial neonatal infantile seizures, Cortical dysplasia focal epilepsy syndrome, Generalized epilepsy with febrile seizure plus (GEFS+), Myoclonic atonic epilepsy, Malignant migrating partial seizures of infancy, Ohtahara syndrome (a.k.a. early infantile epileptic encephalopathy), or Partial epilepsy and febrile seizures plus. In some embodiments, the condition or disorder is autism. In some embodiments, the autism is an autism resulting from SCN2a mutation, fragile X syndrome, or autism related to ion-channel dysfunction.

In one aspect, disclosed herein is a method for preparing a crystalline salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid, the method comprising crystallizing 2',6-difluoro-5'-[3-(1-hydroxy-1-methylethyl)-imidazo[1,2-b][1,2,4]triazin-7-yl]biphenyl-2-carbonitrile phosphate from a solution comprising one or more of: ethyl acetate, methyl ethyl ketone, 2-methyl butanone, dimethyl sulfoxide, dimethylformamide, dimethyl acetamide, acetone, water, tetrahydrofuran (THF), 2-methyl-THF, isopropyl acetate (IPAC), acetonitrile, and dichloromethane, wherein the crystalline salt or co-crystal provides an X-ray Powder Diffraction (XRPD) pattern having characteristic peak locations of at least three values selected from the group consisting of: about 6.4, 7.5, 10.2, 12.7, 13.3, 14.5, 16.0, 17.1, 17.4, 17.9, 18.5, 19.1, 19.7, 20.3, 20.9, 21.5, 22.6, 23.7, 26.2, 26.7, 26.9, 27.5, 28.4, 30.2, and 32.1±0.2 degrees, 2-theta, when measured using the parameters described in Table 1. In some embodiments, the crystalline salt or co-crystal provides an XRPD pattern having characteristic peak locations of at least three values selected from the group consisting of: about 6.4, 7.5, 12.7, 13.3, 17.1, 17.4, 18.5, 19.1, 19.7, 26.7, 30.2, and 32.1±0.2 degrees, 2-Theta, when measured using the parameters described in Table 1. In some embodiments, the crystalline salt or co-crystal provides an XRPD pattern substantially the same as shown in FIG. 19, when measured using the parameters described in Table 1.

BRIEF DESCRIPTION OF THE DRAWINGS

FIGS. 17A and 18B illustrate an XRPD pattern for TPA023B tosylate Form A (FIG. 17A); and an NMR spectrum of TPA023B tosylate Form A (FIG. 18B)

DETAILED DESCRIPTION

Described herein are novel free base polymorphs, pharmaceutical salts and salt polymorphs, and pharmaceutical co-crystals and co-crystal polymorphs having beneficial properties including improved solubility, improved oral bioavailability, more consistent oral bioavailability, improved stability, improved manufacturability, and corresponding improved formulations. Salts, co-crystals, polymorphs, salt polymorphs, and co-crystal polymorphs of TPA023B are described herein, and are useful for treating several disorders in addition to itch. Those skilled in the art will appreciate that such compounds may find use in treating any disorders reported to be treatable by a2/a3 GABAA positive allosteric modulators, as well as disorders treatable with non-selective GABAA positive allosteric modulators. These include, but are not limited to, pain, anxiety, epilepsies, muscle spasms, pruritus, itch, cognitive impairment, alcohol dependence, schizophrenia, depression, autism, and the like.

Phosphate

Phosphate Form A

Figure 19:
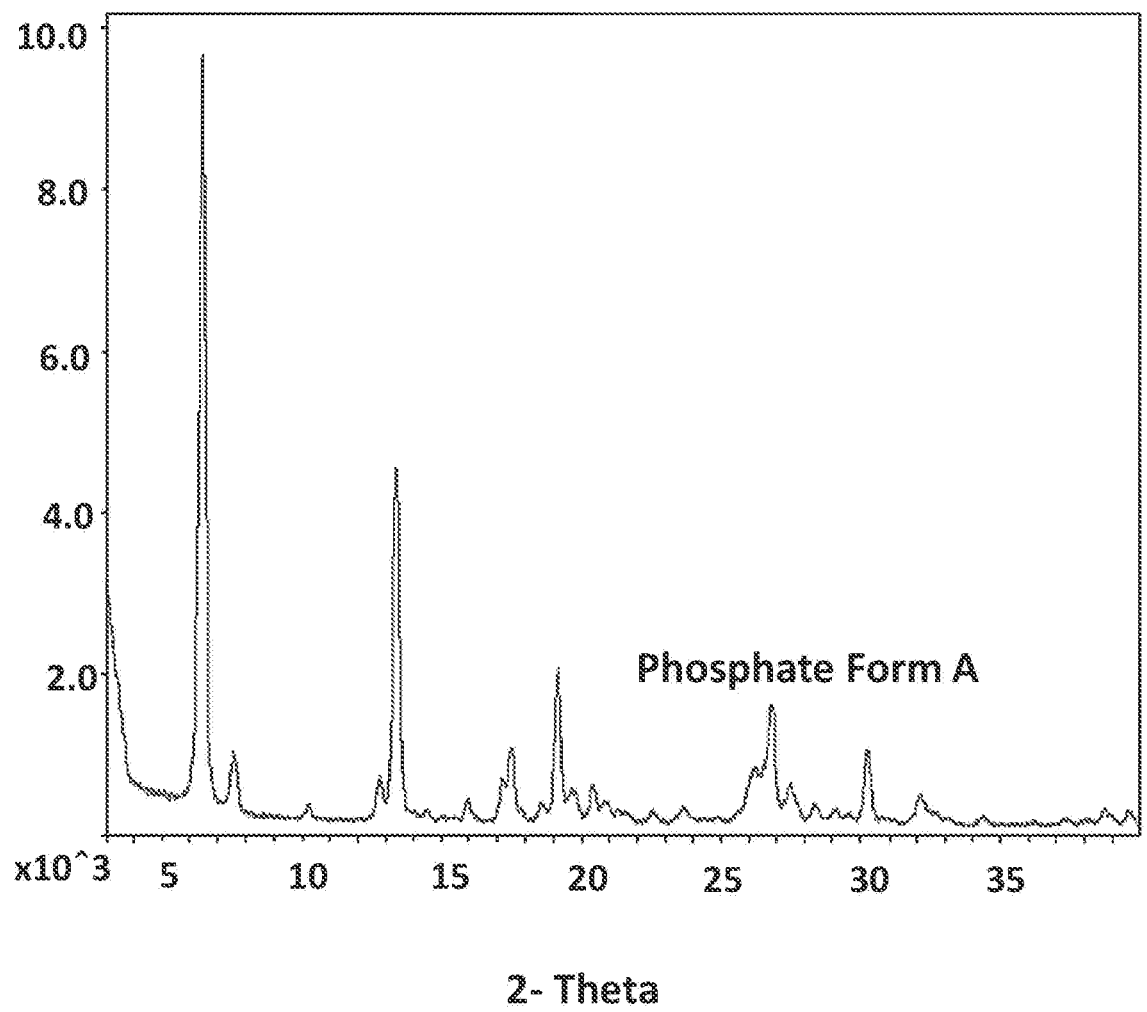
FIG. 19 illustrates an XRPD pattern for TPA023B phosphate Form A
Figure 20:
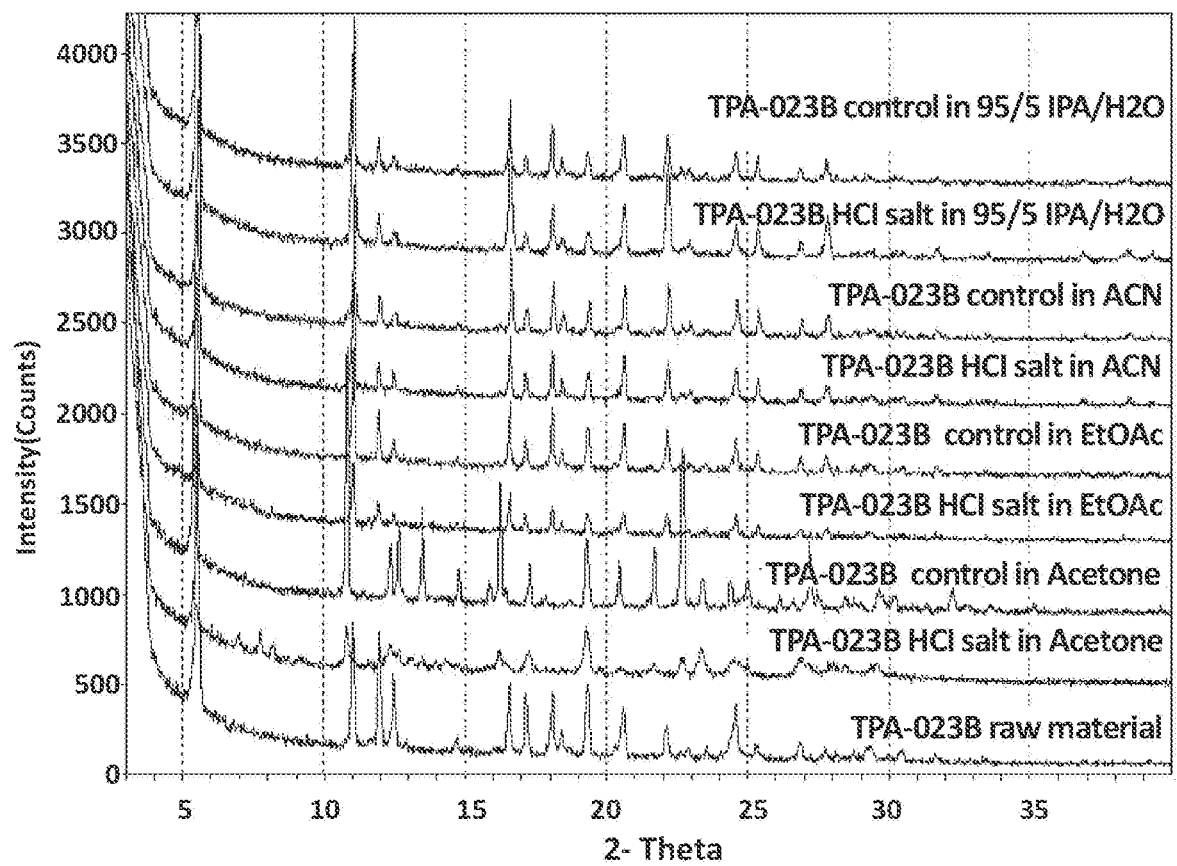
FIG. 20 illustrates XRPD patterns of TPA023B HCl Salt Screening
Figure 21:
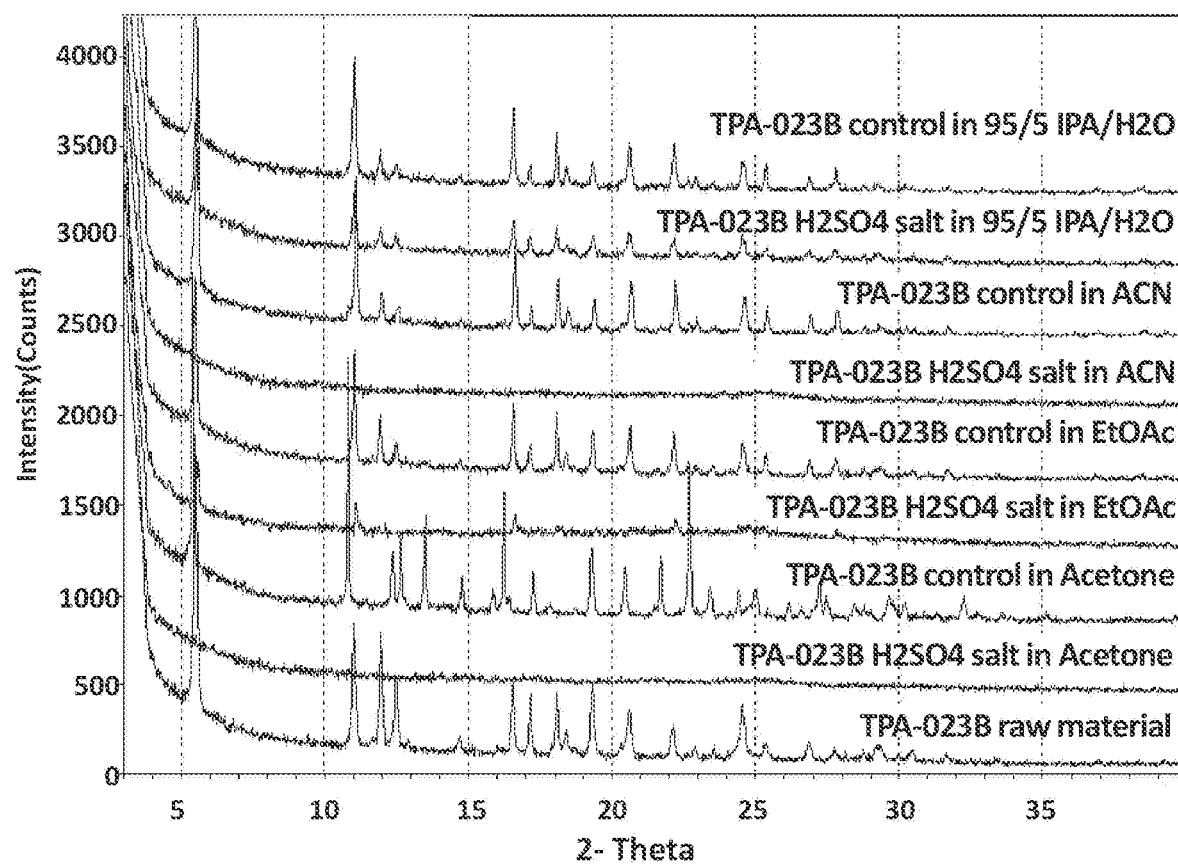
FIG. 21 illustrates XRPD patterns of TPA023B Sulfate Screening
Figure 22:
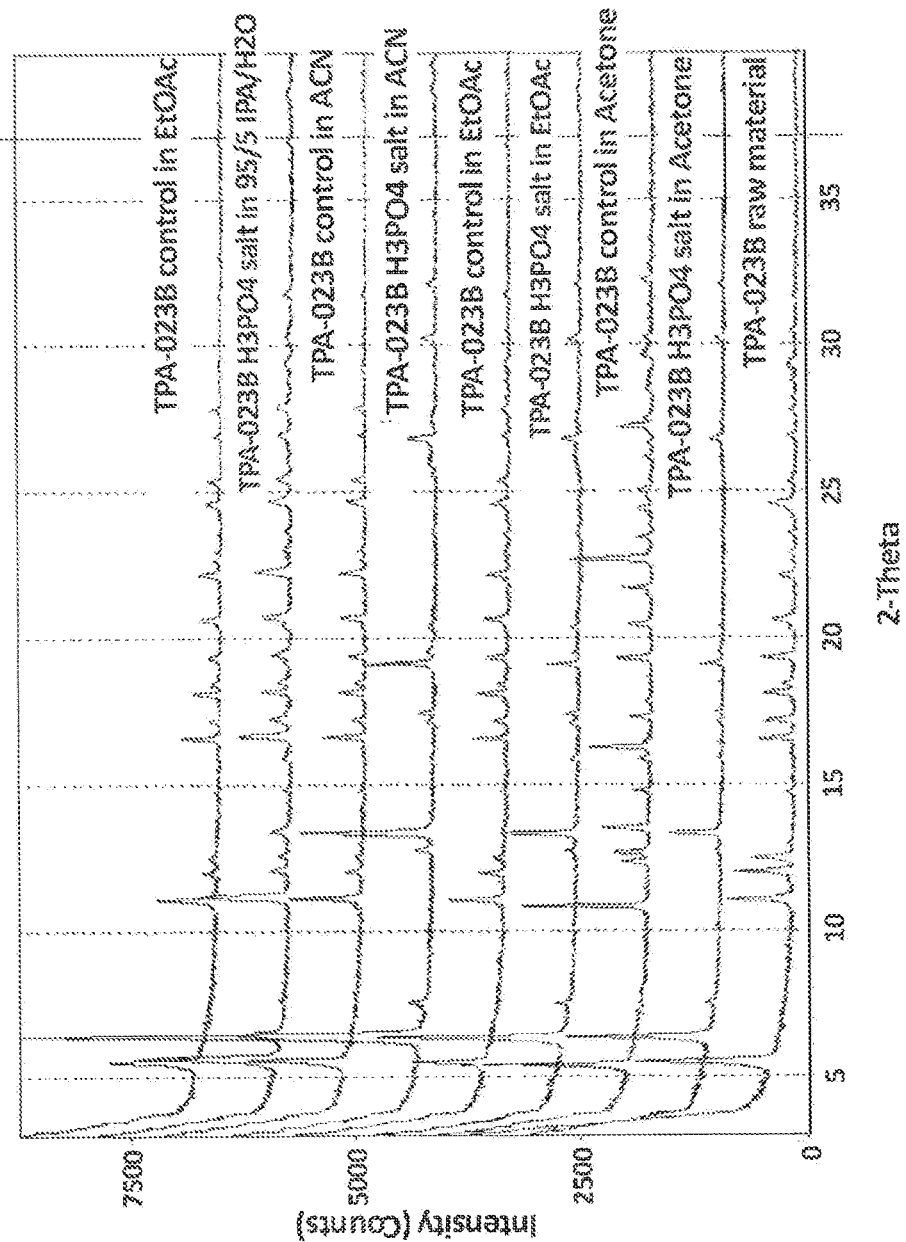
FIG. 22 illustrates XRPD patterns of TPA023B Phosphoric Acid Salt Screening
Figure 23:
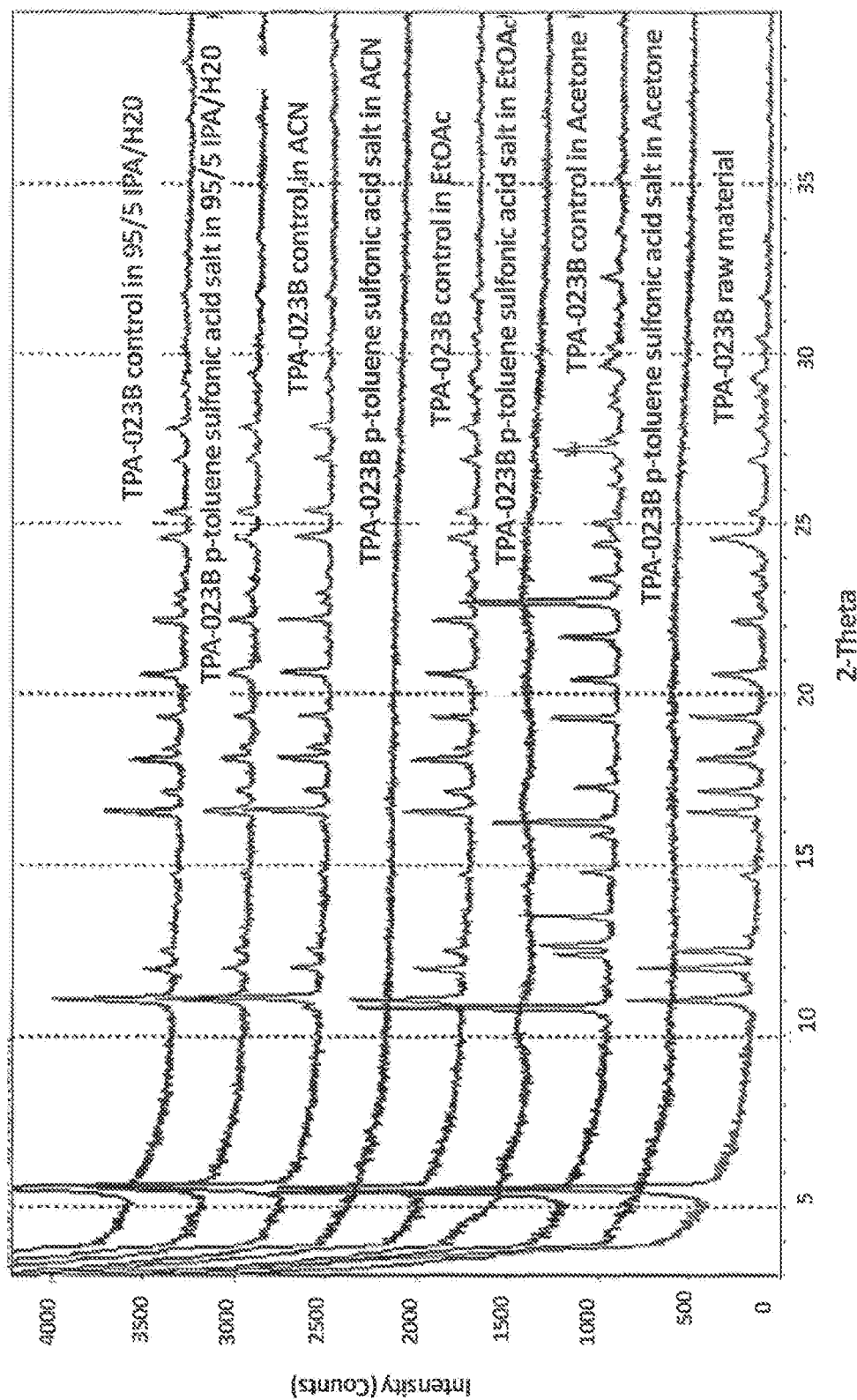
FIG. 23 illustrates XRPD patterns of TPA023B Tosylate Screening
Figure 24:
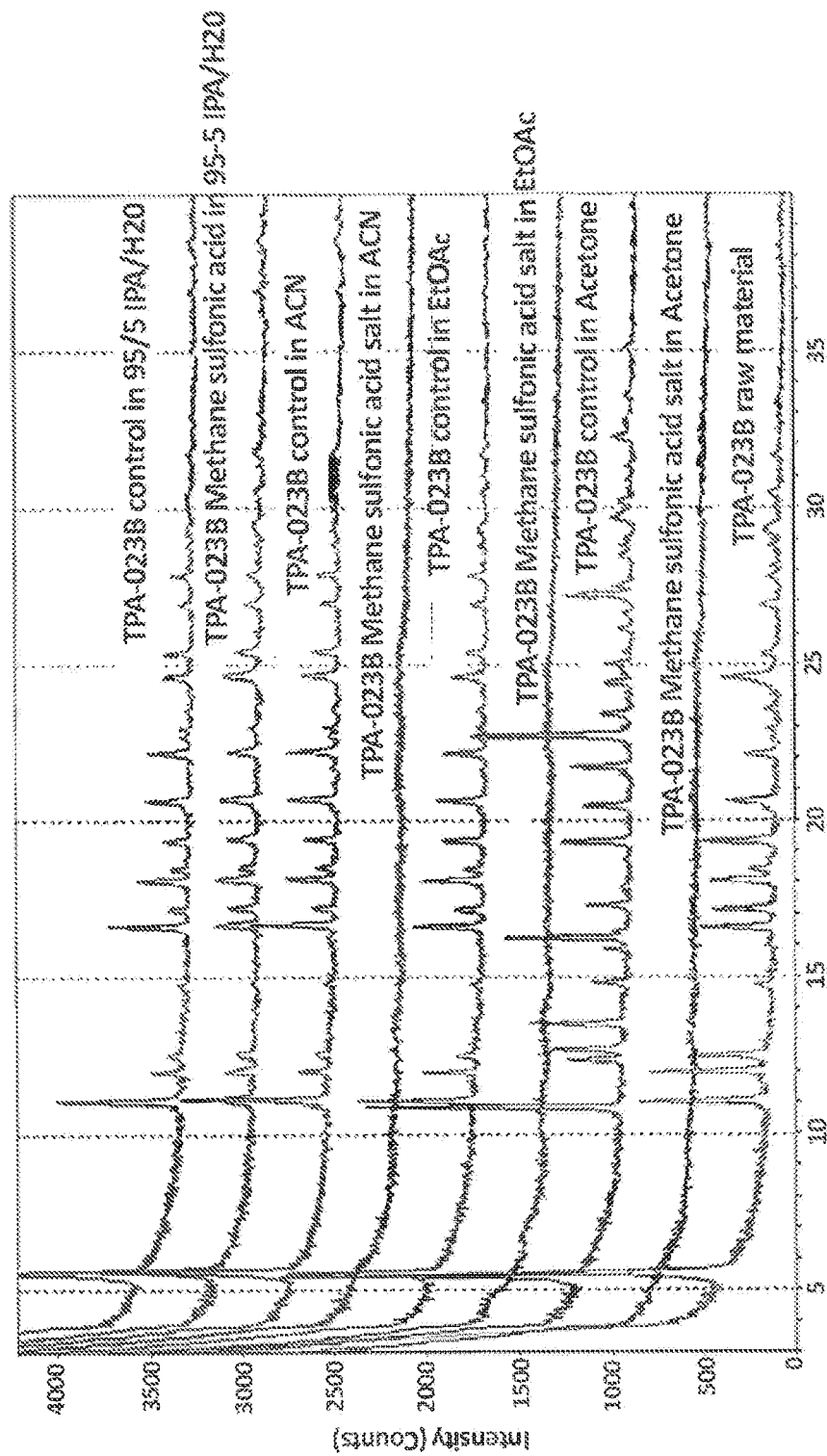
FIG. 24 illustrates XRPD patterns of TPA023B Methane Sulfonic Acid Salt Screening

In one or more embodiments the present disclosure introduces a new, stable polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid. In one or more embodiments, protonated 2',6-difluoro-5'-[3-(1-hydroxy-1-methylethyl)-imidazo[1,2-b][1,2,4]triazin-7-yl]biphenyl-2-carbonitrile has a pKa of 2.19 as measured in Example 23. Phosphoric acid is reported to have a pKa of 2.16. Because the pKa's are similar, it is unexpectedly discovered that 2',6-difluoro-5'-[3-(1-hydroxy-1-methylethyl)-imidazo[1,2-b][1,2,4]triazin-7-yl]biphenyl-2 carbonitrile can form a stable crystal polymorph with phosphoric acid. In one or more embodiments, this crystal form is a salt. In one or more embodiments, this crystal form is a co-crystal. This crystalline polymorph is designated "Phosphate Polymorphic Form A" (i.e., Phosphate Form A) and exhibits an X-Ray Powder Diffraction (XRPD) pattern having characteristic peak locations of at least three, at least six, at least nine, at least twelve, or all values selected from the group consisting of: about 6.4, 7.5, 12.7, 13.3, 17.1, 17.4, 18.5, 19.1, 19.7, 26.7, 30.2, and 32.1±0.2 degrees, 2-theta, when measured using the parameters described in Table 1. In one or more embodiments, Phosphate Polymorphic Form A exhibits an XRPD pattern substantially the same as the XRPD pattern shown in FIG. 1. In one or more embodiments, Phosphate Polymorphic Form A exhibits an XRPD pattern substantially the same as the XRPD pattern shown in FIG. 19. In some embodiments, Phosphate Polymorphic Form A provides an XRPD pattern having characteristic peak locations of at least three, at least six, at least nine, at least twelve, at least fifteen or all values selected from the group consisting of: about 6.4, 7.5, 10.2, 12.7, 13.3, 14.5, 16.0, 17.1, 17.4, 17.9, 18.5, 19.1, 19.7, 20.3, 20.9, 21.5, 22.6, 23.7, 26.2, 26.7, 26.9, 27.5, 28.4, 30.2, and 32.1±0.2 degrees, 2-theta, when measured using the parameters described in Table 1. In some embodiments, Phosphate Polymorphic Form A exhibits an XRPD pattern having a characteristic peak located at about 6.4±0.2 degrees, 2-theta. In some embodiments, Phosphate Polymorphic Form A exhibits an XRPD pattern having a characteristic peak located at about 7.5±0.2 degrees, 2-theta. In some embodiments, Phosphate Polymorphic Form A exhibits an XRPD pattern having a characteristic peak located at about 13.3±0.2 degrees, 2-theta. In some embodiments, Phosphate Polymorphic Form A exhibits an XRPD pattern having a characteristic peak located at about 17.4±0.2 degrees, 2-theta. In some embodiments, Phosphate Polymorphic Form A exhibits an XRPD pattern having a characteristic peak located at about 18.5±0.2 degrees, 2-theta. In some embodiments, Phosphate Polymorphic Form A exhibits an XRPD pattern having a characteristic peak located at about 19.1±0.2 degrees, 2-theta. In some embodiments, Phosphate Polymorphic Form A exhibits an XRPD pattern having a characteristic peak located at about 26.7±0.2 degrees, 2-theta. In some embodiments, Phosphate Polymorphic Form A exhibits an XRPD pattern having a characteristic peak located at about 30.2±0.2 degrees, 2-theta. In one or more embodiments, Phosphate Polymorphic Form A exhibits an XRPD pattern substantially the same as an XRPD pattern labelled as Phosphate Form A in FIG. 30.

TABLE 1

XRPD Parameters

| Parameters | Settings/Values |
| --- | --- |
| X-Ray wavelength | Cu: K-Alpha (λ = 1.54179Å) |
| X-Ray tube setting | Voltage: 40 kV; Current: 40 mA |
| Scan scope | 3 to 40 deg |
| Sample rotation speed | 15 rpm |
| Scanning rate | 10 deg./min |

In some embodiments, Phosphate Polymorphic Form A is a stable form. In some embodiments, Phosphate Polymorphic Form A can be stored at various temperatures and relative humidities. For example, Phosphate Polymorphic Form A can be stored at about −20° C., about −10° C., about 0° C., about 5° C., about 15° C., about 25° C., about 40° C., about 60° C., and about 80° C. For another example, Phosphate Polymorphic Form A can be stored at 10% RH, 20% RH, 30% RH, 40% RH, 50% RH, 60% RH, 75% RH, 90% RH, or 95% RH. In some embodiments, Phosphate Polymorphic Form A is stable at about 25° C. for at least 7 days, at least 14 days, at least 21 days, at least a month, at least 2 months, at least 3 months, at least 6 months, at least 9 months, at least 12 months, or at least 24 months. In some embodiments, Phosphate Polymorphic Form A is stable at about 25° C. for at least 36 months, at least 48 months, or at least 60 months. In some embodiments, Phosphate Polymorphic Form A is stable at about 40° C. for at least 3 days, at least 7 days, at least 14 days, at least 21 days, at least a month, at least 2 months, at least 3 months, at least 6 months, at least 9 months, at least 12 months, or at least 24 months. In some embodiments, Phosphate Polymorphic Form A is stable at about 60° C. for at least 3 days, at least 7 days, at least 14 days, at least 21 days, at least a month, at least two months, at least 3 months, at least 6 months, at least 12 months, or at least 24 months. In some embodiments, a stable Phosphate Polymorphic Form A has about 80%, 85%, 90%, 91%, 92%, 93%, 94%, 95%, 96%, 97%, 98%, 99% w/w or greater of the initial phosphate salt amount at the end of the given storage period. In some embodiments, a stable Phosphate Polymorphic Form A has about 20%, 15%, 10%, 5%, 2%, 1% w/w or less total impurity or related substances at the end of the given storage period. In some embodiments, Phosphate Polymorphic Form A provides an XRPD pattern substantially the same post-storage at about 40° C. and 75% RH for at least a week. In some embodiments, Phosphate Polymorphic Form A provides an XRPD pattern substantially the same post-storage at about 40° C. and 75% RH for at least two weeks. In some embodiments, Phosphate Polymorphic Form A provides an XRPD pattern substantially the same post-storage at about 40° C. and 75% RH for at least a month. In some embodiments, Phosphate Polymorphic Form A provides an XRPD pattern substantially the same post-storage at about 40° C. and 75% RH for at least three months. In some embodiments, Phosphate Polymorphic Form A provides an XRPD pattern substantially the same post-storage at about 40° C. and 75% RH for at least six months. In some embodiments, Phosphate Polymorphic Form A provides an XRPD pattern substantially the same post-storage at about 40° C. and 75% RH for at least nine months. In some embodiments, Phosphate Polymorphic Form A provides an XRPD pattern substantially the same post-storage at about 40° C. and 75% RH for at least twelve months.

Figure 2A:
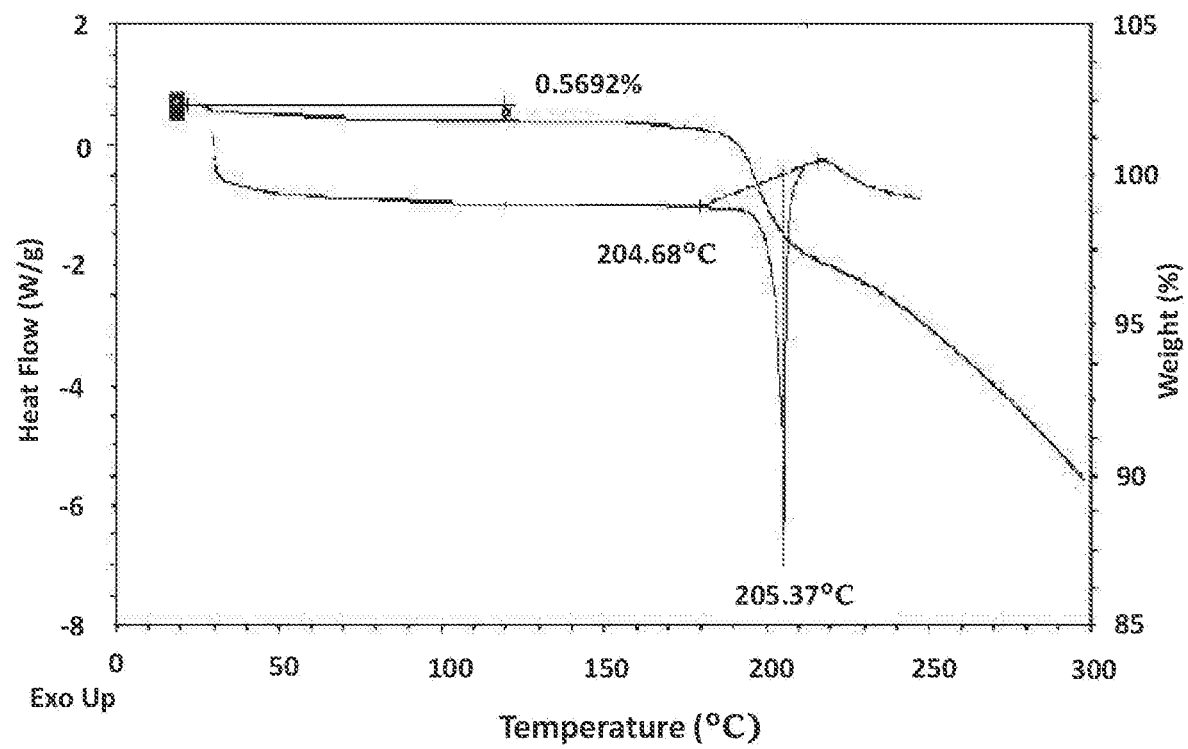
FIGS. 2A-2C illustrate a DSC/TGA thermogram for TPA023B phosphate Form A (FIG. 2A); an NMR spectrum of TPA023B phosphate Form A (FIG. 2B); and an additional DSC/TGA thermogram for TPA023B phosphate Form A (FIG. 2C)
Figure 2B:
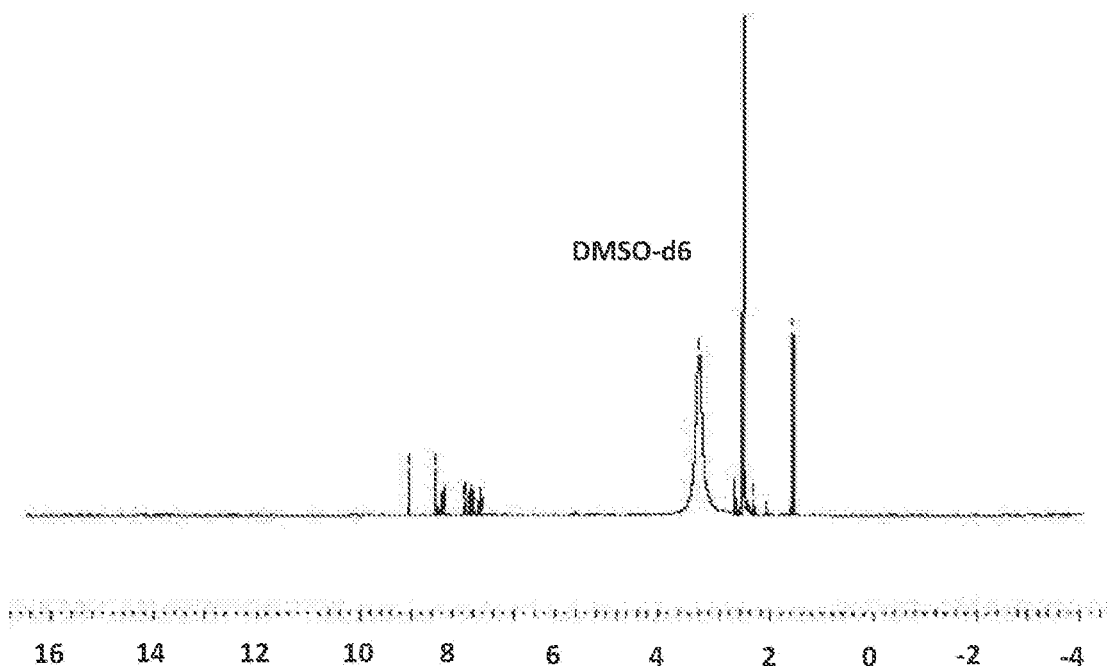
Figure 2C:
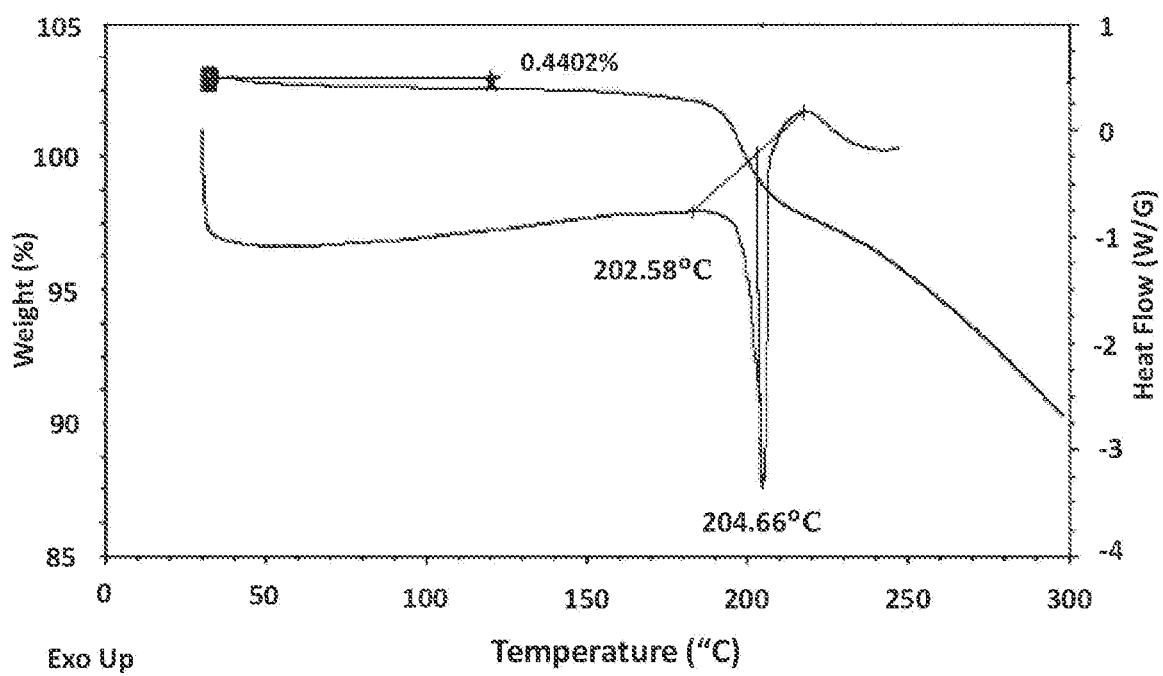
Figure 26:
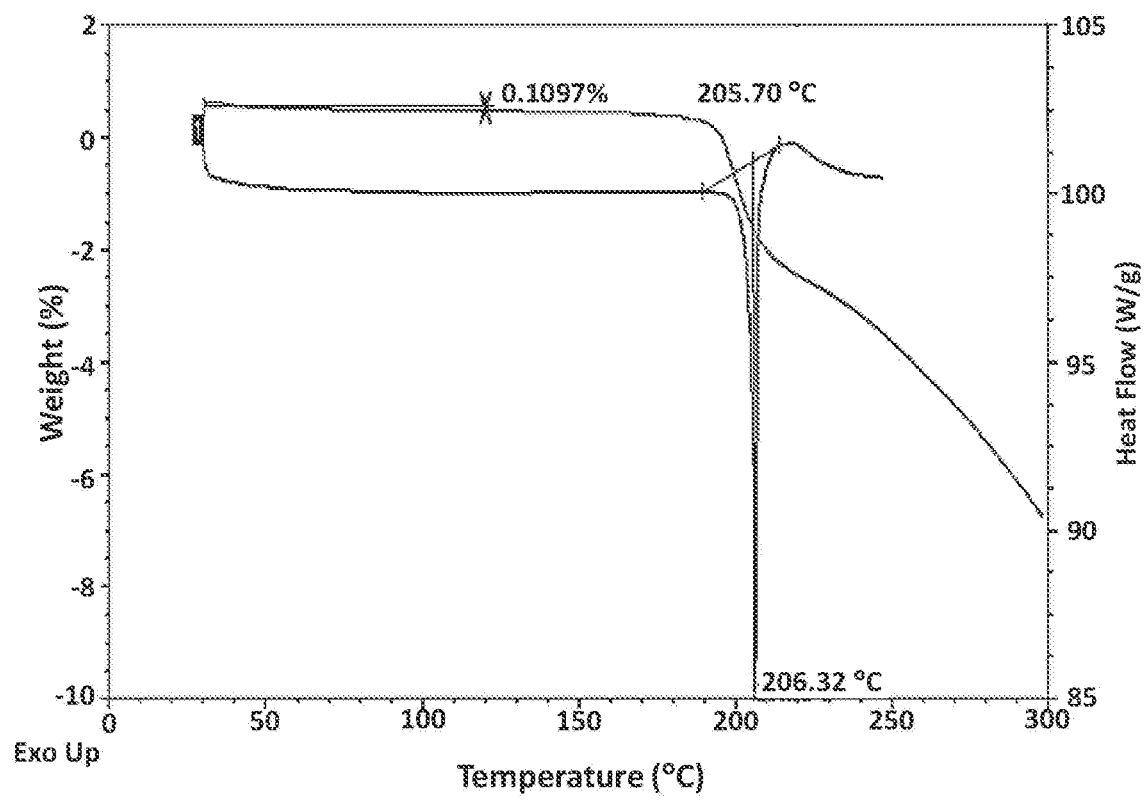
FIG. 26 illustrates the TGA and DSC results of TPA023B Phosphoric Acid Salt in ACN system (TPA023B phosphate Form A)

In one or more embodiments, Phosphate Polymorphic Form A has a melting range of from about 199° C. to about 209° C. In one or more embodiments, Phosphate Polymorphic Form A exhibits a differential scanning calorimetry (DSC) thermogram comprising an endothermic peak at about 205° C. In one or more embodiments, Phosphate Polymorphic Form A provides a DSC thermogram comprising an endothermic peak at about 206° C. In some embodiments, Phosphate Polymorphic Form A provides a DSC thermogram comprising a single endothermic peak with an onset temperature of 203° C. In some embodiments, Phosphate Polymorphic Form A provides a DSC thermogram comprising a single endothermic peak with an onset temperature of 204° C. In some embodiments, Phosphate Polymorphic Form A provides a DSC thermogram comprising a single endothermic peak with an onset temperature of 205° C. In one or more embodiments, Phosphate Polymorphic Form A exhibits a DSC thermogram substantially the same as the DSC thermogram shown in FIG. 2A. In some embodiments, Phosphate Polymorphic Form A provides a DSC thermogram substantially the same as shown in FIG. 2C. In one or more embodiments, Phosphate Polymorphic Form A exhibits a DSC thermogram substantially the same as the DSC thermogram shown in FIG. 26. This melting point is obtained using DSC with a heating rate of 10° C./min. In some embodiments, Phosphate Polymorphic Form A displays birefringence under polarized light. Phosphate Polymorphic Form A can be synthesized using the method of Example 5. In one or more embodiments, pharmaceutical compositions comprising the Phosphate Polymorphic Form A are described. In one or more embodiments, the disclosure includes purified forms of the crystalline Phosphate Polymorphic Form A.

In one or more embodiments, the Phosphate Polymorphic Form A described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the Phosphate Polymorphic Form A described herein comprises an impurity. In some embodiments, the impurity in Phosphate Polymorphic Form A is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

In some embodiments, Phosphate Polymorphic Form A has a plasma half-life that is at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, or at least 15 hours in the plasma of a rat. In some embodiments, Phosphate Polymorphic Form A has a plasma half-life that is at most 5 hours, at most 6 hours, at most 7 hours, at most 8 hours, at most 9 hours, at most 10 hours, at most 11 hours, at most 12 hours, at most 13 hours, at most 14 hours, at most 15 hours, at most 20 hours, or at most 40 hours in the plasma of a rat. In some embodiments, Phosphate Polymorphic Form A has a plasma half-life that is from about 8 hours to about 15 hours in the plasma of a rat. In some embodiments, Phosphate Polymorphic Form A has a plasma half-life that is from about 10 hours to about 13 hours in the plasma of a rat.

Phosphate Polymorphic Form A can have a higher solubility than a free base form of TPA023B. For example, the solubility can be determined as described in example 15. In some embodiments, the solubility of Phosphate Polymorphic Form A is at least 1.1 fold, 1.5 fold, 2 fold, 3 fold, 4 fold, 5 fold, 6 fold, 7 fold, or 8 fold higher than the solubility of Free Base Form A in simulated gastric fluid (SGF). In some embodiments, the solubility of Phosphate Polymorphic Form A is at least 1.1 fold, 1.5 fold, 2 fold, 3 fold, 4 fold, 5 fold, 6 fold, 7 fold, or 8 fold higher than the solubility of Free Base Form A in Fasted-state simulated intestinal fluid (FaSSIF). In some embodiments, the solubility of Phosphate Polymorphic Form A is at least 1.1 fold, 1.5 fold, 2 fold, 3 fold, 4 fold, 5 fold, 6 fold, 7 fold, or 8 fold higher than the solubility of Free Base Form A in Fed-state simulated intestinal fluid (FeSSIF) than Free Base Polymorphic Form A.

Phosphate Patterns

In some embodiments, described herein is a mixture comprising crystalline polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid. This crystalline polymorph mixture is designated "Phosphate Polymorphic Pattern B" (i.e., phosphate Pattern B) and exhibits an XRPD pattern having characteristic peak locations of at least three, at least six, at least nine, at least twelve, at least fifteen or all values selected from the group consisting of about: 6.3, 7.0, 8.0, 9.4, 10.9, 12.7, 13.2, 14.0, 14.7, 16.1, 17.3, 19.4, 19.7, 22.1, 24.1, 24.3, 26.6, 27.0, and 28.2±0.2-degrees, 2-theta, when measured using the parameters described in Table 1. TPA023B Phosphate Polymorphic Pattern B can comprise TPA023B phosphate Form A. Phosphate Polymorphic Pattern B can also comprise Phosphate Pattern G. In one or more embodiments, Phosphate Polymorphic Pattern B exhibits an XRPD pattern substantially the same as the XRPD pattern shown in FIG. 3. In one or more embodiments, Phosphate Polymorphic Pattern B has a melting/dehydration/desolvation range of from about 80° C. to about 205° C. In one or more embodiments, Phosphate Polymorphic Pattern B exhibits a DSC thermogram comprising endothermic peaks at about 193 and 203° C. In one or more embodiments, Phosphate Polymorphic Pattern B exhibits a DSC thermogram substantially the same as the DSC thermogram shown in FIG. 4A. In one or more embodiments, Phosphate Polymorphic Pattern B can be synthesized using the method of Example 6. In one or more embodiments, pharmaceutical compositions comprising the Phosphate Polymorphic Pattern B are described.

Figure 30:
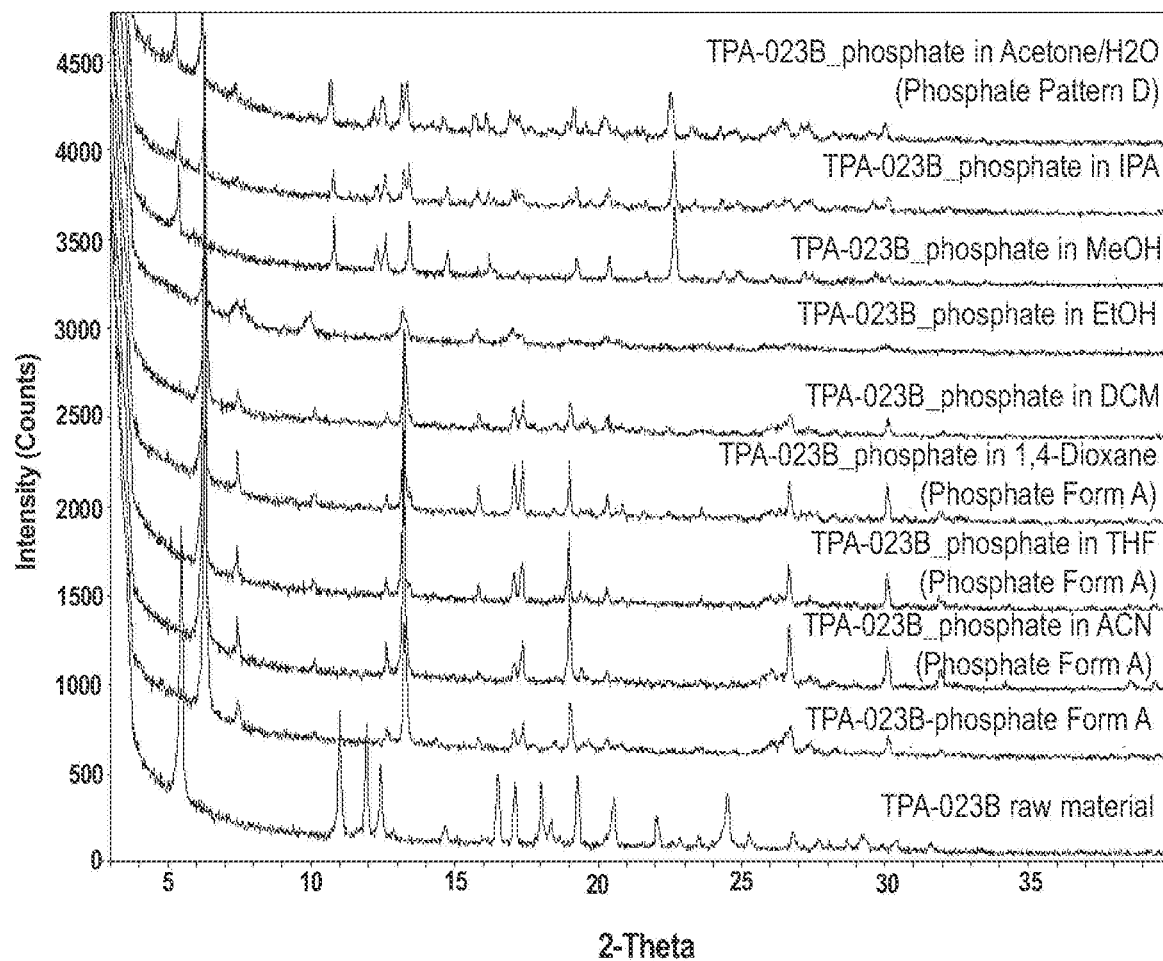
FIG. 30 illustrates XRPD patterns of TPA023B phosphate solids obtained by polymorph screening using the heat-cooling method

In some embodiments, described herein is another mixture comprising crystalline polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid. This crystalline polymorph mixture is designated "Phosphate Polymorphic Pattern D" (i.e., phosphate Pattern D) and exhibits an XRPD pattern having characteristic peak locations of at least three, at least six, at least nine, at least twelve, at least fifteen or all values selected from the group consisting of about: 5.3, 6.3, 7.4, 10.8, 12.2, 12.6, 13.1, 13.3, 14.6, 15.8, 16.0, 16.9, 17.1, 18.9, 19.0, 19.4, 20.1, 22.5, 23.1, 24.3, 24.9, 26.0, 26.5, 27.2, 29.5 and 30.0±0.2-degrees, 2-theta, when measured using the parameters described in Table 1. TPA023B Phosphate Polymorphic Pattern D can comprise TPA023B phosphate Form A. TPA023B Phosphate Polymorphic Pattern D can also comprise TPA023B Free Base Form C. In one or more embodiments, Phosphate Polymorphic Pattern D exhibits an XRPD pattern substantially the same as the XRPD pattern labelled Phosphate Pattern D as shown in FIG. 30. In one or more embodiments, Phosphate Polymorphic Pattern D has a melting/dehydration/desolvation range of from about 190 to about 210° C. In one or more embodiments, Phosphate Polymorphic Pattern D exhibits a DSC thermogram comprising an endothermic peak at about 202° C. In one or more embodiments, Phosphate Polymorphic Pattern D exhibits a DSC thermogram substantially the same as the DSC thermogram shown in FIG. 31. In one or more embodiments, Phosphate Polymorphic Pattern D can be synthesized using the method described in Example 27. In one or more embodiments, pharmaceutical compositions comprising the Phosphate Polymorphic Pattern D are described.

In one or more embodiments, a mixture comprising crystalline polymorph of the salt or co-crystal of 2',6-difluoro-5'-[3-(1-hydroxy-1-methylethyl)-imidazo[1,2-b][1,2,4]triazin-7-yl]biphenyl-2-carbonitrile with phosphoric acid is described. This crystalline polymorph mixture is designated "Phosphate Polymorphic Pattern E" and exhibits an XRPD pattern having characteristic peak locations of at least three, at least six, at least nine, at least twelve, or all values selected from the group consisting of about: 6.4, 7.6, 13.0, 13.3, 15.5, 15.8, 17.0, 17.4, 19.1, 19.5, 20.3, 20.7, 26.8, and 30.1±0.2-degrees, 2-theta, when measured using the parameters described in Table 1. TPA023B Phosphate Polymorphic Pattern E is likely a mixture comprising TPA023B phosphate Form A. In one or more embodiments, Phosphate Polymorphic Pattern E exhibits an XRPD pattern substantially the same as the XRPD pattern shown in FIG. 7. In one or more embodiments, Phosphate Polymorphic Pattern E has a melting/dehydration/desolvation range from about 60° C. to about 95° C. In one or more embodiments, Phosphate Polymorphic Pattern E exhibits a DSC thermogram comprising an endothermic peak at about 191° C. In one or more embodiments, Phosphate Polymorphic Pattern E exhibits a DSC thermogram comprising an endothermic peak at about 199° C. In one or more embodiments, Phosphate Polymorphic Pattern E exhibits a DSC thermogram substantially the same as the DSC thermogram shown in FIG. 8. This melting point is obtained using DSC with a heating rate of 10° C./min. In one or more embodiments, Phosphate Polymorphic Pattern E can be synthesized using the method of Example 8. In one or more embodiments, pharmaceutical compositions comprising the Phosphate Polymorphic Pattern E are described.

Tosylate

In one or more embodiments, a crystalline polymorph of the salt of 2',6-difluoro-5'-[3-(1-hydroxy-1-methylethyl)-imidazo[1,2-b][1,2,4]triazin-7-yl]biphenyl-2-carbonitrile with p-toluenesulfonic acid is also described. This crystalline polymorph is designated "Tosylate Polymorphic Form A" (i.e., Tosylate Form A) and exhibits an XRPD pattern having characteristic peak locations of at least three, at least six, at least nine, at least twelve, at least fifteen or all values selected from the group consisting of about: 7.0, 12.4, 12.6, 13.0, 14.1, 15.4, 15.7, 16.3, 17.5, 18.3, 19.0, 21.0, 22.3, 23.0, 24.9, and ±0.2-degrees, 2-theta, when measured using the parameters described in Table 1. In one or more embodiments, Tosylate Polymorphic Form A exhibits an XRPD pattern substantially the same as the XRPD pattern shown in FIG. 17A. In one or more embodiments, Tosylate Polymorphic Form A has a melting range of from about 155° C. to about 175° C. In one or more embodiments, Tosylate Polymorphic Form A exhibits a DSC thermogram comprising an endothermic peak at about 170° C. In one or more embodiments, Tosylate Polymorphic Form A exhibits a DSC thermogram substantially the same as the DSC thermogram shown in FIG. 18. This melting point is obtained using DSC with a heating rate of 10° C./min. In some embodiments, Tosylate Polymorphic Form A can be synthesized using the method of Example 9. In one or more embodiments, pharmaceutical compositions comprising the Tosylate Polymorphic Form A are described. In one or more embodiments, the disclosure provides purified forms of the crystalline Tosylate Polymorphic Form A.

Free Base

Figure 9:
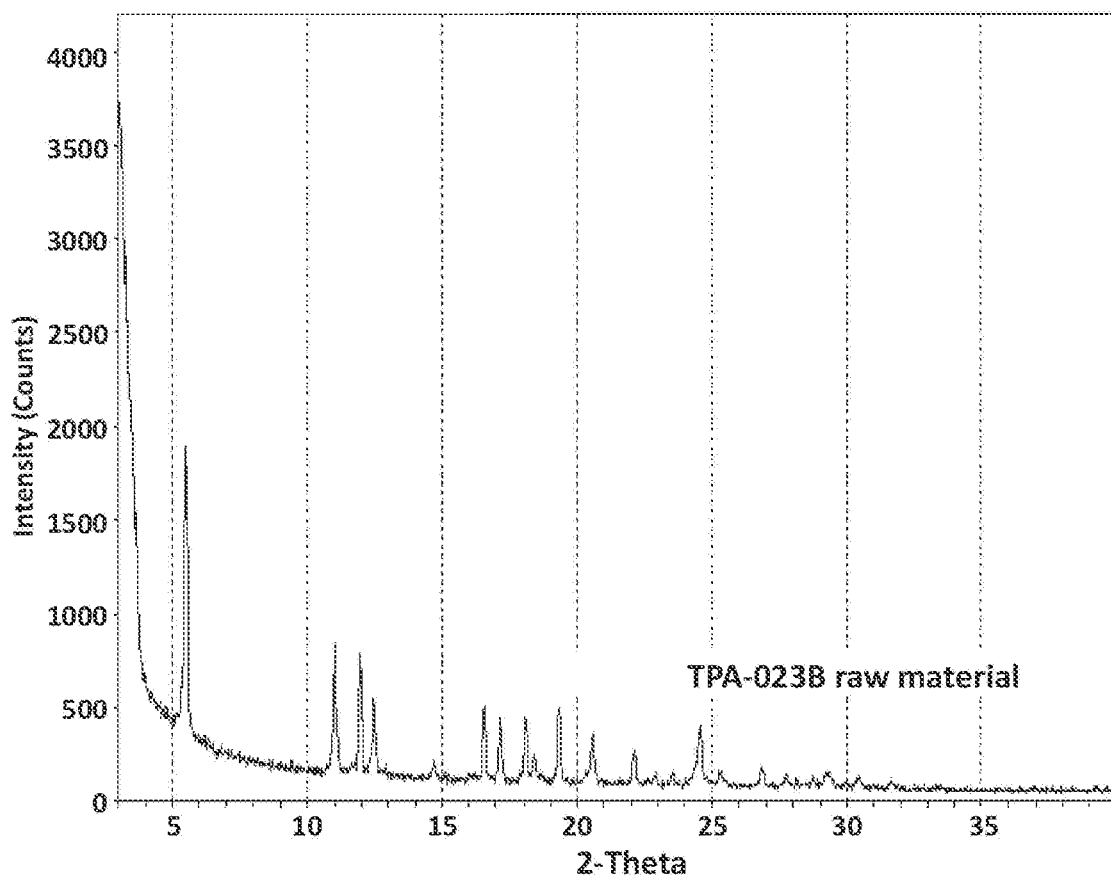
FIG. 9 illustrates an XRPD pattern for TPA023B freebase Form A
Figure 10A:
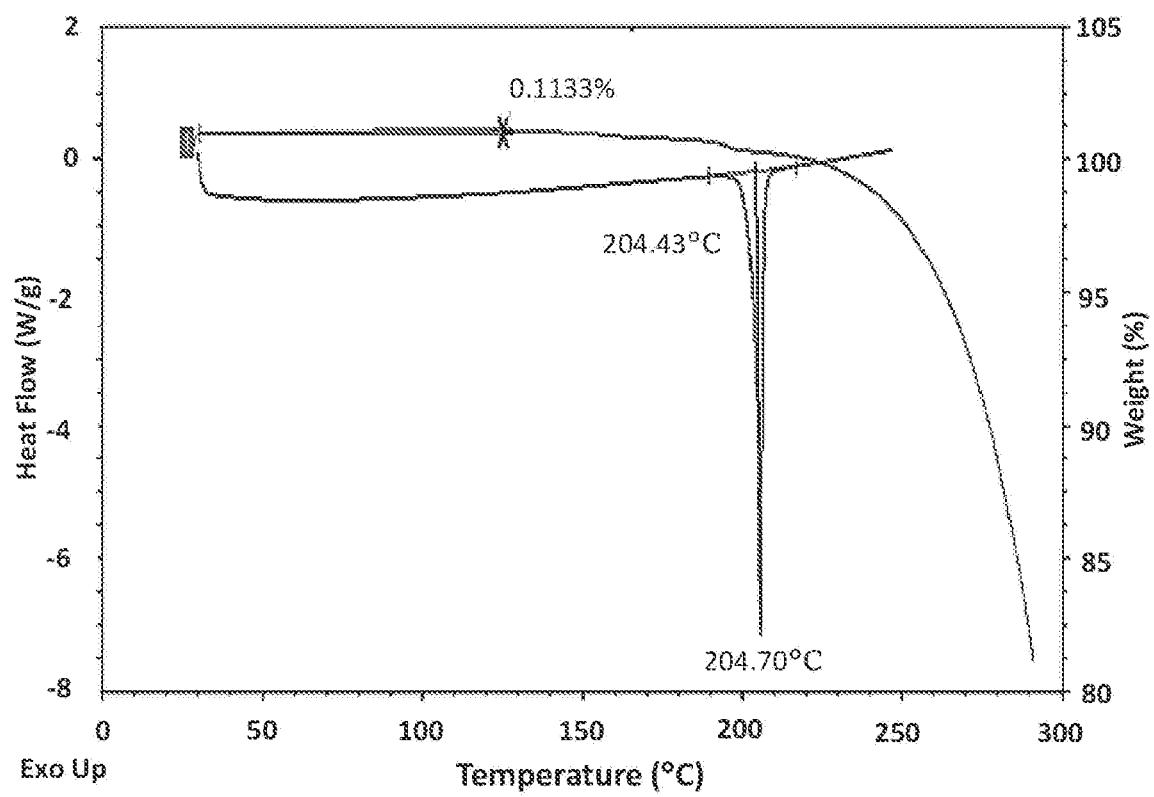
FIGS. 10A and 10B illustrate a DSC/TGA thermogram for TPA023B freebase Form A (FIG. 10A); and an NMR spectrum of TPA023B freebase Form A (FIG. 10B)

In one or more embodiments, a crystalline polymorph of 2',6-difluoro-5'-[3-(1-hydroxy-1-methylethyl)-imidazo[1,2-b][1,2,4]triazin-7-yl]biphenyl-2-carbonitrile has also been identified. This crystalline polymorph is designated "Free Base Polymorphic Form A" and exhibits an XRPD pattern having characteristic peak locations of at least three, at least six, at least nine, at least twelve, at least fifteen or all values selected from the group consisting of about: 5.5, 11.0, 12.0, 12.5, 14.7, 16.5, 17.1, 18.1, 18.4, 19.3, 20.6, 22.1, 23.5, 24.6, 25.3, 26.8, 27.7, 28.1, 29.3, and 30.5±0.2-degrees, 2-theta, when measured using the parameters described in Table 1. In one or more embodiments, Free Base Polymorphic Form A exhibits an XRPD pattern substantially the same as the XRPD pattern shown in FIG. 9. In one or more embodiments, Free Base Polymorphic Form A has a melting range of from about 195° C. to about 210° C. In one or more embodiments, Free Base Polymorphic Form A exhibits a DSC thermogram comprising an endothermic peak at about 206° C. In one or more embodiments, Free Base Polymorphic Form A exhibits a DSC thermogram substantially the same as the DSC thermogram shown in FIG. 10A. This melting point is obtained using DSC with a heating rate of 10° C./min. In some embodiments, Free Base Polymorphic Form A displays birefringence under polarized light. In some embodiments, Free Base Polymorphic Form A is anhydrate. In some embodiments, Free Base Polymorphic Form A can be synthesized using the method of Example 10. In one or more embodiments, pharmaceutical compositions comprising the Free Base Polymorphic Form A are described. In one or more embodiments, the disclosure includes purified forms of the crystalline Free Base Polymorphic Form A.

Figure 11:
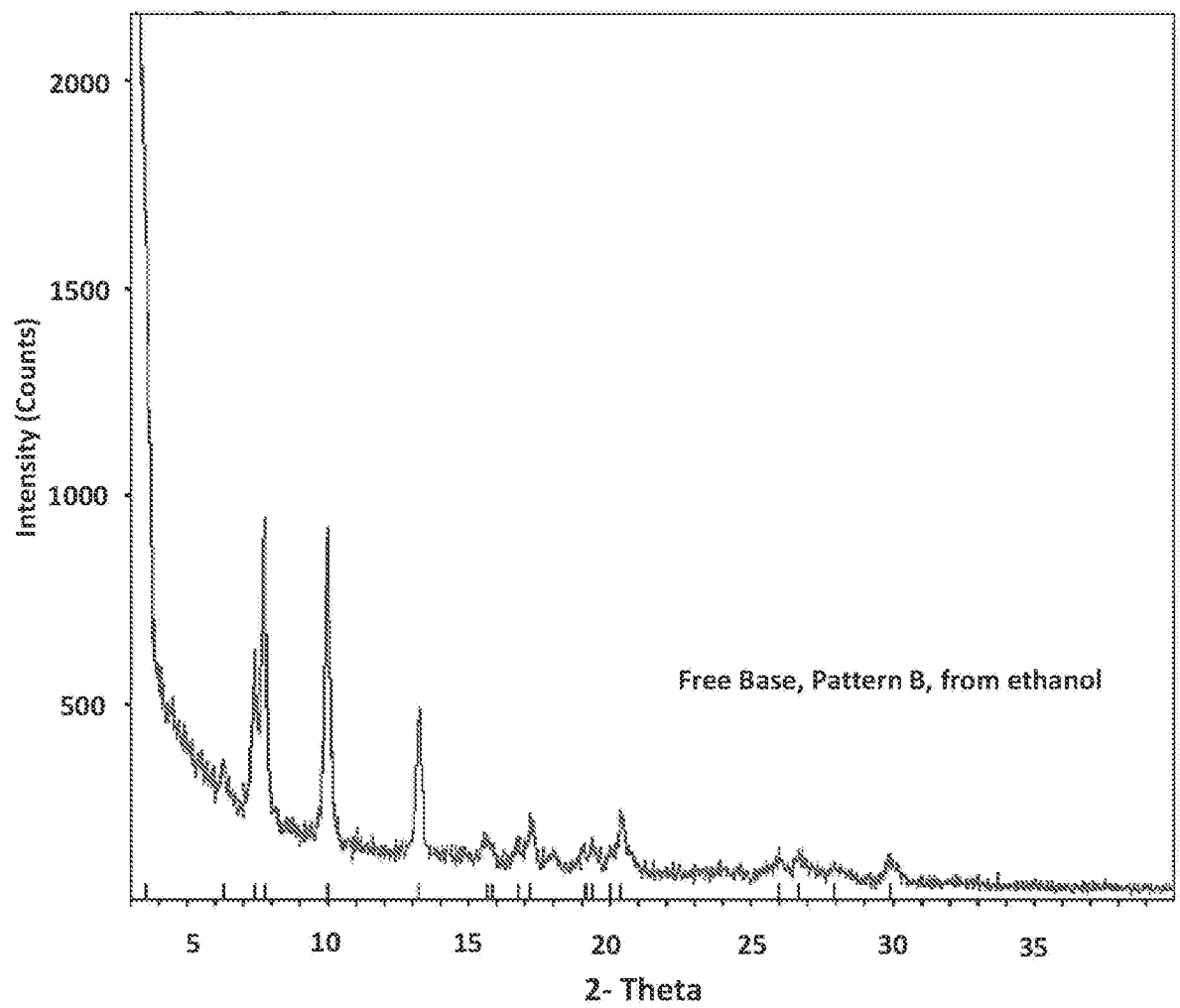
FIG. 11 illustrates an XRPD pattern for TPA023B freebase Form B

In one or more embodiments, the present disclosure further provides a crystalline polymorph of 2',6-difluoro-5'-[3-(1-hydroxy-1-methylethyl)-imidazo[1,2-b][1,2,4]triazin-7-yl]biphenyl-2-carbonitrile. This crystalline polymorph is designated "Free Base Polymorphic Form B" and exhibits an XRPD pattern having characteristic peak locations of at least three, at least six, at least nine, at least twelve, at least fifteen or all values selected from the group consisting of about: 6.3, 7.4, 7.7, 10.0, 13.2, 15.6, 15.8, 16.7, 17.2, 19.1, 19.4, 20.0, 20.4, 26.0, 26.7, 27.9, and 29.9 0.2 degrees, 2-theta, when measured using the parameters described in Table 1. In one or more embodiments, Free Base Polymorphic Form B exhibits an XRPD pattern substantially the same as the XRPD pattern shown in FIG. 11. In one or more embodiments, Free Base Polymorphic Form B has a melting/desolvation range of from about 40° C. to about 150° C. In one or more embodiments, Free Base Polymorphic Form B is synthesized using the method of Example 11. In one or more embodiments, pharmaceutical compositions comprising the Free Base Polymorphic Form B are described. In one or more embodiments, the disclosure provides an ethanol solvate. In one or more embodiments, the disclosure provides purified forms of the crystalline Free Base Polymorphic Form B.

Figure 12:
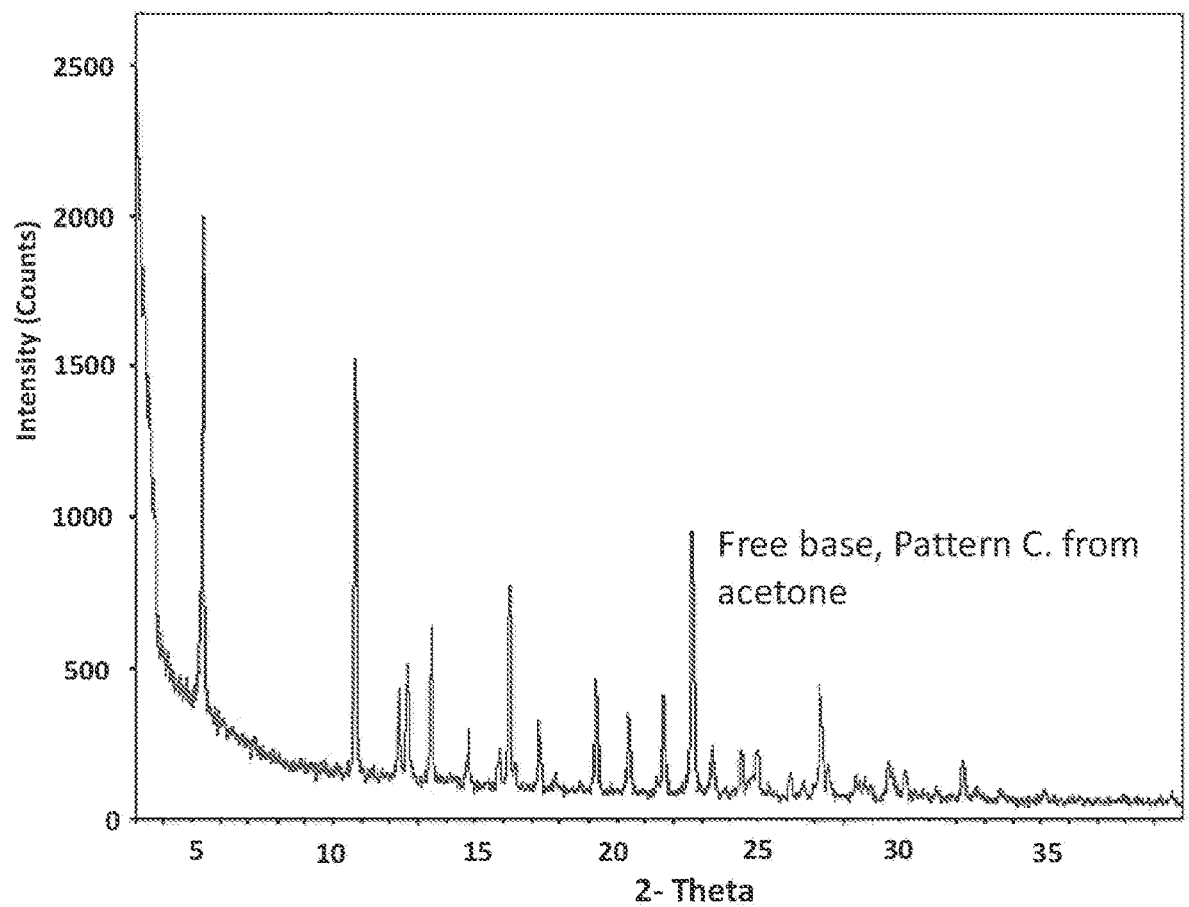
FIG. 12 illustrates an XRPD pattern for TPA023B freebase Form C

In one or more embodiments, a still further crystalline polymorph of 2',6-difluoro-5'-[3-(1-hydroxy-1-methylethyl)-imidazo[1,2-b][1,2,4]triazin-7-yl]biphenyl-2-carbonitrile is described herein. This crystalline polymorph is designated "Free Base Polymorphic Form C" (i.e., Free Base Form C) and exhibits an XRPD pattern having characteristic peak locations of at least three, at least six, at least nine, at least twelve, at least fifteen or all values selected from the group consisting of about: 5.4, 10.8, 12.3, 12.6, 13.5, 14.8, 16.2, 17.3, 19.3, 20.4, 21.7, 22.7, 23.4, 24.4, 25.0, 27.2, 29.6, and 32.2±0.2 degrees, 2-theta, when measured using the parameters described in Table 1. In some embodiments, Free Base Polymorphic Form C provides an XRPD pattern having characteristic peak locations of at least three, at least six, at least nine, at least twelve, at least fifteen or all values selected from the group consisting of about: 5.4, 10.8, 12.3, 12.6, 13.5, 14.8, 15.9, 16.3, 16.4, 17.3, 17.8, 19.3, 20.4, 21.5, 21.7, 22.7, 23.4, 24.4, 24.7, 25.0, 26.1, 26.6, 27.0, 27.2, 27.5, 28.4, 28.7, 29.0, 29.6, 30.2, and 32.3±0.2-degrees, 2-theta, when measured using the parameters described in Table 1. In one or more embodiments, TPA023B Free Base Polymorphic Form C exhibits an XRPD pattern substantially the same as the XRPD pattern shown in FIG. 5. In one or more embodiments, Free Base Polymorphic Form C exhibits an XRPD pattern substantially the same as the XRPD pattern shown in FIG. 12.

Figure 13:
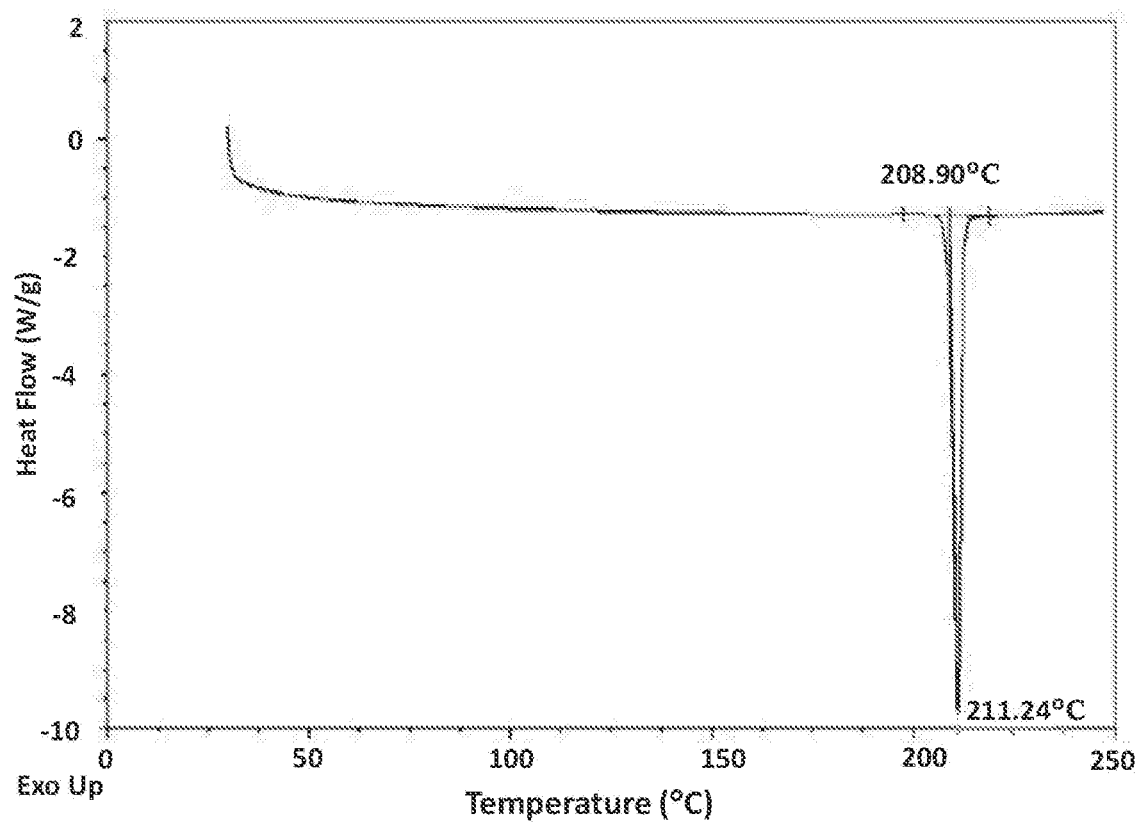
FIG. 13 illustrates a DSC thermogram for TPA023B freebase Form C

In one or more embodiments, Free Base Polymorphic Form C has a melting range of from about 205° C. to about 215° C. In one or more embodiments, Free Base Polymorphic Form C has a melting range from about 195° C. to about 215° C. In one or more embodiments, Free Base Polymorphic Form C exhibits a DSC thermogram comprising an endothermic peak at about 209 to 211° C. In one or more embodiments, Free Base Polymorphic Form C exhibits a DSC thermogram comprising an endothermic peak at about 209° C. In one or more embodiments, Free Base Polymorphic Form C exhibits a DSC thermogram comprising an endothermic peak at about 210° C. In one or more embodiments, Free Base Polymorphic Form C exhibits a DSC thermogram comprising an endothermic peak at about 211° C. In one or more embodiments, Free Base Polymorphic Form C exhibits a DSC thermogram comprising an endothermic peak with an onset temperature at about 209° C. In one or more embodiments, Free Base Polymorphic Form C exhibits a DSC thermogram substantially the same as FIG. 13. In one or more embodiments, Free Base Polymorphic Form C exhibits a DSC thermogram substantially the same as the DSC thermogram shown in FIG. 6. This melting point is obtained using DSC with a heating rate of 10° C./min. In some embodiments, Free Base Polymorphic Form C displays birefringence under polarized light. In one or more embodiments, Free Base Polymorphic Form C can be synthesized using the method of Example 12. In some embodiments, Free Base Polymorphic Form C is an anhydrate. In one or more embodiments, pharmaceutical compositions comprising the Free Base Polymorphic Form C are described. In one or more embodiments, the disclosure provides purified forms of the crystalline Free Base Polymorphic Form C.

In some embodiments, Free Base Polymorphic Form C is a stable form. In some embodiments, Free Base Polymorphic Form C can be stored at various temperatures and relative humidities. For example, Free Base Polymorphic Form C can be stored at about −20° C., about −10° C., about 0° C., about 5° C., about 15° C., about 25° C., about 40° C., and about 60° C. For another example, Free Base Polymorphic Form C can be stored at 10% RH, 20% RH, 30% RH, 40% RH, 50% RH, 60% RH, 75% RH, 90% RH, or 95% RH. In some embodiments, Free Base Polymorphic Form C is stable at about 25° C. for at least at least 7 days, at least 14 days, at least 21 days, at least a month, at least 2 months, at least 3 months, at least 6 months, at least 9 months, at least 12 months, at least 24 months, at least 36 months, at least 48 months, or at least 60 months. In some embodiments, Free Base Polymorphic Form C is stable at about 40° C. for at least 3 days, at least 7 days, at least 14 days, at least 21 days, at least a month, at least 3 months, at least 6 months, at least 9 months, at least 12 months, or at least 24 months. In some embodiments, Free Base Polymorphic Form C is stable at about 60° C. for at least 3 days, at least 7 days, at least 14 days, at least 21 days, at least a month, at least 3 months, at least 6 months, at least 9 months, at least 12 months, or at least 24 months. In some embodiments, a stable TPA023B Free Base Polymorphic Form, such as Free Base Form C, has about 80%, 85%, 90%, 91%, 92%, 93%, 94%, 95%, 96%, 97%, 98%, 99% w/w or greater of the initial free base amount at the end of the given storage period. In some embodiments, a stable TPA023B Free Base Polymorphic Form, such as Free Base Form C, has about 20%, 15%, 10%, 5%, 2%, 1% w/w or less total impurity or related substances at the end of the given storage period. In some embodiments, Free Base Polymorphic Form C provides an XRPD pattern substantially the same post-storage at about 40° C. and 75% RH for at least a week. In some embodiments, Free Base Polymorphic Form C provides an XRPD pattern substantially the same post-storage at about 40° C. and 75% RH for at least two weeks, at least a month, at least 3 months, at least 6 months, at least 9 months, at least 12 months, or at least 24 months.

In one or more embodiments, a Free Base Polymorphic Form described herein, such as Free Base Form C, is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, a Free Base Polymorphic Form, such as Free Base Form C, comprises an impurity. In some embodiments, the impurity in a Free Base Form, such as in Free Base Form C is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

Figure 14:
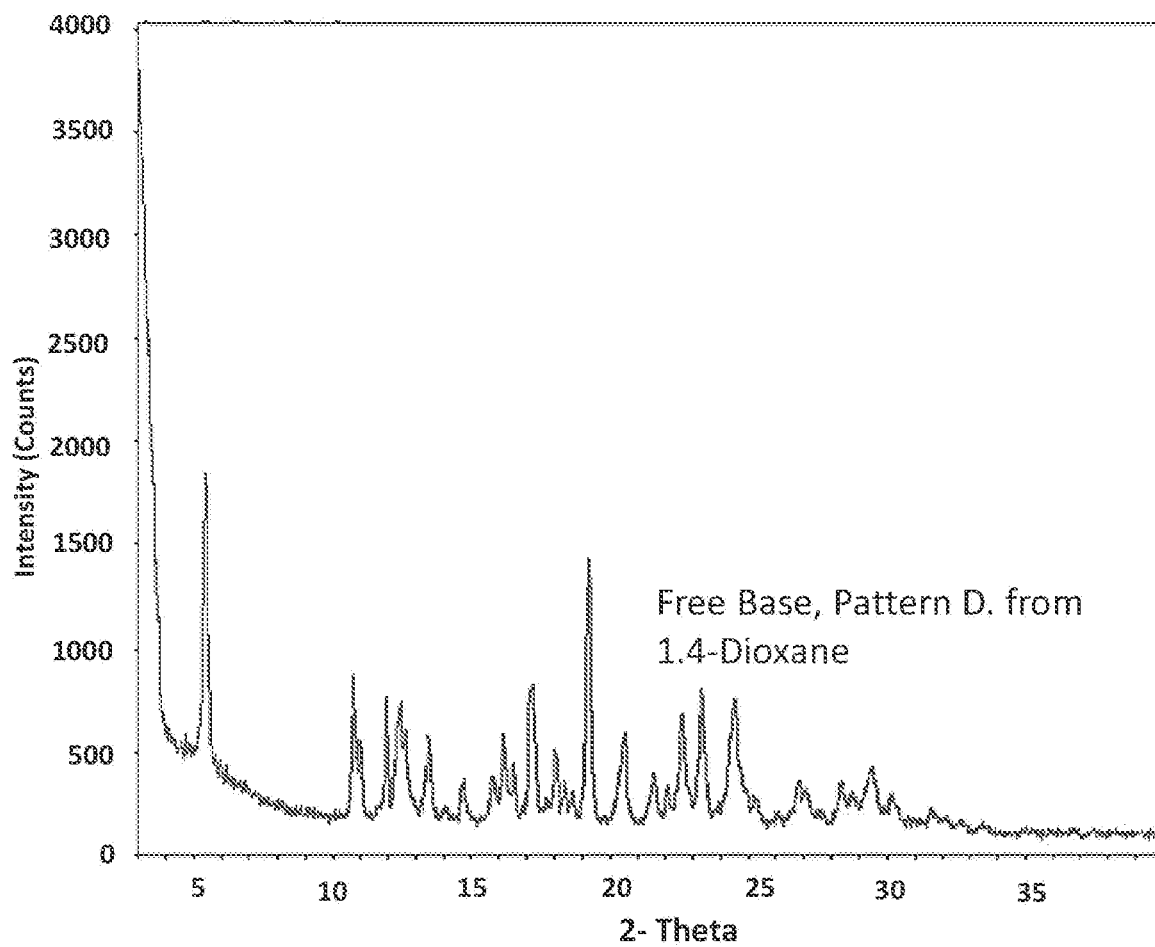
FIG. 14 illustrates an XRPD pattern for TPA023B freebase mixture comprising free base Form A

In one or more embodiments, a crystalline polymorph mixture of 2',6-difluoro-5'-[3-(1-hydroxy-1-methylethyl)-imidazo[1,2-b][1,2,4]triazin-7-yl]biphenyl-2-carbonitrile is described. This crystalline polymorph mixture is designated "Free Base Polymorphic Pattern D" and exhibits an XRPD pattern having characteristic peak locations of at least three, at least six, at least nine, at least twelve, at least fifteen or all values selected from the group consisting of about: 5.4, 10.8, 11.0, 12.0, 12.4, 13.5, 14.7, 15.8, 16.2, 16.5, 17.2, 18.0, 19.3, 20.6, 21.6, 22.6, 23.3, 24.5, 26.8, 27.1, 28.4, 29.5, and 30.2±0.2 degrees, 2-theta, when measured using the parameters described in Table 1. In one or more embodiments, TPA023B Free Base Polymorphic Pattern D can comprise Free Base Form A. In one or more embodiments, TPA023B Free Base Polymorphic Pattern D can comprise Free Base Form C. In one or more embodiments, Free Base Polymorphic Pattern D comprises a dioxane solvate. In one or more embodiments, Free Base Polymorphic Pattern D exhibits an XRPD pattern substantially the same as the XRPD pattern shown in FIG. 14. In one or more embodiments, Free Base Polymorphic Pattern D has a melting/desolvating range of from about 50° C. to about 225° C. Free Base Polymorphic Pattern D can be synthesized using the method of Example 13. In one or more embodiments, pharmaceutical compositions comprising the Free Base Polymorphic Pattern D are described. In one or more embodiments, the disclosure provides purified forms of the crystalline Free Base Polymorphic Pattern D.

Chloride

Figure 15:
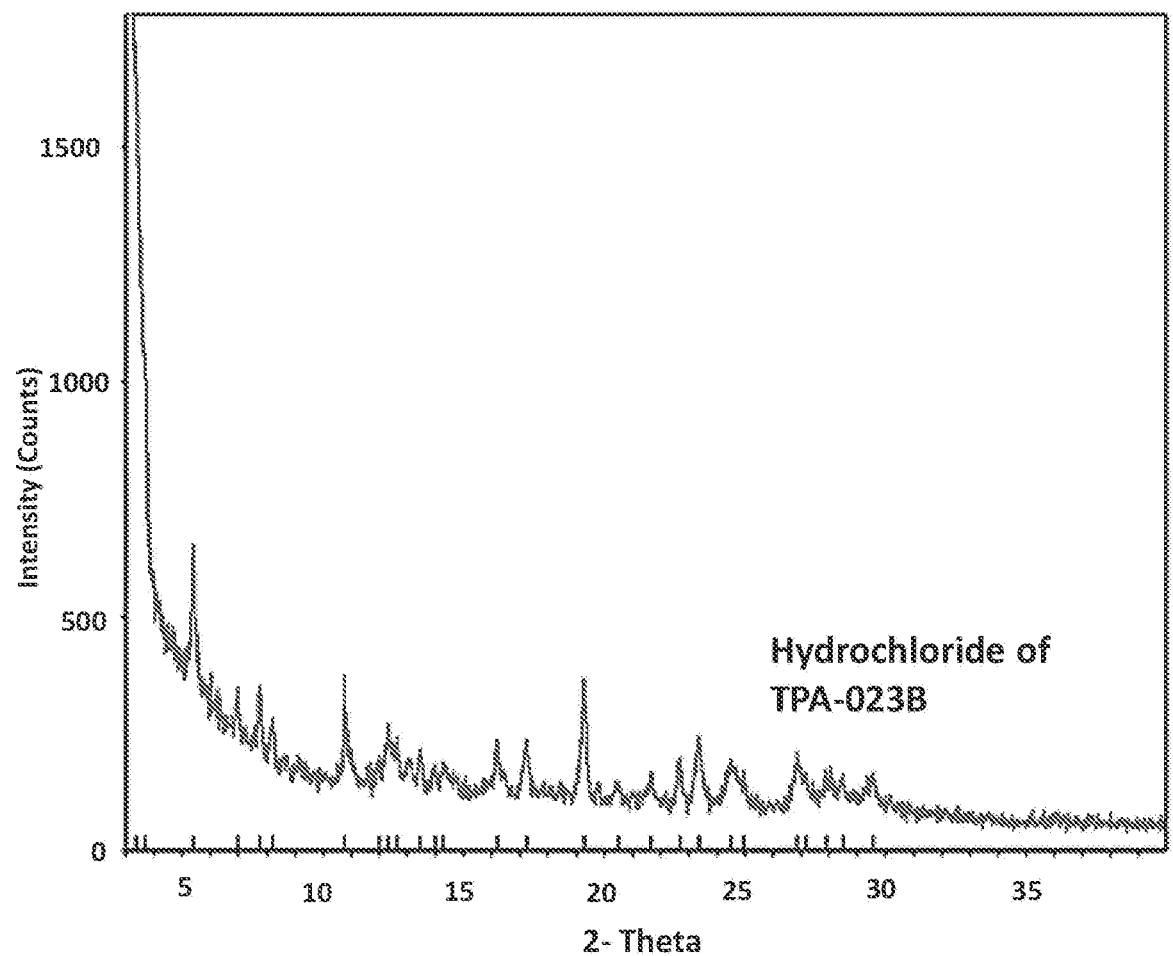
FIG. 15 illustrates an XRPD pattern for TPA023B chloride Pattern A
Figure 16:
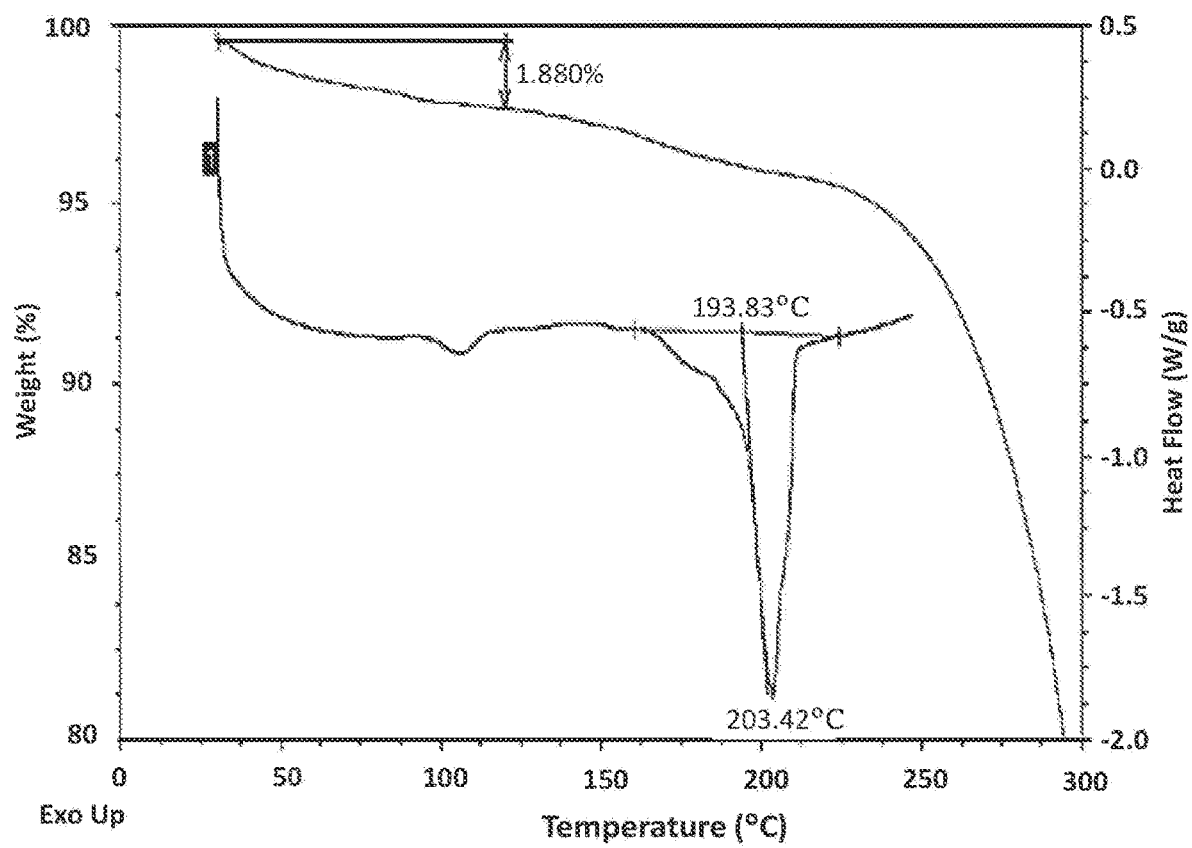
FIG. 16 illustrates a DSC/TGA thermogram for TPA023B chloride Pattern A

In one or more embodiments, a mixture comprising a crystalline polymorph of 2',6-difluoro-5'-[3-(1-hydroxy-1-methylethyl)-imidazo[1,2-b][1,2,4]triazin-7-yl]biphenyl-2-carbonitrile is described. This crystalline polymorph mixture is designated "Chloride Polymorphic Pattern A" (i.e., Chloride Pattern A) and exhibits an XRPD pattern having characteristic peak locations of at least three or all values selected from the group consisting of about: 7.0, 7.7, 8.2, 14.0, and 14.3±0.2 degrees, 2-theta, when measured using the parameters described in Table 1. Chloride Pattern A can comprise Free Base Form C. Chloride Pattern A can comprise Free Base Form F. In one or more embodiments, Chloride Polymorphic Pattern A exhibits an XRPD pattern substantially the same as the XRPD pattern shown in FIG. 15. In one or more embodiments, Chloride Polymorphic Pattern A has a melting/desolvating range of from about 150° C. to about 210° C. In one or more embodiments, Chloride Polymorphic Pattern A has a DSC thermograph substantially the same as FIG. 16. Chloride Polymorphic Pattern A can be synthesized using the method of Example 1. In one or more embodiments, pharmaceutical compositions comprising the Chloride Polymorphic Pattern A are described. In one or more embodiments, the disclosure provides purified forms of the crystalline Chloride Polymorphic Pattern A.

In one or more embodiments, still a further anhydrous, hydrated, or solvated crystalline polymorph of a salt or co-crystal of 2',6-difluoro-5'-[3-(1-hydroxy-1-methylethyl)-imidazo[1,2-b][1,2,4]triazin-7-yl]biphenyl-2-carbonitrile with a pharmaceutically acceptable acid including, but not limited to acetic acid, benzoic acid, benzene sulfonic acid, carbonic acid, camphorsulfonic acid, citric acid, fumaric acid, gluconic acid, glucuraonic acid, hydrochloric acid, hydrobromic acid, hydroiodic acid, isethionic acid, lactic acid, lauryl sulfonic acid, malic acid, maleic acid, malonic acid, methane sulfonic acid, 1-napthylenesulfonic acid, 2-napthylenesulfonic acid, oleic acid, oxalic acid, pamoic acid, phosphoric acid, succinic acid, sulfuric acid, steric acid, tartaric acid, or para-toluene sulfonic acid in any ratio is described. Further crystalline polymorphic forms are synthesized using the method of Example 19, or any other method known to one skilled in the art. In one or more embodiments, pharmaceutical compositions comprising the Polymorphic Form are described. In one or more embodiments, the disclosure provides purified forms of the crystalline polymorphic form.

In one or more embodiments, still a further anhydrous, hydrated, or solvated crystalline polymorph of 2',6-difluoro-5'-[3-(1-hydroxy-1-methylethyl)-imidazo[1,2-b][1,2,4]triazin-7-yl]biphenyl-2-carbonitrile is described. Further crystalline polymorphic forms are synthesized using the method of Example 20. In one or more embodiments, pharmaceutical compositions comprising the Polymorphic Form are described. In one or more embodiments, the disclosure provides purified forms of the crystalline polymorphic form.

Salts

In one aspect, disclosed herein are salts of 2',6-difluoro-5'-[3-(1-hydroxy-1-methylethyl)-imidazo[1,2-b][1,2,4]triazin-7-yl]biphenyl-2-carbonitrile. In some embodiments, the disclosed salts are formed with TPA023B and an acid. The acid can be an organic or inorganic acid. In some embodiments, the acid comprises one or more of: acetic acid, benzoic acid, benzene sulfonic acid, carbonic acid, camphorsulfonic acid, citric acid, fumaric acid, gluconic acid, glucuraonic acid, hydrochloric acid, hydrobromic acid, hydroiodic acid, isethionic acid, lactic acid, lauryl sulfonic acid, malic acid, maleic acid, malonic acid, methane sulfonic acid, 1-napthylenesulfonic acid, 2-napthylenesulfonic acid, oleic acid, oxalic acid, pamoic acid, phosphoric acid, succinic acid, sulfuric acid, steric acid, tartaric acid, para-toluene sulfonic acid, and the like. In some embodiments, the acid is a pharmaceutically acceptable acid. In some embodiments, the salt comprises TPA023B free base and an acid in a certain ratio, e.g., TPA023B Free Base to acid in 5:1, 4:1, 3:1, 2:1, or 1:1 ratio by mole. In some embodiments, the ratio between the TPA023B free base and the acid could be any ratio, e.g., from 1:10 to 10:1 by mole. In some embodiments, the salt is in an anhydrate form. In some embodiments, the salt is in a hydrate form. In some embodiments, the salt is in a solvate form, e.g., an ethanol, dioxane, THF, methanol, or acetone solvate. In some embodiments, the salt is free of any solvent. In some embodiments, the salt is in a crystalline form. In some embodiments, the salt is partially crystalline. In some embodiments, the salt is in an amorphous form.

In some embodiments, the salt is TPA023B phosphate. In some embodiments, the salt is TPA023B tosylate. In some embodiments, the salt is TPA023B carboxylate. In some embodiments, the salt is TPA023B gluconate. In some embodiments, the salt is TPA023B maleate. In some embodiments, the salt is TPA023 benzoate.

In one aspect, disclosed herein are mixtures comprising TPA023B or a salt thereof. In some embodiments, the disclosed mixture comprises TPA023B free base. In some embodiments, the mixture comprises one or more TPA023B free base forms, e.g., Free Base Form C, Free Base Form A, or a combination of Form C and Form A. In some embodiments, the mixture comprises a salt of TPA023B, e.g., TPA023B phosphate. In some embodiments, the mixture comprises one or more TPA023 salt forms, e.g., TPA023B phosphate Form A and TPA023B phosphate Form E. In some embodiments, the mixture comprises a TPA023B Free Base and a TPA023B salt, e.g., Free Base Form C and Phosphate Form A.

In one or more embodiments, the TPA023B salt described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the TPA023B salt described herein comprises an impurity. In some embodiments, the impurity in the TPA023B salt is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

Co-Crystals

In one aspect, disclosed herein are co-crystals of 2',6-difluoro-5'-[3-(1-hydroxy-1-methylethyl)-imidazo[1,2-b][1,2,4]triazin-7-yl]biphenyl-2-carbonitrile. In some embodiments, the disclosed co-crystals are formed with TPA023B and an acid. The acid can be an organic or inorganic acid. In some embodiments, the acid comprises one or more of: acetic acid, benzoic acid, benzene sulfonic acid, carbonic acid, camphorsulfonic acid, citric acid, fumaric acid, gluconic acid, glucuraonic acid, hydrochloric acid, hydrobromic acid, hydroiodic acid, isethionic acid, lactic acid, lauryl sulfonic acid, malic acid, maleic acid, malonic acid, methane sulfonic acid, 1-napthylenesulfonic acid, 2-napthylenesulfonic acid, oleic acid, oxalic acid, pamoic acid, phosphoric acid, succinic acid, sulfuric acid, steric acid, tartaric acid, para-toluene sulfonic acid, and the like. In some embodiments, the acid is a pharmaceutically acceptable acid. In some embodiments, the co-crystal comprises TPA023B free base and an acid in a certain ratio, e.g., TPA023B Free Base to acid in 5:1, 4:1, 3:1, 2:1, or 1:1 ratio by mole. In some embodiments, the ratio between the TPA023B free base and the acid could be any ratio, e.g., from 1:10 to 10:1 by mole. In some embodiments, the co-crystal is in an anhydrate form. In some embodiments, the co-crystal is in a hydrate form. In some embodiments, co-crystal is in a solvate form, e.g., an ethanol, dioxane, THF, methanol, ethyl acetate, or acetone solvate. In some embodiments, the co-crystal is free of any solvent. In some embodiments, the co-crystal is in a crystalline form. In some embodiments, the co-crystal is partially crystalline.

In some embodiments, the co-crystal is TPA023B phosphate. In some embodiments, the co-crystal is TPA023B gluconate. In some embodiments, the co-crystal is TPA023B maleate. In some embodiments, the co-crystal is TPA023 benzoate.

In one aspect, disclosed herein are mixtures comprising TPA023B or co-crystal thereof. In some embodiments, the disclosed mixture comprises TPA023B free base. In some embodiments, the mixture comprises one or more TPA023B free base forms, e.g., Free Base Form C, Free Base Form A, or a combination of Form C and Form A. In some embodiments, the mixture comprises a co-crystal of TPA023B, e.g., TPA023B phosphate. In some embodiments, the mixture comprises one or more TPA023 co-crystal forms. In some embodiments, the mixture comprises a TPA023B Free Base and a TPA023B co-crystal, e.g., Free Base Form C and a co-crystal of Phosphate Form A.

In one or more embodiments, the TPA023B co-crystal described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the TPA023B co-crystal described herein comprises an impurity. In some embodiments, the impurity in the TPA023B co-crystal is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

In some embodiments, the salt or co-crystal of 2',6-difluoro-5'-[3-(1-hydroxy-1-methylethyl)-imidazo[1,2-b][1,2,4]triazin-7-yl]biphenyl-2-carbonitrile with an acid can have a higher solubility than a free base form of TPA023B. For example, the solubility can be determined as described in example 15. In some embodiments, the solubility of the salt or co-crystal is at least 1.1 fold, 1.5 fold, 2 fold, 3 fold, 4 fold, 5 fold, 6 fold, 7 fold, or 8 fold higher than the solubility of Free Base Form A in simulated gastric fluid (SGF). In some embodiments, the solubility of the salt or co-crystal is at least 1.1 fold, 1.5 fold, 2 fold, 3 fold, 4 fold, 5 fold, 6 fold, 7 fold, or 8 fold higher than the solubility of Free Base Form A in Fasted-state simulated intestinal fluid (FaSSIF). In some embodiments, the solubility of the salt or co-crystal is at least 1.1 fold, 1.5 fold, 2 fold, 3 fold, 4 fold, 5 fold, 6 fold, 7 fold, or 8 fold higher than the solubility of Free Base Form A in Fed-state simulated intestinal fluid (FeSSIF) than Free Base Polymorphic Form A.

In the context of the present application, a "polymorph" is a particular crystalline arrangement or crystal "form" of a chemical compound in the solid state. A crystal form, or polymorph, of a chemical compound contains constituent molecules arranged in an orderly, repeating, three-dimensional pattern. Some chemical compounds are able to form multiple polymorphs each having a different arrangement of atoms and or molecules in their crystal structure. When the compound is a biologically active compound, such as an active pharmaceutical ingredient, the difference in crystal structures can lead to each polymorph having different chemical, physical, and biological properties. Properties which may be affected include crystal shape, density, hardness, color, chemical stability, melting point, hygroscopicity, suspensibility, dissolution rate and biological availability. As such, a specific polymorph may have properties which make it unexpectedly advantageous in a particular application relative to another polymorph of the same parent compound. In particular, the physical, chemical, and biological properties listed above can have a significant effect on the development of production methods and formulations and the quality and efficacy of active pharmaceutical ingredients. Some chemical compounds and molecular complexes (such as solvates, co-crystals, coordination compounds) can exist in multiple polymorphs, each manifesting different physical characteristics. Furthermore, less stable polymorphs may convert or partly convert into more stable polymorphs under suitable conditions. For these reasons, it is necessary to control the particular crystalline form of an active pharmaceutical ingredient when developing products which will be used for therapeutic benefit in humans or animals. It is noted that predicting whether the solid state of a compound may form one or more polymorphs is not possible and nor is it possible to predict the properties of any of these crystal forms.

In one or more embodiments, the crystalline polymorph described herein is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or at least 99.9% pure, as measured by HPLC as described herein. In some embodiment, the crystalline polymorph described herein comprises an impurity. In some embodiments, the impurity in the crystalline polymorph is at most 0.1%, at most 0.5%, at most 1%, at most 2%, at most 3%, at most 4%, at most 5%, at most 6%, at most 7%, at most 8%, at most 9%, at most 10%, at most 15%, at most 20%, at most 25%, at most 30%, at most 40%, or at most 50%, as measured by HPLC as described herein.

Assaying the solid phase for the presence of crystals may be carried out by conventional methods known in the art. For example, it is convenient and routine to use powder X-ray diffraction techniques. Other techniques which may be used include differential scanning calorimetry (DSC), thermogravimetric analysis (TGA) and Raman or Infra-red spectroscopy, NMR, gas chromatography or HPLC.

In one or more embodiments, the present disclosure provides prophylactic and/or therapeutic compositions comprising one or more of the compounds described herein dispersed in a pharmaceutically-acceptable carrier. The term "carrier" is used herein to refer to diluents, excipients, vehicles, and the like, in which the compound may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), other acceptable vehicles, and the like. Other ingredients may be included in the composition, such as adjuvants, other active agents, preservatives, buffering agents, salts, other pharmaceutically-acceptable ingredients. The composition can comprise a therapeutically effective amount of the compound dispersed in the carrier.

In one or more embodiments, the present disclosure provides methods for treating a condition or disorder in subject in need thereof, wherein the method generally comprises administering a therapeutically effective amount of one or more of the compounds described herein. As used herein, a "therapeutically effective" amount refers to the amount that will elicit the biological or medical response of a tissue, system, or subject that is being sought by a researcher or clinician, and in particular elicit some desired therapeutic or prophylactic effect against the targeted disease or condition. One of skill in the art recognizes that an amount may be considered therapeutically "effective" even if the condition is not totally eradicated or prevented, but it or its symptoms and/or effects are improved or alleviated partially in the subject. In the case of certain salts or co-crystals, it will be appreciated that formulations may be administered in amounts to provide sufficient levels of the active compound.

In some embodiments, the condition or disorder is associated with α2/α3 GABAA receptor. In some embodiments, the condition or disorder is pain, anxiety, epilepsies, muscle spasms, pruritus, itch, cognitive impairment, alcohol dependence, drug addition, schizophrenia, depression, autism, panic disorder, or generalized anxiety disorder.

In some embodiments, the condition or disorder is pain. In some embodiments, the pain is Fibromyalgia, Inflammatory pain, Neuropathic pain, Pain resulting from Peripheral Diabetic Neuropathy, Chemotherapy induced pain, pain resulting from HIV-associated Neuropathy, pain resulting from Post-herpetic neuralgia, Musculoskeletal pain, pain resulting from Rheumatoid arthritis, pain resulting from Osteoarthritis, Post-operative pain, Burn pain, Sunburn pain, or phantom limb pain. In some embodiments, the pain is an acute pain, chronic pain, neuropathic pain, nociceptive (including inflammatory) pain, somatic pain, visceral pain, or dysfunctional pain. In some embodiments, there is a brain or spinal condition underlying the pain. In some embodiments, the pain is of a neuropathic, nociceptive, and/or inflammatory nature. In some embodiments, the pain can affect either the somatic or visceral systems, or it can affect multiple systems. In some embodiments, the pain is a physiological pain. In some embodiments, the pain is an acute pain. In some embodiments, the pain is associated with a defined injury, e.g., surgery, dental work, a strain or a sprain. In some embodiments, the pain is a chronic pain. In some embodiments, the chronic pain is neuropathic pain (e.g. painful diabetic neuropathy or postherpetic neuralgia), carpal tunnel syndrome, back pain, headache, cancer pain, arthritic pain, or chronic post-surgical pain. In some embodiments, the pain is a chronic painful condition affecting any system. In some embodiments, the neuropathic pain is associated with a disease or trauma such as peripheral neuropathy, post herpetic neuralgia, diabetic neuropathy, trigeminal neuralgia, cancer neuropathy, HIV neuropathy, phantom limb pain, back pain, carpal tunnel syndrome, central post-stroke pain and pain associated with chronic alcoholism, hypothyroidism, uremia, spinal cord injury, multiple sclerosis, Parkinson's disease, epilepsy and vitamin deficiency. In some embodiments, the condition or disorder is fibromyalgia or chronic regional pain syndrome. In some embodiments, the pain is a moderate to severe acute nociceptive pain, which can be associated with post-operative pain, posttraumatic pain cancer pain, back pain, pain associated with gout, or pains from strains, sprains, burns, myocardial infarction, or acute pancreatitis. In some embodiments, the cancer pain is a chronic pain, e.g., tumor related bone pain, headache, facial pain, or visceral pain. In some embodiments, the cancer pain is a pain associated with cancer therapy, e.g., the pain in response to chemotherapy, immunotherapy, hormonal therapy or radiotherapy. In some embodiments, the pain is a back pain. In some embodiments, the pain is associated with arthritis such as rheumatoid arthritis.

In some embodiments, the condition or disorder is Drug addiction or Alcohol dependence. In some embodiments, the condition or disorder is panic disorder, generalized anxiety disorder, anxiety, or schizophrenia. in some embodiments, the condition or disorder is a stress disorder, e.g., post-traumatic stress disorder, acute stress disorder, or substance-induced stress disorder. In some embodiments, the condition or disorder is a phobia, such as agoraphobia, social phobia, or animal phobias. In some embodiments, the condition or disorder is an obsessive compulsive disorder. In some embodiments, the anxiety is a separation anxiety or a childhood anxiety disorder.

In some embodiments, the condition or disorder is itch, e.g., chronic or acute itch. In some embodiments, the condition or disorder is Chronic Itch, Neurogenic itch, Uremic Pruritus, Neurodermatitis, Atopic Dermatitis, Notalgia Paresthetica, Prurigo Nodularis, Psoriasis, Psychogenic itch, or Aquagenic Itch. In some embodiments, the itch is Pruriceptive itch. Pruriceptive itch can be caused by an allergic reaction, inflammation, dryness or other skin damage. Pruriceptive itch can be associated with atopic dermatitis (eczema), urticaria (hives), psoriasis, drug reactions, mites, or dry skin. In some embodiments, the itch is neuropathic itch. Neuropathic itch can be caused by damage to the nervous system and is often accompanied by sensations of numbness and tingling. Neuropathic itch can be seen after shingles, after stroke or burn injury, and in notalgia parasthetica (an area of itchy skin, usually on the back). Neurogenic itch can be associated with chronic liver and kidney disease in response to opioid neuropeptides. Neuropathic itch psychogenic itch. Psychogenic itch can be induced in response to the chemicals serotonin or norepinephrine, which influence stress, depression and delusional parasitosis (a false belief of parasite infestation). In some embodiments, the condition or disorder is Cholestatic Pruritus, Uremic Pruritus, Neurodermatitis, Notalgia Paresthetica, Atopic Dermatitis, Contact Dermatitis, Prurigo Nodularis, Psoriasis, Bug bites, Parasites, Fungal infection, Aquagenic Itch, Uticaria, Allergic itch, or Delusional parasitosis.

In some embodiments, the condition or disorder is chronic cough or Irritable Bowel Syndrome. In some embodiments, the condition or disorder is epilepsy. In some embodiments, the epilepsy is autosomal dominant nocturnal frontal lobe epilepsy (ADNFLE), Focal epilepsy, Generalized epilepsy, Dravet Syndrome, Childhood absence epilepsy (CEA), Juvenile absence epilepsy, Juvenile myoclonic epilepsy (JME), West Syndrome, Lennox-Gastaut syndrome (LGS), Sunflower Syndrome, Staticus epilepticus, Nerve agent induced seizures, Tremors from alcohol withdrawal, Traumatic Brain Injury, Tuberous Sclerosis Complex, Doose Syndrome, Rasmussen's Syndrome, Early myoclonic encephalopathy, Malignant migrating partial seizures of infancy, Epilepsy with continuous spike and waves during slow wave sleep, Landau-Kleffner syndrome, Benign epilepsy with centrotemporal spikes, Benign familial neonatal infantile seizures, Benign centrotemporal lobe epilepsy of childhood, Benign occipital epilepsy of childhood (BOEC), Cortical dysplasia focal epilepsy syndrome, Generalized epilepsy with febrile seizure plus (GEFS+), Myoclonic atonic epilepsy, Malignant migrating partial seizures of infancy, Ohtahara syndrome (a.k.a. early infantile epileptic encephalopathy), primary reading epilepsy, symptomatic localization-related epilepsies, temporal lobe epilepsy (TLE), Rasmussen's encephalitis, progressive myoclonic epilepsy, or Partial epilepsy and febrile seizures plus. In some embodiments, the condition or disorder is spasticity (such as Post-stroke spasticity, or generalized and focal spasticity), Muscle spasms, essential tremor, dystonia, or premature ejaculation. In some embodiments, the condition or disorder is autism. In some embodiments, the condition or disorder is autism resulting from an SCN2a mutation, fragile X syndrome, or any form of autism related to the dysfunction of an ion-channel. In some embodiments, the condition or disorder is depressive disorder (such as depression), bipolar disorders, or cyclothymia. In some embodiments, the condition or disorder is schizophrenia such as schizophrenia of the paranoid type, disorganized type, catatonic type, undifferentiated type, residual type, post-schizophrenic depression and simple schizophrenia.

In some embodiments, the compounds and compositions described herein can be used as an antiemetic agents, e.g., for chemotherapy or radiation induced emesis, post-operative nausea and vomiting, or motion sickness. In some embodiments, the compounds and compositions described herein can be used as a cognition-enhancing agent.

In some embodiments, the subject is afflicted with or suffering from a condition (e.g., infection, disease, or disorder) before the compounds are administered, wherein methods described herein are useful for treating the condition and/or ameliorating the effects of the condition. In one or more embodiments, the methods are useful for reversing progression of the disease or condition. In other embodiments, the subject is free of a given condition before administering the compound, wherein the methods described herein are useful for preventing the occurrence or incidence of the condition and/or preventing the observable effects of the condition. The disclosed embodiments can be formulated for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally or orally. The compounds or compositions can also be administered through the skin via a transdermal patch or microneedles. Suspensions, powders, tablets, gel caps, etc., are contemplated herein.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject. A kit comprising the compound(s) is also disclosed herein. The kit further comprises instructions for administering the compound to a subject. The compound(s) can be provided as part of a dosage unit, already dispersed in a pharmaceutically-acceptable carrier, or it can be provided separately from the carrier. The kit can further comprise instructions for preparing the compounds for administration to a subject, including for example, instructions for dispersing the compounds in a suitable carrier.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study.

In still another embodiment, described herein are methods of preparing a crystalline form of a compound described herein. The methods generally comprise one or more of the following techniques: slurrying the compound for a period of time in one or more solvents, with or without heating; dissolving the compound in a one or more solvents with or without heating and then removing some or all of the solvent(s) through a method such as evaporation or distillation; dissolving the compound in one or more solvents and adding an anti-solvent, combination of antisolvents, or a mixture of solvent and antisolvent; dissolving a compound in one or more solvents with or without heating and then allowing the solution to cool, or actively cooling any solution; heating a compound in the absence of solvent; heating a compound under atmospheric or reduced pressure until it sublimates and collecting it on a cooled surface; melting a solid and allowing it to cool; exposing the compound to water vapor or the vapor of a solvent; adding small amounts of seed material; any other method known to one skilled in the art; and combinations of any or all of the above processes.

In still another embodiment, the disclosure is concerned with use of a compound according to the various embodiments described herein to prepare a therapeutic or prophylactic medicament for the treatment or prevention of a disease or condition treatable by α2/α3 GABAA positive allosteric modulators, as well as disorders treatable with non-selective GABAA positive allosteric modulators in both animals and humans.

Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments but is not necessarily included. Thus, the present disclosure encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

As used herein, the term "about" when used in association with a measurement, or used to modify a value, a unit, a constant, or a range of values, refers to variations of +/−3%.

The term "substantially the same," as used herein to define a figure is intended to mean that the figure is considered the same as a reference figure by a skilled artisan in view of deviations acceptable in the art. Such deviations may be caused by factors related to instruments, operation conditions and human factors, etc., known in the art. For example, one skilled in the art can appreciate that the endotherm onset and peak temperatures as measured by differential scanning calorimetry (DSC) may vary significantly from experiment to experiment. In some embodiments, when positions of characteristic peaks of two figures do not vary more than +/−5%, +/−4%, +/−3%, +/−2%, or +/−1%, it is deemed that the two figures are substantially the same. For example, one skilled in the art can readily identify whether two X-ray diffraction patterns or two DSC thermograms are substantially the same. In some embodiments, when characteristic peaks of two X-ray diffraction patterns do not vary more than ±0.3° 2-Theta, ±0.2° 2-Theta or ±0.1° 2-Theta, it is deemed that the X-ray diffraction patterns are substantially the same.

The present description also uses numerical ranges to quantify certain parameters relating to various embodiments of the disclosure. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the disclosure. It is to be understood, however, that these examples are provided by way of illustration and nothing therein should be taken as a limitation upon the overall scope of the disclosure.

Example 1

Salt Screening

Salt screening via reaction crystallization was preliminarily conducted using five acids in four solvents or solvent mixtures. For hydrochloric acid, sulfuric acid, phosphoric acid, and methanesulfonic acid, about 20 mg of TPA023B was stirred in about 0.5 mL of solvent and about 1.1 molar equivalents of the corresponding acid solutions were added. For p-toluenesulfonic acid, about 20 mg of TPA023B and about 1.1 molar equivalents of the corresponding acid were stirred in about 0.5 mL of each solvent. For controls, about 20 mg of TPA023B was stirred in about 0.5 mL of the corresponding solvent. The resulting mixture was heated to about 50° C. with continuous stirring for about 4 hrs and slowly cooled to about 20-25° C. overnight.

Because TPA023B possesses a tertiary alcohol that is also alpha to an aromatic ring it may be prone to degradation by elimination under acidic conditions. HPLC analysis was conducted on the acetone samples to determine the extent of degradation that occurred, if any. The results showed that TPA023B with $H_3PO_4$ in acetone had lower degradation than the other acids.

TABLE 2

HPLC analysis

| Sample | Purity (%) |
|---|---|
| TPA023B control in acetone | 99.33 |
| TPA023B with H3PO4 in acetone | 98.88 |
| TPA023B with methane sulfonic acid in acetone | 98.71 |
| TPA023B with p-toluene sulfonic acid in acetone | 98.65 |
| TPA023B with HCl in acetone | 98.61 |
| TPA023B with H2SO4 in acetone | 98.33 |

Figure 25:
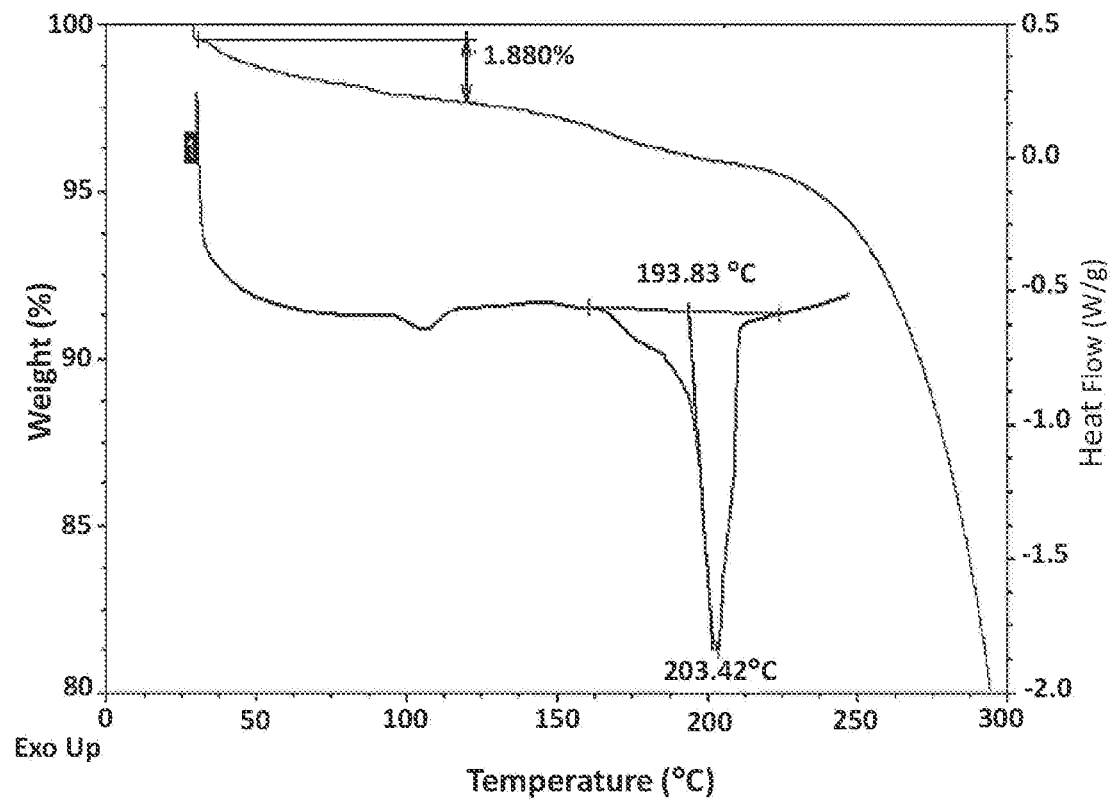
FIG. 25 illustrates the TGA and DSC results of TPA023B HCl salt in Acetone system (a mixture comprising TPA023B Free Base Form C and TPA023B Chloride Pattern A)

For any experiment which produced an observable solid, the solid was isolated by centrifugation (about 14,000 rpm for about 5 minutes) and analyzed by XRPD. For clear solutions, solids were produced via evaporation at 35° C. by drying in vacuo and checked by XRPD. TGA and DSC characterization data was collected for any solid that demonstrated novel crystallinity by XRPD. The results are shown in Table 3 and the XRPD patterns are shown in FIGS. 20 to 24. The DSC/TGA resulting solid from the "Hydrochloric Acid in Acetone" experiment is provided in FIG. 25. The DSC/TGA resulting solid from the "Phosphoric Acid in Acetonitrile" experiment is provided in FIG. 26.

TABLE 3

Results of Example 1.

| | Solvent System | | | |
|---|---|---|---|---|
| Acid | Acetone | Ethyl Acetate | Acetonitrile | 95% IPA/H2O |
| Hydrochloric Acid | Mixture: Free Base Polymorphic Form C and Chloride Polymorphic Pattern A | Free Base Polymorphic Form A | Free Base Polymorphic Form A | Free Base Polymorphic Form A |
| Sulfuric Acid | Amorphous | Amorphous | Amorphous | Free Base Polymorphic Form A |
| Phosphoric acid | Phosphate Polymorphic Form A | Phosphate Polymorphic Form A | Phosphate Polymorphic Form A | Free Base Polymorphic Form A |
| p-toluene sulfonic acid | Amorphous | Amorphous | Amorphous | Free Base Polymorphic Form A |
| Methane sulfonic acid | Amorphous | Amorphous | Amorphous | Free Base Polymorphic Form A |
| API control | Free Base Polymorphic Form C | Free Base Polymorphic Form A | Free Base Polymorphic Form A | Free Base Polymorphic Form A |

The phosphate salt was found to readily form a stable new crystalline form. In addition, a trace of a new crystalline form was observed that may be a hydrochloride salt or a new polymorph of the free base. It was labeled Chloride Polymorphic Pattern A. Given the pKa of TPA023B (about 2.19) and its highly planar aromatic structure of TPA023B, it is unexpected that out of the strong acids tested, only phosphoric acid readily formed highly crystalline solids with properties suitable for manufacture and use in pharmaceutical preparations, especially given that the pKa of TPA023B and Phosphoric Acid are so similar. The relative stability of TPA023B with phosphoric acid, as compared with other stronger acids, provides a significant benefit to the manufacturability of the phosphate salt or co-crystal that could not have been predicted beforehand. It is highly beneficial that the salt or co-crystal formation be the final particle forming step, because any additional purification steps after this stage add significantly to the cost of goods. Therefore, the reduced impurity formation afforded by the phosphate salt or co-crystal reduces the risk of needing additional purification and offers an advantage over other counterions.

Example 2

Crystallization Screening on Amorphous Salts of TPA023B

Additional attempts to find crystalline salt forms of TPA023B were made. The amorphous TPA023B salts formed in Example 1, and about 0.5 ml of the corresponding solvent shown (Table 4) were heated to about 50° C. with continuous stirring for about 2 days. Only in the case of p-toluene sulfonate in toluene, a crystalline solid was obtained. In all other cases, an amorphous solid was obtained. This salt was labeled Tosylate Polymorphic Form A.

TABLE 4

Results from Example 2

| | Solvent System | | |
|---|---|---|---|
| Acid | Toluene | MTBE | Heptane |
| Sulfuric acid | Amorphous | Amorphous | Amorphous |
| p-toluene sulfonic acid | Tosylate Polymorphic Form A | Amorphous | Amorphous |
| Methanesulfonic acid | Amorphous | Amorphous | Amorphous |

Example 3

Accelerated Stability Testing of Phosphate Polymorphic Form A and Free Base Polymorphic Form A The stability of Phosphate Polymorphic Form A and Free Base Polymorphic Form A were evaluated under accelerated conditions.

TABLE 5

One (1) Week Accelerated Stability Testing

| Material | Storage Conditions | Timepoint | Assay* (%) | Purity (%) |
|---|---|---|---|---|
| Phosphate Polymorphic Form A | — | Initial | 104.60 | 98.91 |
| | 80° C. (open) | 1 week | 95.99 | 98.94 |
| | 40° C./75% RH (open) | 1 week | 97.12 | 99.02 |
| | Light | ~50 h | 95.25 | 97.55 |
| Free Base Polymorphic Form A | — | Initial | 105.51 | 98.72 |
| | 80° C. (open) | 1 week | 101.60 | 98.62 |
| | 40° C./75% RH (open) | 1 week | 102.35 | 98.64 |
| | Light | ~50 h | 104.28 | 98.60 |

*Assay criterion: 95%-105%

TABLE 6

Details of Photostability Chamber

| | Conditions | Time |
|---|---|---|
| VIS (light) | 30 Kilolux | 43 hrs |
| VIS (UV) | 200 watt | 7.92 hrs |

Example 4

The hygroscopicity of Phosphate Polymorph Form A was measured by Dynamic vapor sorption (DVS). A reversible mass increase of about 1.08% was observed. After DVS, XRPD confirmed that the crystalline form was retained (see FIG. 19).

Example 5

Figure 1:
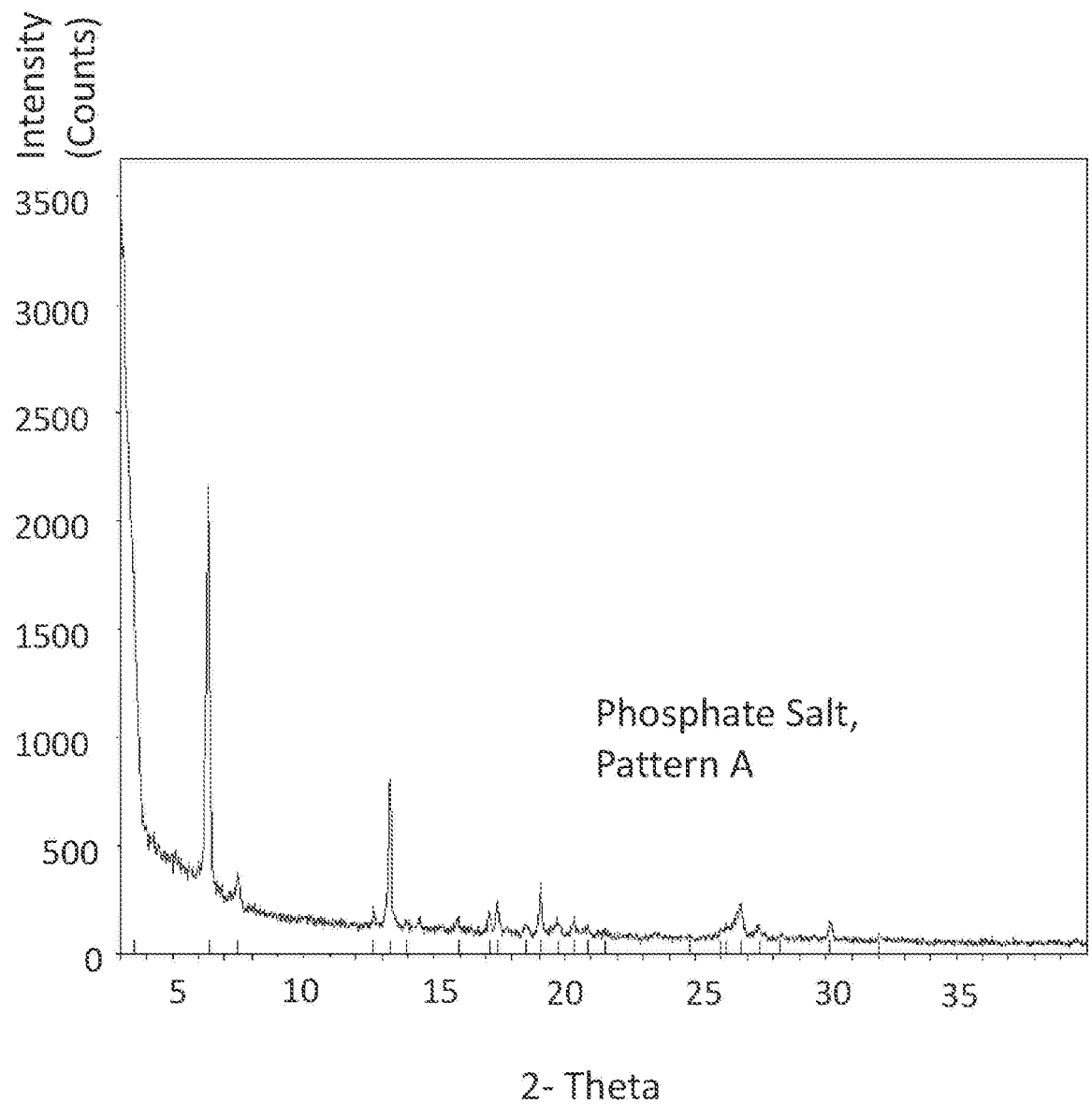
FIG. 1 illustrates an XRPD pattern for TPA023B phosphate Form A

Preparation of Polymorphic Form A of the Salt or Co-Crystal of 2',6-difluoro-5'-[3-(1-hydroxy-1 methylethyl)-imidazo[1,2-b][1,2,4]triazin-7-yl]biphenyl-2-carbonitrile with Phosphoric Acid Phosphate Polymorphic Form A A 0.5 M solution of phosphoric acid in acetonitrile (44 mL, 22 mmol, 1.1 Eq) was added to 2',6-difluoro-5'-[3-(1-hydroxy-1-methylethyl)-imidazo[1,2-b][1,2,4]triazin-7-yl]biphenyl-2-carbonitrile (8.0 g, 20 mmol, 1.0 Eq) in acetonitrile (200 mL) and stirred at about 50° C. for about 4 hrs. The resulting mixture was cooled slowly to room temperature overnight. The resulting solid was collected and dried to provide Phosphate Polymorphic Form A (9.2 g, 92% yield). An XRPD pattern of TPA023B Phosphate Polymorphic Form A is illustrated in FIG. 1. A DSC/TGA thermogram, and an NMR spectrum of TPA023B Phosphate Polymorphic Form A are illustrated in FIGS. 2A, and 2B, respectively. Additional DSC/TGA thermogram of TPA023B Phosphate Polymorphic Form A is illustrated in FIG. 2C. The Phosphate Polymorphic Form A samples for FIGS. 1, 2A, and 2B are taken from the same batch; the sample for FIG. 2C is taken from a different batch.

Example 6

Preparation of Polymorphic Pattern B of the Salt or Co-Crystal of 2',6-difluoro-5'-[3-(1-hydroxy-1-methylethyl)-imidazo[1,2-b][1,2,4]triazin-7-yl]biphenyl-2-carbonitrile with Phosphoric Acid Phosphate Polymorphic Pattern B The salt or cocrystal of 2',6-difluoro-5'-[3-(1-hydroxy-1-methylethyl)-imidazo[1,2-b][1,2,4]triazin-7-yl]biphenyl-2-carbonitrile with phosphoric acid (20.9 mg, 0.041 mmol) was stirred for about 3 days in methanol (0.2 mL) at about 20° C. to 25° C. The resulting solid was separated by centrifuge (5 min at 14000 rpm) and dried overnight in a vacuum oven heated to about 30° C. to provide Phosphate Polymorphic Pattern B. TPA023B Phosphate Pattern B likely comprises a mixture of Phosphate Form A and Phosphate Form G.

Figure 3:
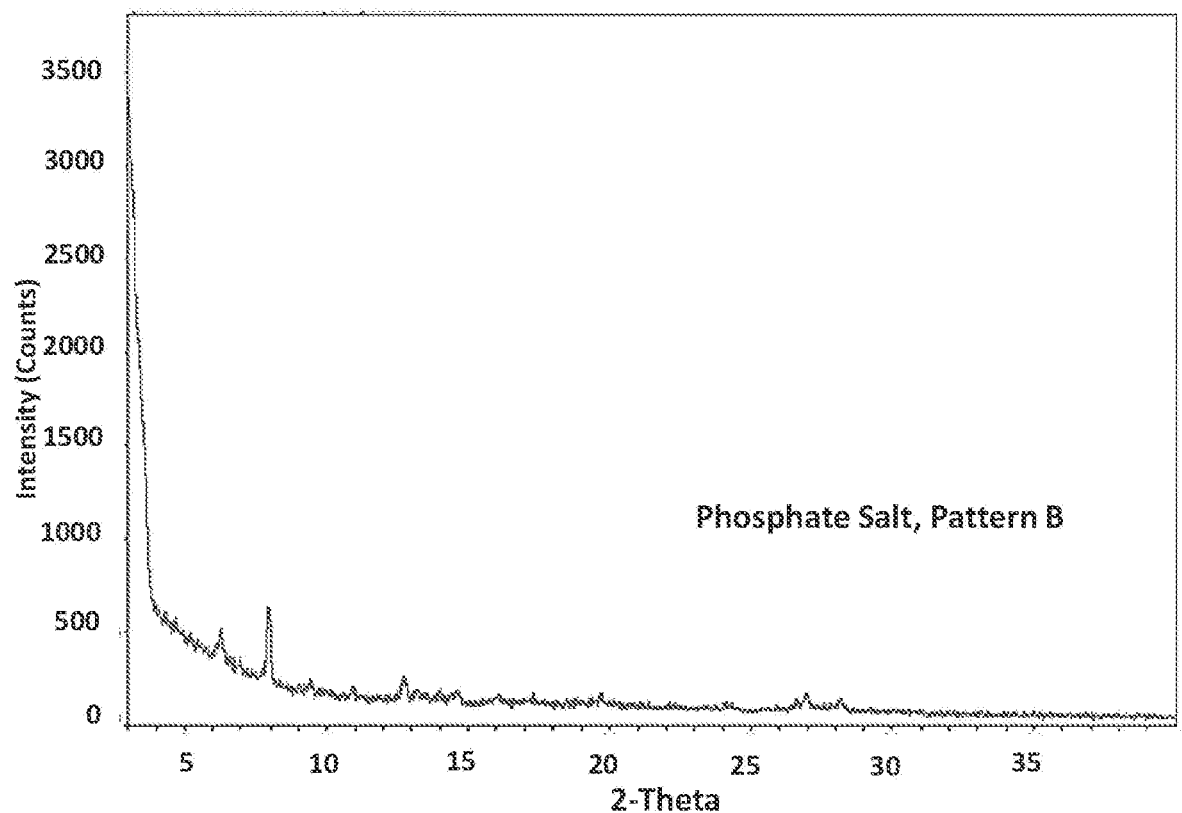
FIG. 3 illustrates an XRPD pattern for TPA023B Phosphate Pattern B
Figure 4:
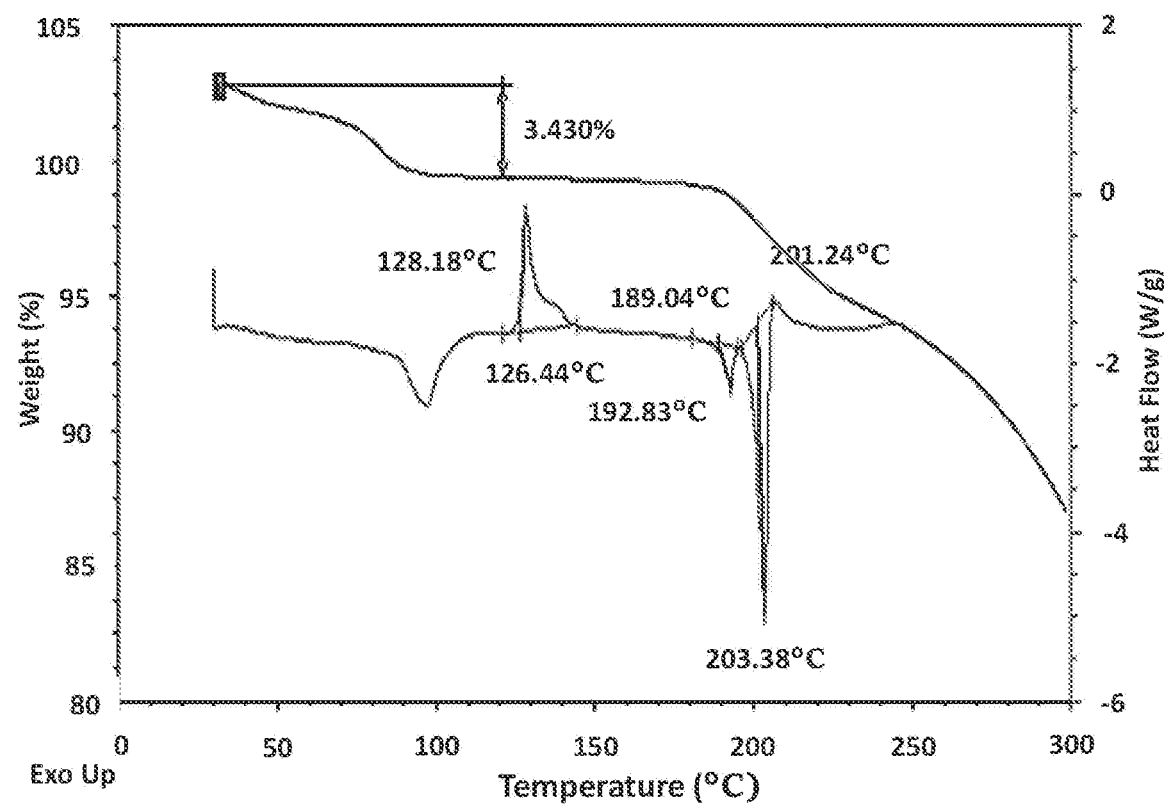
FIG. 4 illustrates an DSC/TGA thermogram for TPA023B phosphate Pattern B

An XRPD pattern of TPA023B Phosphate Polymorphic Pattern B is illustrated in FIG. 3. A DSC/TGA thermogram of TPA023B Phosphate Polymorphic Pattern B is illustrated in FIG. 4. As shown in FIG. 4, the DSC trace showed two endothermic peaks with onset temperatures of 189° C. (10.49 J/g) and 201° C. (76.46 J/g). The TGA result showed that the original form exhibits a three-step weight loss of 3.428% from 30° C. to 120° C., which could be attributed to removal of residual solvent.

Example 7

Preparation of Polymorphic Free Base Form C

The salt or cocrystal of 2',6-difluoro-5'-[3-(1-hydroxy-1-methylethyl)-imidazo[1,2-b][1,2,4]triazin-7-yl]biphenyl-2-carbonitrile with phosphoric acid (100 mg, 0.204 mmol) was transferred into a vial containing methanol (about 1.0 mL). The mixture was heated to about 60° C., stirred for about 4 hours, and then cooled to 20° C. to 25° C. This heat and cool cycle was repeated twice more. The resulting solid was collected by centrifugation and dried at about 30° C. in a vacuum oven to provide Free Base Form C.

Figure 5:
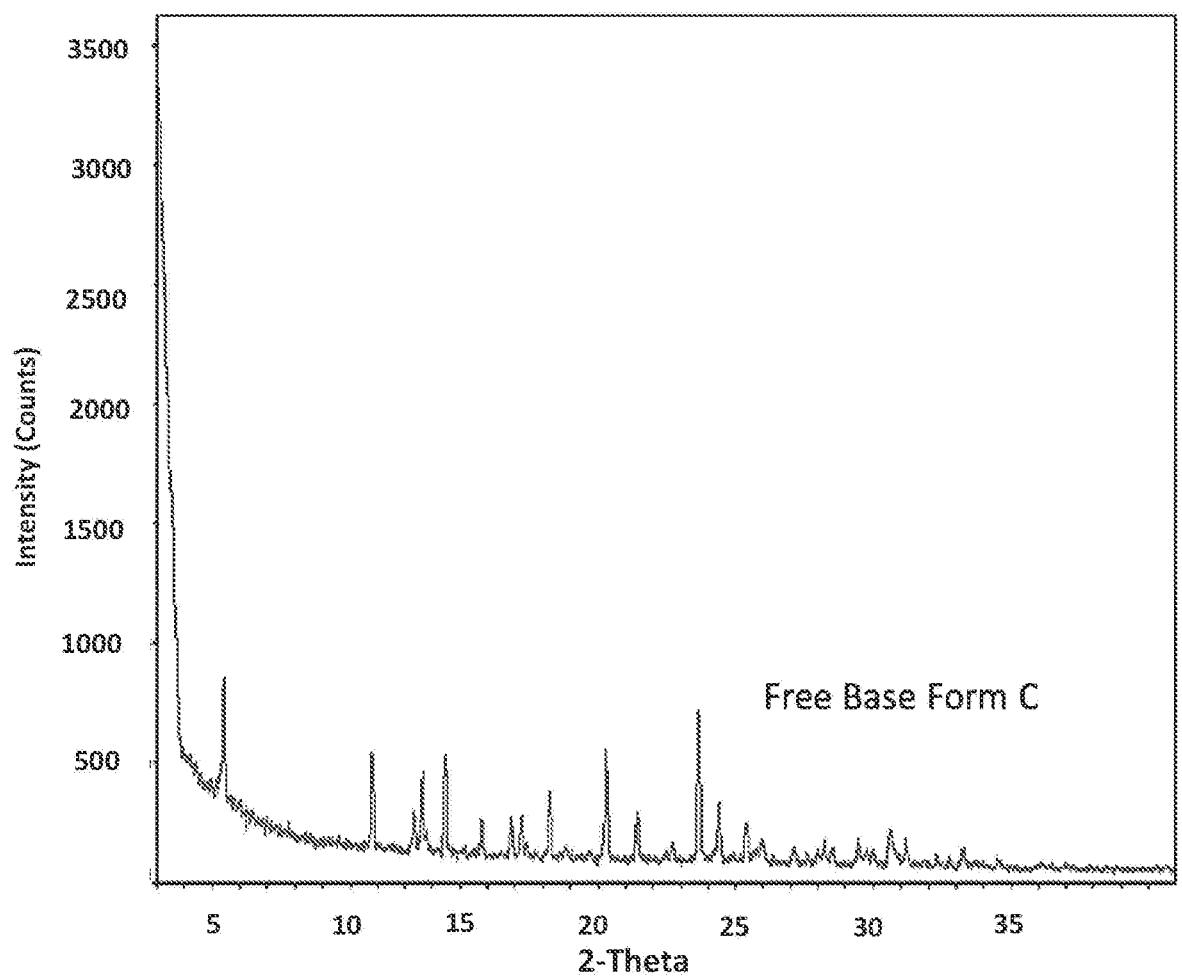
FIG. 5 illustrates an XRPD pattern for TPA023B free base Form C
Figure 6:
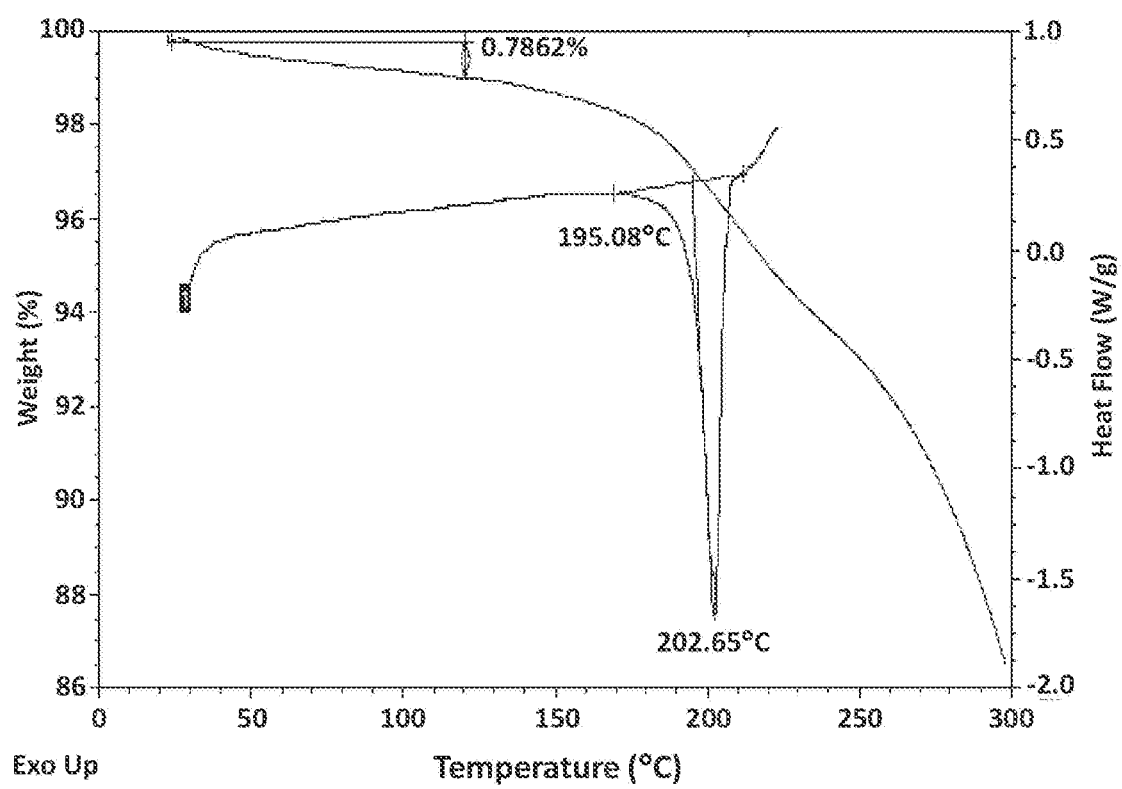
FIG. 6 illustrates a DSC/TGA thermogram for TPA023B free base Form C

An XRPD pattern of TPA023B Free Base Polymorphic Form C is illustrated in FIG. 5. A DSC/TGA thermogram of TPA023B Free Base Polymorphic Form C is illustrated in FIG. 6. As shown in FIG. 6, the DSC trace showed one endothermic peak with an onset temperature of 195° C. (96.04 J/g). Its TGA trace showed that a three-step weight loss of 0.7862% from 30° C. to 120° C., which could be attributed to removal of residual solvent.

Example 8

Figure 7:
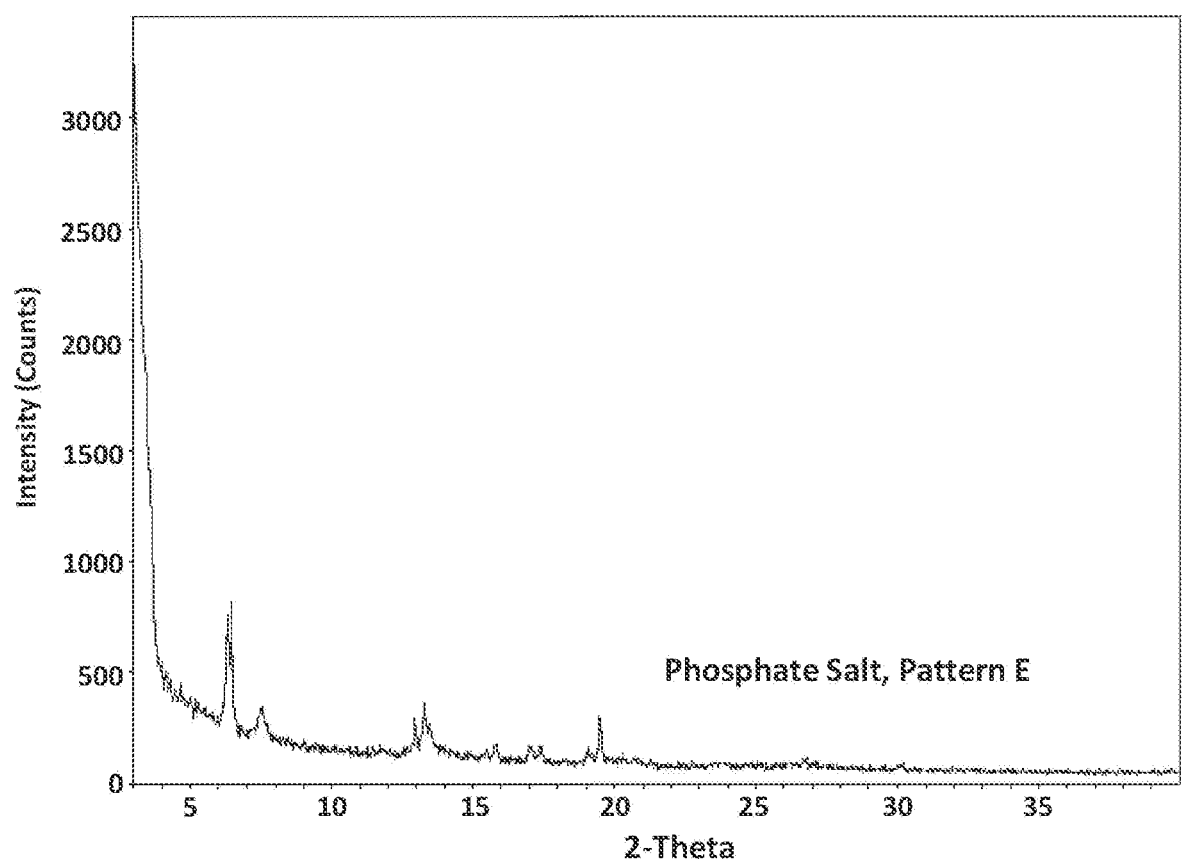
FIG. 7 illustrates an XRPD pattern for TPA023B phosphate mixture comprising TPA023B Phosphate Form A
Figure 8:
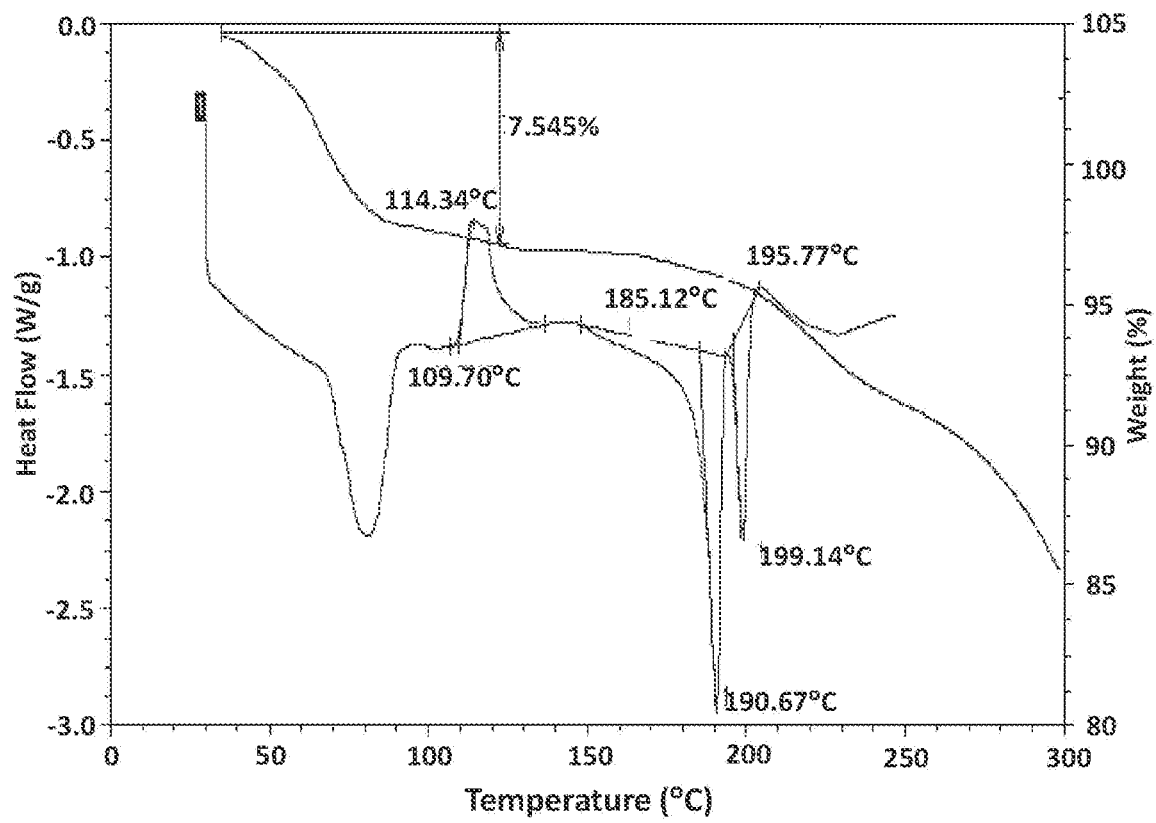
FIG. 8 illustrates a DSC/TGA thermogram for TPA023B phosphate mixture comprising TPA023B Phosphate Form A

Preparation of Polymorphic Pattern E of the Salt or Cocrystal of 2',6-difluoro-5'-[3-(1-hydroxy-1-methylethyl)-imidazo[1,2-b][1,2,4]triazin-7-yl]biphenyl-2-carbonitrile with Phosphoric Acid Phosphate Polymorphic Pattern E Water (about 1.0 mL) was added dropwise to a vial containing 0.2 ml of a 100 mg/ml stock solution of the salt of 2',6-difluoro-5'-[3-(1-hydroxy-1-methylethyl)-imidazo[1, 2-b][1,2,4]triazin-7-yl]biphenyl-2-carbonitrile with phosphoric acid (150 mg, 0.307 mmol) in dimethyl sulfoxide until precipitate formed. The precipitate was collected by centrifuge and dried overnight in a ~30° C. vacuum oven to provide Phosphate Polymorphic Pattern E. An XRPD pattern of TPA023B Phosphate Polymorphic Pattern E is illustrated in FIG. 7. A DSC/TGA thermogram of TPA023B Phosphate Polymorphic Pattern E is illustrated in FIG. 8. As shown in FIG. 8, the DSC pattern showed two endothermic peaks with onset temperatures of 185° C. (63.40 J/g) and 196° C. (19.60 J/g). It is believed that TPA023B Phosphate Pattern E likely comprises a mixture that comprises Phosphate Form A and another form.

Example 9

Preparation of Polymorphic Form A of the Salt of 2',6-difluoro-5'-[3-(1-hydroxy-1-methylethyl)-imidazo[1,2-b][1,2,4]triazin-7-yl]biphenyl-2-carbonitrile with 4-methylbenzene Sulfonic Acid Tosylate Polymorphic Form A 2',6-difluoro-5'-[3-(1-hydroxy-1-methylethyl)-imidazo[1,2-b][1,2,4]triazin-7-yl]biphenyl-2-carbonitrile (100 mg, 0.256 mmol) and toluene (1.5 ml) were heated to 110° C. and stirred vigorously for 15 min. The mixture was cooled to 95° C. and 1,4-dioxane (0.8 mL) was added slowly. A 0.5 M solution of 4-methylbenzene sulfonic acid in 1,4-dioxane (0.05 mL, 0.1 equivalents) was added, followed by ~1 mg of seed material. Additional 0.5M 4-methylbenzene sulfonic acid in 1,4-dioxane solution (0.49 mL, 0.95 Eq) was added over 30 min, and the resulting mixture was stirred at 95° C. for 30 min. The mixture was then allowed to cool to room temperature and the solids were collected by centrifugation (1000 rpm for 5 minutes). The isolated solid was washed with n-heptane and dried in a ~30° C. vacuum oven for 4 hrs to provide Tosylate Polymorphic Form A. An XRPD pattern of TPA023B tosylate Form A is provided in FIG. 17A, and an NMR spectrum of TPA023B tosylate is provided in FIG. 17B. TPA023B tosylate displays birefringence under polarized light.

Example 10

Figure 10B:
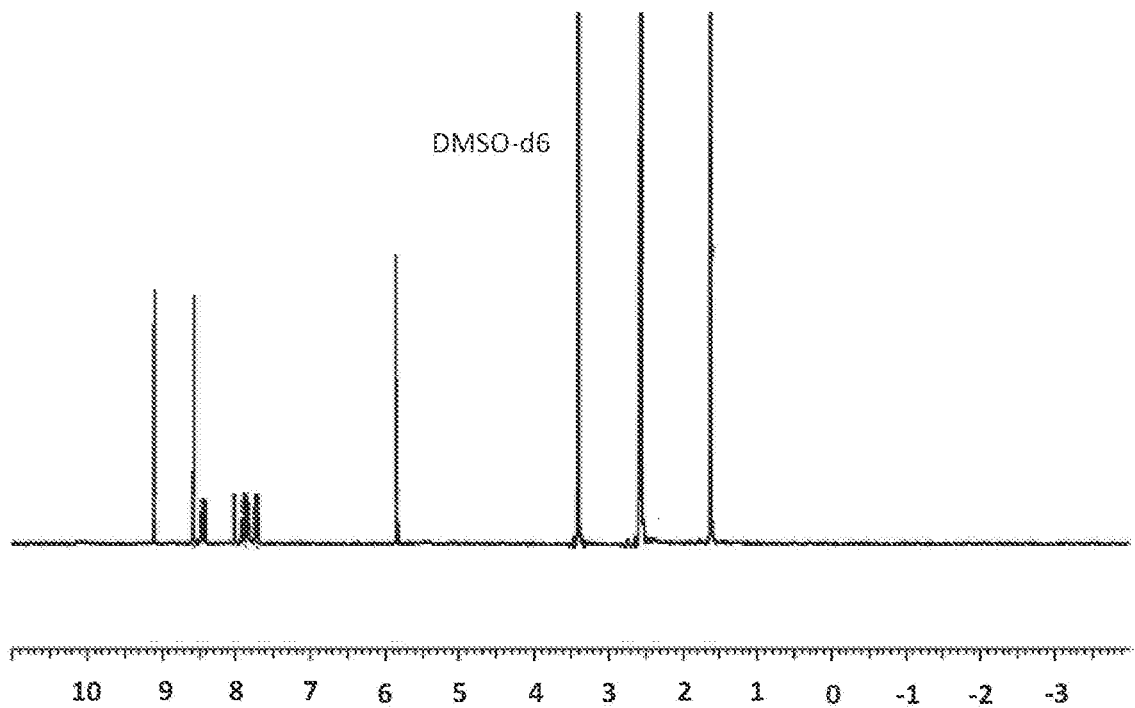

Preparation of Polymorphic Form A of 2',6-difluoro-5'-[3-(1-hydroxy-1-methylethyl)-imidazo[1,2-b][1,2,4]triazin-7-yl]biphenyl-2-carbonitrile Free Base Polymorphic Form A 2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing acetonitrile (0.5 ml). The mixture was mixed at about 20° C. to 25° C. for about 4 hours, then heated to about 50° C. overnight. The slurry was allowed to cool to ambient temperature. The resulting solids were isolated by centrifugation at about 14000 rpm for 5 minutes and dried in a vacuum oven at ~35° C. to provide Free Base Polymorphic Form A. An XRPD pattern of TPA023B Free Base Polymorphic Form A is provided in FIG. 9. A DSC/TGA thermogram and an NMR spectrum of TPA023B Free Base Polymorphic Form A are provided in FIGS. 10A and 10B, respectively.

Example 11

Preparation of Polymorphic Form B of 2',6-difluoro-5'-[3-(1-hydroxy-1-methylethyl)-imidazo[1,2-b][1,2,4]triazin-7-yl]biphenyl-2-carbonitrile Free Base Polymorphic Form B 2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing ethanol (0.5 ml). The mixture was mixed at about 20° C. to 25° C. for about 4 hours, then heated to ~50° C. overnight. If the final mixture was clear solution, the solution would be evaporated by vacuum drying oven at ~35° C. and the resulted solid was checked by XRPD. The resulting solid was isolated by centrifugation at about 14,000 rpm for ~5 minutes and dried by in a ~35° C. vacuum oven to provide Free Base Polymorphic Form B. Preliminary analysis suggests this is an Ethanol Solvate polymorph, which expunges Pd, and is a key intermediate.

Example 12

Preparation of Polymorphic Form C of 2',6-difluoro-5'-[3-(1-hydroxy-1-methylethyl)-imidazo[1,2-b][1,2,4]triazin-7-yl]biphenyl-2-carbonitrile Free Base Polymorphic Form C 2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing dichloromethane (0.5 ml) and the vial was sealed. The mixture was stirred at about 20° C. to ~25° C. for about 4 hours, then heated to ~50° C. overnight. The resulting slurry was allowed to cool to ambient, and the resulting solids were isolated by centrifugation at 14000 rpm for ~5 minutes and dried by in a ~35° C. vacuum oven to provide Free Base Polymorphic Form C.

Example 13

Preparation of Polymorphic Pattern D of 2',6-difluoro-5'-[3-(1-hydroxy-1-methylethyl)-imidazo[1,2-b][1,2,4]triazin-7-yl]biphenyl-2-carbonitrile Free Base Polymorphic Pattern D 2',6-difluoro-5'-[3-(1-hydroxy-1-methylethyl)-imidazo[1,2-b][1,2,4]triazin-7-yl]biphenyl-2-carbonitrile (25 mg, 0.064 mmol) was added to a vial containing 1,4-dioxane (0.5 ml) and the vial was sealed. The mixture was stirred at about 20° C. to 25° C. for ~4 hours, then heated to ~50° C. overnight. The resulting solution was cooled to about 20° C. to 25° C., and evaporated to dryness in a ~35° C. vacuum oven to provide Free Base Polymorphic Pattern D. Free Base Pattern D likely comprises a mixture that comprises Free Base Form A and a new form that may be a dioxane solvate.

Example 14

Competitive Slurry Experiment

Determining which polymorphic form is more thermodynamically stable may be experimentally determined by conventional methods known in the art. For example, a competitive slurry experiment in which a 1:1 mixture of polymorphic forms is stirred for a period of time in a solvent in which both polymorphic forms are partly soluble may be conducted. It is accepted by those skilled in the art that if the 1:1 mixture converts entirely to one polymorphic form, that form that results is more thermodynamically stable of the two, while the other form is metastable.

Example 15

Solubility of Free Base Polymorphic Form A and Phosphate Polymorphic Form A

About 2 mg of test article was added to a 1.5 mL vials which contained ~1.0 mL of one medium listed in Table 7 and Table 8, which was then sealed. The mixtures were stirred at ~20-25° C. for ~24 hours. After that, the mixture was filtered by 0.45 μm filter membrane and then the supernatant was analyzed by HPLC. The results were showed in the Table 7 and Table 8. The results indicated that Phosphate Polymorphic Form A had higher solubility in simulated gastric fluid (SGF), Fasted-state simulated intestinal fluid (FaSSIF) and Fed-state simulated intestinal fluid (FeSSIF) than Free Base Polymorphic Form A.

| Media | Target Conc. (mg/mL) | Measured Conc. (μg/mL) | Initial pH | pH value of supernatant |
|---|---|---|---|---|
| Purified water | 2 | 0.14 | 7.02 | 8.73 |
| pH 1.2 Hydrochloric Acid Buffer (50 mM) | | 9.77 | 1.17 | 1.12 |
| pH 3.0 citrate buffer (100 mM) | | <LOQ | 3.05 | 3.00 |
| pH 4.5 citrate buffer (100 mM) | | <LOQ | 4.44 | 4.45 |
| pH 7.4 PBS (50 mM) | | <LOQ | 7.40 | 7.42 |
| pH 9.0 USP Buffer (50 mM) | | <LOQ | 8.94 | 8.98 |
| SGF | | 1.38 | 1.80 | 1.86 |
| FaSSIF | | 2.11 | 6.51 | 6.50 |
| FeSSIF | | 9.63 | 5.00 | 5.02 |

TABLE 8

Solubility Test results for Phosphate Polymorphic Form A

| Media | Target Conc. (mg/mL) | Measured Conc. (μg/mL) | Initial pH | pH value of supernatant |
|---|---|---|---|---|
| Purified water | 2 | 0.40 | 7.02 | 2.62 |
| pH 1.2 Hydrochloric Acid Buffer (50 mM) | | 22.88 | 1.17 | 0.99 |
| pH 3.0 citrate buffer (100 mM) | | 0.16 | 3.05 | 2.96 |
| pH 4.5 citrate buffer (100 mM) | | <LOQ | 4.44 | 4.41 |
| pH 7.4 PBS (50 mM) | | <LOQ | 7.40 | 7.09 |
| pH 9.0 USP Buffer (50 mM) | | <LOQ | 8.94 | 8.46 |
| SGF | | 3.85 | 1.80 | 1.67 |
| FaSSIF | | 7.14 | 6.51 | 6.09 |
| FeSSIF | | 50.68 | 5.00 | 4.94 |

LOQ: 0.1 μg/mL

Example 16

Intrinsic Dissolution Rate of Free Base Polymorphic Form A and Phosphate Polymorphic Form A About 100 mg of Free Base Polymorphic Form A or Phosphate Polymorphic Form A was weighed into the intrinsic dissolution apparatus and the sample compressed for 1 minute with a compression force of ~4 MPa to form a compacted pellet within the stainless-steel die. All loose powder was removed from the surface of the die. The intrinsic dissolution shaft was connected with the stainless-steel die and tightened so only one surface of the pellet was exposed (surface area=0.496 cm$^2$). The shaft in the spindle was adjusted to ensure the exposed surface of the compacted tablet was ~3.8 cm from the bottom of the vessel when lowered. The temperature of chamber water was set at 37° C.±0.5° C., the shaft rotation at 100 rpm and the sampling time points at 2, 5, 10, 15, 30, 45, 60, 120 min. SGF was used as dissolution medium (900 mL). At each time point, solution samples were filtered, and the supernatant was analyzed by HPLC-UV.

The intrinsic dissolution rate of Free Base Polymorphic Form A in SGF was $5 \times 10^{-5}$ mgcm$^2$ min$^{-1}$ (linear scope within 2 to 120 min). The intrinsic dissolution rate of Phosphate Polymorphic Form A in SGF was 0.184 mgcm$^2$ min$^{-1}$ (linear scope within 2 to 120 min).

Example 17

Pharmacokinetics Experiments with Phosphate Polymorphic Form A in Rats

To evaluate the pharmacokinetics (PK) of Phosphate Polymorphic Form A, suspensions or solutions were dosed by either oral gavage (0.5% methyl cellulose) or IV (60% PEG 400/40% saline) in normal, healthy, male Sprague-dawley rats with serial blood collection focused on the first 48 hours of exposure. Rats were dosed with vehicle or test compounds at 1 mg/kg (IV) or 2 mg/kg (PO). Approximately 0.2 mL blood was collected at each time point. All blood samples were collected jugular vein puncture. All blood samples were transferred into plastic microcentrifuge tubes containing 5 μL of EDTA-K$_2$ as anti-coagulant or pre-chilled commercial EDTA-K$_2$ tubes and placed on wet ice until centrifugation. Harvested blood samples were centrifuged within 30 min of collection at 7,000 rpm for 10 minutes. The extracts were analyzed for compound concentration by LC/MS/MS. Data were analyzed with Phoenix WinNonlin 6.3 using the IV-Noncompartmental model 201 (IV bolus input) and PO-Noncompartmental model 200 (extravascular input) methods.

TABLE 9

Results from Intravenously Administered Phosphate Polymorphic Form A

| PK Parameters | Mean IV |
|---|---|
| $T_{1/2}$ (h) | 12.4 |
| $Vd_{ss}$ (L/kg) | 1.49 |
| Cl (mL/min/kg) | 1.41 |
| $AUC_{0\text{-}last}$ (ng · h/mL) | 11260 |
| $AUC_{0\text{-}inf}$ (ng · h/mL) | 12097 |

TABLE 10

Results from Orally Administered Phosphate Polymorphic Form A

| PK Parameters | Mean PO |
|---|---|
| $C_{max}$ (ng/mL) | 794 |
| $T_{max}$ (h) | 7.00 |
| $T_{1/2}$ (h) | 11.1 |
| $AUC_{0-last}$ (ng · h/mL) | 14981 |
| $AUC_{0-inf}$ (ng · h/mL) | 15995 |
| $AUC_{Extra(\%)}$ | 6.25 |
| Bioavailability(%)[a] | 66.1 |

Example 18

Canine Pharmacokinetics Experiment with Phosphate Polymorphic Form A

To evaluate the pharmacokinetics (PK) Phosphate Polymorphic Form A, suspensions or solutions were dosed by either oral gavage (0.5% methyl cellulose) or IV (60% PEG400/40% saline) in normal, healthy, male Beagle dogs with serial blood collection focused on the first 48 hours of exposure. Dogs were dosed with vehicle or test compounds at 1 mg/kg (IV) or 2 mg/kg (PO). Approximately 0.5 mL blood was collected at each time point. All blood samples were collected from a peripheral vein. Blood was collected into commercially available tubes (Jiangsu Kangjian medical supplies co., LTD) containing Potassium ($K_2$) EDTA*$2H_2O$ and placed on wet ice until processed for plasma. Samples were centrifuged (3,000× g for 10 minutes at 2 to 8° C.) within one hour of collection. The extracts were analyzed for compound concentration by LC/MS/MS. Data were analyzed with Phoenix WinNonlin 6.3 using the IV-Noncompartmental model 201 (IV bolus input) and PO-Noncompartmental model 200 (extravascular input) methods.

TABLE 11

Results from Intravenously Administered Phosphate Polymorphic Form A

| PK Parameters | Mean IV |
|---|---|
| $T_{1/2}$ (h) | 12.8 |
| $Vd_{ss}$ (L/kg) | 1.93 |
| Cl (mL/min/kg) | 2.52 |
| $AUC_{0-last}$ (ng · h/mL) | 7846 |
| $AUC_{0-inf}$ (ng · h/mL) | 9167 |

TABLE 12 from Intravenously Administered Phosphate Polymorphic Form A

| PK Parameters | Mean PO |
|---|---|
| $C_{max}$ (ng/mL) | 649 |
| $T_{max}$ (h) | 3.33 |
| $T_{1/2}$ (h) | 12.2 |
| $AUC_{0-last}$ (ng · h/mL) | 11725 |
| $AUC_{0-inf}$ (ng · h/mL) | 13943 |
| Bioavailability(%) | 74.7 |

The bioavailability of Phosphate Polymorphic Form A is over 3 times higher than the previously reported bioavailability of TPA023B in canines. This is highly adventitious for therapeutics meant to treat dogs, and significantly reduces the quantities of active pharmaceutical ingredient that need to be prepared for the completion of GLP toxicology studies.

Example 19

Preparation of Polymorphic Forms of TPA023B salts or Co-Crystals

TPA023B and a pharmaceutically acceptable acid, and/or a previously prepared TPA023B salt or co-crystal, are combined and stirred for a period of time in one or more solvents, with or without heating and/or cooling steps; and/or are dissolved in a one or more solvents with or without heating and then some or all of the solvent(s) are removed; and/or are dissolved in one or more solvents the an anti-solvent, or combination of antisolvents, or a mixture of solvent and antisolvent are added; any other method known to one skilled in the art; and combinations of any or all of the above processes.

Example 20

Preparation of Polymorphic Forms of TPA023B Free Base

TPA023B is slurried for a period of time in one or more solvents, with or without heating; and/or dissolved in a one or more solvents with or without heating and then some or all of the solvent(s) are removed through a method such as evaporation or distillation; and/or dissolved in one or more solvents and an anti-solvent, combination of antisolvents, or a mixture of solvent and antisolvent is added; and/or dissolved in one or more solvents with or without heating and then allowing the solution is cooled, or actively cooled; and/or is heating in the absence of solvent; and/or is heated under atmospheric or reduced pressure until it sublimates and is collected on a cooled surface; and/or is melted and allowed it to cool; and/or is exposed to water vapor or the vapor of an solvent with or without heating; and/or any other method known to one skilled in the art; and by using combinations of any or all of the above processes.

Example 21

HPLC Protocols

Table 13 provides an exemplary set of parameters and conditions used in HPLC.

TABLE 13

HPLC conditions and parameters

| | |
|---|---|
| Column: | Waters, Symmetry C18, 4.6* 150 mm 3.5-Micron |
| Column Temperature: | 40° C. |
| Flow rate: | 1 mL/min |
| Detection: | 266 nm |
| Injection volume: | 10.0 µL |
| Run time: | 20 minutes |
| Diluent | 50/50 ACN/$H_2O$ |
| Mobile Phase A: | 0.1% TFA in water |
| Mobile Phase B: | ACN |

TABLE 13-continued

| | HPLC conditions and parameters | | |
|---|---|---|---|
| | Time (min) | Mobile Phase A % | Mobile Phase B % |
| Gradient program | 0.0 | 80 | 20 |
| | 15 | 10 | 90 |
| | 15.1 | 80 | 20 |
| | 20 | 10 | 20 |

Example 22

Purity Test

Appropriately 2 mg of compounds were accurately weighed into a glass vial, then added diluents (ACN/water, 50/50) and sonicated for 2 minutes to dilute the target concentration of 0.2 mg/mL. The solution was equilibrated to room temperature and then the purity of the compounds was determined by HPLC.

Example 23 pKa Measurement 10 mg of TPA023B was used for the pKa measurement.
Solution Preparation:

ISA Water (Ionic Strength Adjusted Water, 0.15 M KCl): Accurately weigh 5.591 g KCl into a 500 mL volumetric flask, dissolve the sample with water, add to volume and mix well. Cosolvent of 60% (v/v) DMSO: Dissolve 2.795 g potassium chloride in 100 mL distilled or deionised water and make up to 250 mL with analytical grade DMSO (Ionic strength adjusted DMSO solution).

Cosolvent of 80% (v/v) MeOH: Dissolve 2.795 g potassium chloride in 50 mL distilled or deionized water and make up to 250 mL with analytical grade MeOH (Ionic strength adjusted MeOH solution).

pKa Determination by pH Metric Method (With or Without Co-Solvent):

About 1 mg of sample was weighed into a sample vial, about 1.5 mL of ISA water or 1.5 mL of co-solvent (80% MeOH or 60% DMSO) was added into the vial automatically. The sample solution pre-acidified to pH 2.0 with 0.5 M HCl by the instrument automatically, then titrated three times with base to get pKa value from pH 2 to pH 12, and then extrapolated to get aqueous pKa value. Using this method, the pKa of TPA023B was determined to be 2.19.

Example 24

Approximate Solubility Study of TPA023B in Organic Solvents

About 25 mg of compound (TPA023B) was added to a 2.0 mL vial containing 0.5 mL of each organic solvent in Table 14, which was then sealed. The mixtures were stirred-mixed at 800 rpm, RT (25° C.) for 4 hours. After that, if the compound was not completely dissolved in the solvent, the mixture was then stirred-mixed at 800 rpm, 50° C. overnight. If the final mixture was clear solution, the solution would be evaporated by vacuum drying oven at 35° C. and the resulted solid would be checked by XRPD. If the final mixture was slurry, the slurry would be centrifuged at 14000 rpm for 5 minutes and then the residues would be dried by vacuum drying oven at 35° C. and checked by XRPD.

Figure 27:
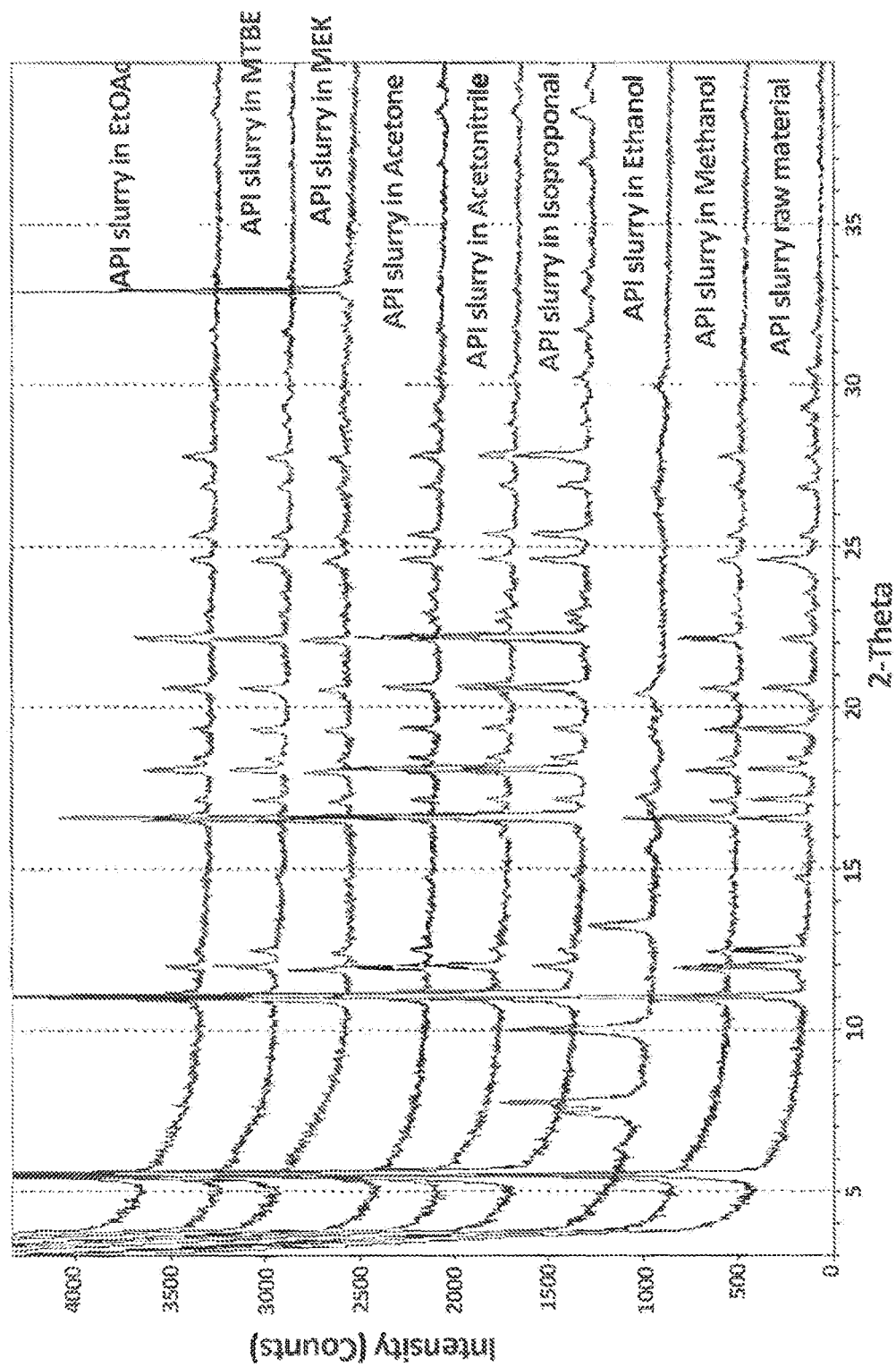
FIG. 27 illustrates an XRPD profile overlay of TPA023B slurry in solvents (I)
Figure 28:
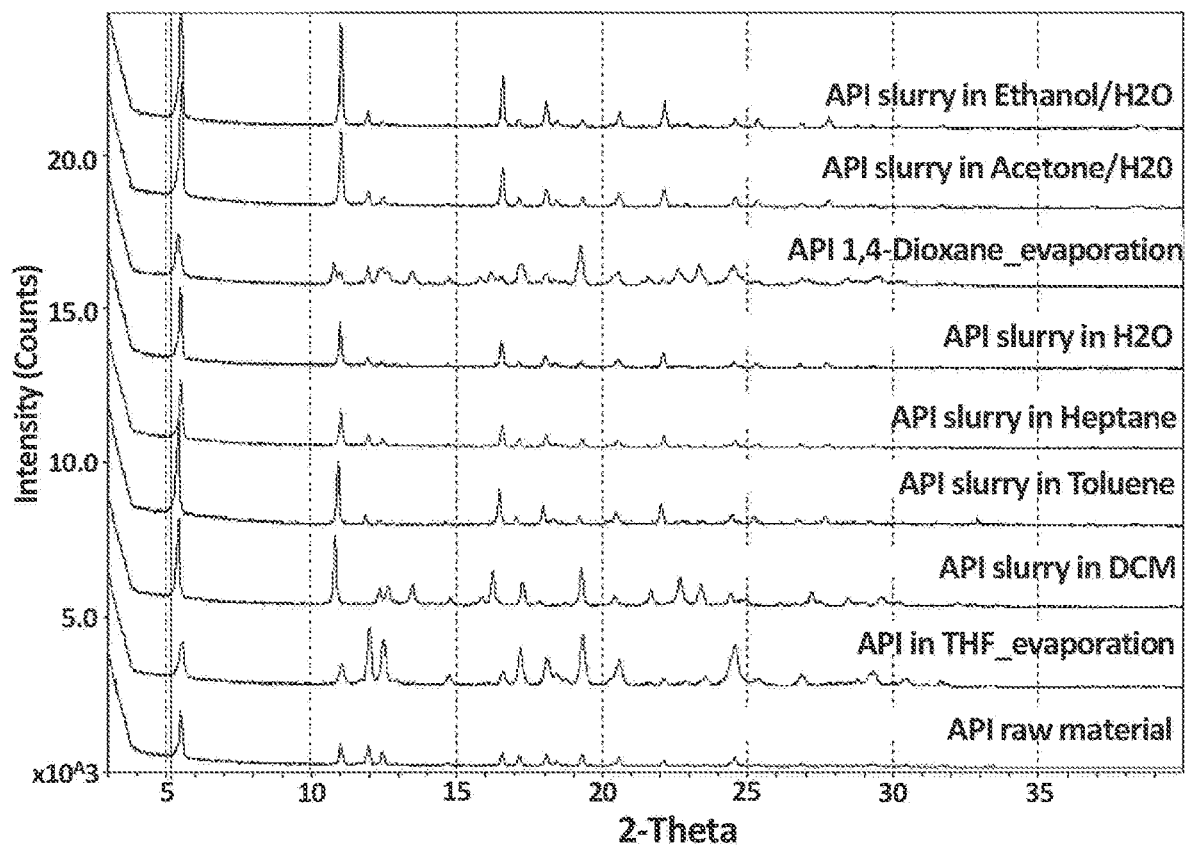
FIG. 28 illustrates an XRPD profile overlay of TPA023B slurry in solvents (II)
Figure 29:
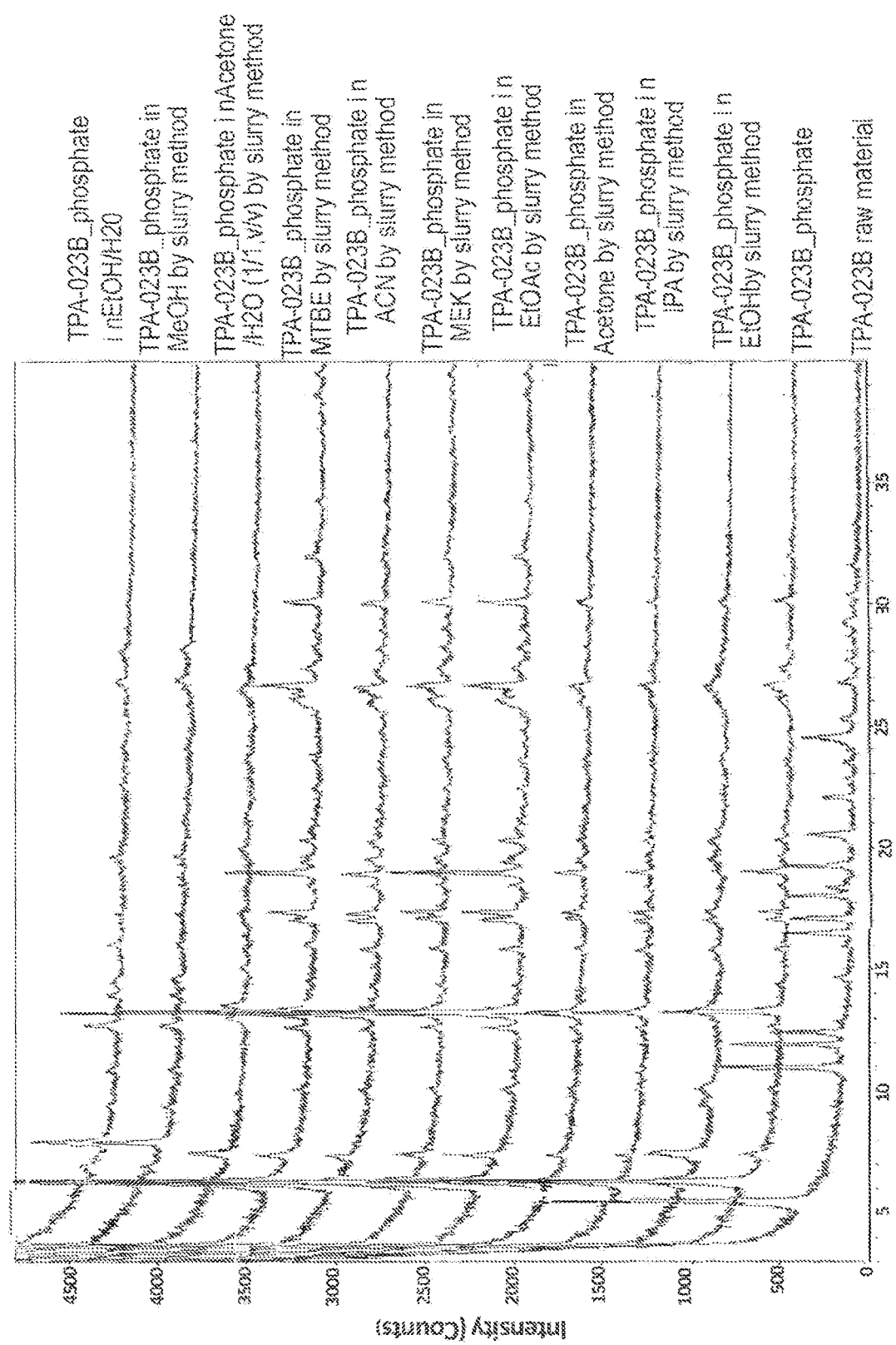
FIG. 29 illustrates XRPD patterns of TPA023B phosphate solids obtained by polymorph screening using the slurry method

The form of TPA023B raw material was named as "Free-base Form A" and its corresponding XRPD pattern as "Pattern A." The characterization of solubility-test samples of TPA023B is provided in Table 15. The corresponding XRPD profile overlays of TPA023B slurry in solvents are provided in FIG. 27 and FIG. 28.

TABLE 14

Approximate Solubility Results of TPA023B in Solvents

| | Solubility (mg/mL) | | | Solubility (mg/mL) | |
|---|---|---|---|---|---|
| Solvent | RT | 50° C. | Solvent | RT | 50° C. |
| Methanol | N/A | <50 | DMF | >50 | N/A |
| Ethanol | N/A | <50 | DMSO | >50 | N/A |
| Isopropanol | N/A | <50 | DCM | N/A | <50 |
| Acetonitrile (ACN) | N/A | <50 | Toluene | N/A | <50 |
| Acetone | N/A | <50 | Heptane | N/A | <50 |
| MEK | N/A | <50 | $H_2O$ | N/A | <50 |
| MTBE | N/A | <50 | 1,4-Dioxane | <50 | >50 |
| EtOAc | N/A | <50 | EtOH/$H_2O$ (1/1, v/v) | N/A | <50 |
| THF | <50 | >50 | Acetone/$H_2O$ (1/1, v/v) | N/A | <50 |

TABLE 15

Characterization of Solubility-Test Samples of TPA023B

| Solvent | Target conc. (mg/ml) | Visual Observation RT | Visual Observation 50° C. | Drying method and appearance | XRPD Results |
|---|---|---|---|---|---|
| Methanol | 50 | N/A | Slurry | Centrifugation/ Yellow powder | Pattern a |
| Ethanol | | N/A | Slurry | Centrifugation/ Yellow powder | Pattern b |
| Isopropanol | | N/A | Slurry | Centrifugation/ Yellow powder | Pattern a |
| Acetonitrile | | N/A | Slurry | Centrifugation/ Yellow powder | Pattern a |
| Acetone | | N/A | Slurry | Centrifugation/ Yellow powder | Pattern a |
| MEK | | N/A | Slurry | Centrifugation/ Yellow powder | Similar to Pattern a |
| MTBE | | N/A | Slurry | Centrifugation/ Yellow powder | Pattern a |
| EtOAc | | N/A | Slurry | Centrifugation/ Yellow powder | Pattern a |
| THF | | N/A | Clear | Evaporation/ Yellow powder | Pattern a |

TABLE 15-continued

Characterization of Solubility-Test Samples of TPA023B

| Solvent | Target conc. (mg/ml) | Visual Observation RT | Visual Observation 50° C. | Drying method and appearance | XRPD Results |
|---|---|---|---|---|---|
| DCM | | N/A | Slurry | Centrifugation/ Yellow powder | Pattern c |
| DMSO | | Clear | N/A | Evaporation/ Yellow powder | N/A |
| DMF | | Clear | N/A | Evaporation/ Yellow powder | N/A |
| Toluene | | N/A | Slurry | Centrifugation/ Yellow powder | Pattern a |
| Heptane | | N/A | Slurry | Centrifugation/ Yellow powder | Pattern a |
| H$_2$O | | N/A | Slurry | Centrifugation/ Yellow powder | Pattern a |
| 1,4-Dioxane | | N/A | Clear | Centrifugation/ Yellow powder | Pattern d |
| EtOH/H$_2$O (1/1, v/v) | | N/A | Slurry | Centrifugation/ Yellow powder | Pattern a |
| Acetone/H$_2$O (1/1, v/v) | | N/A | Slurry | Centrifugation/ Yellow powder | Pattern a |

Example 25

Approximate Solubility Study of TPA023B Phosphate

Approximate 2 mg of TPA023B Phosphate Form A was weighed out into each 1.5 mL vial, and then solvent was added stepwise under stirring until no particles could be visually observed. The total amount of solvent was recorded to calculate the approximate solubility in these solvents. The solubility results are shown in Table 16. TPA023B phosphate showed relatively high solubility in DMF and DMSO.

TABLE 16

Approximate Solubility Results of TPA023B Phosphate in Solvents

| Solvent | Solubility (mg/mL) RT | Solubility (mg/mL) 50° C. | Solvent | Solubility (mg/mL) RT | Solubility (mg/mL) 50° C. |
|---|---|---|---|---|---|
| Methanol | 8-10 | 10-50 | DMF | >100 | N/A |
| Ethanol | <8 | 10-50 | DMSO | >100 | N/A |
| Isopropanol | <8 | 10-50 | DCM | 8-10 | 10-50 |
| Acetonitrile (ACN) | <2 | 2-10 | Toluene | <2 | <2 |
| Acetone | 6-10 | <10 | Heptane | <2 | <2 |
| MEK | 2-4 | <10 | H$_2$O | <2 | <2 |
| MTBE | <2 | <2 | 1,4-Dioxane | 20-25 | 20-25 |
| EtOAc | <2 | <2 | EtOH/H$_2$O (1/1, v/v) | <2 | <2 |
| THF | 20-50 | <50 | Acetone/H$_2$O (1/1, v/v) | <2 | 2-10 |

Example 26

Polymorph Screening of TPA023B Phosphate by Slurry Method

TPA023B phosphate (about 20 mg) was added in appropriate various solvents, respectively. The suspension was stirred at 500 rpm for 3 days at RT. The residues of the compound (TPA023B phosphate) were separated by centrifuge (5 min at 14000 rpm) and further dried overnight in the vacuum oven at 30° C. The dried solid was analyzed by XRPD. If XRPD was changed, the dried solids were then analyzed by PLM, DSC and TGA. Table 17 illustrates the results of the slurry screening methods using selected solvents. For example, when the form of TPA023B phosphate is named as "Form A," then its corresponding XRPD pattern is designated as "Pattern A."

TABLE 17

Polymorph Screening of TPA023B Phosphate by Slurry Method

| Solvent | TPA023B_phosphate weight (mg) | Solvent Volume (μL) | Appearance | XRPD pattern |
|---|---|---|---|---|
| Methanol | 20.88 | 200 | Yellow powder | Pattern B |
| Ethanol | 20.25 | 200 | Yellow powder | Pattern A |
| Isopropanol | 20.49 | 200 | Yellow powder | Pattern A |
| Acetone | 20.10 | 200 | Yellow powder | Pattern A |
| EtOAc | 19.98 | 200 | Yellow powder | Pattern A |
| MEK | 20.40 | 200 | Yellow powder | Pattern A |
| ACN | 20.70 | 200 | Yellow powder | Pattern A |
| Methyl tert-butyl ether (MTBE) | 19.95 | 200 | Yellow powder | Pattern A |
| EtOH/H$_2$O (1/1, v/v) | 20.57 | 200 | Yellow powder | Pattern B |
| Acetone/H$_2$O (1/1, v/v) | 20.45 | 200 | Yellow powder | Pattern A |

Example 27

Polymorph Screening of TPA023B Phosphate by Heat-Cooling Method

TPA023B phosphate (about 20 mg) was weighed and transferred into a vial containing of 2000, of each selected solvent. The suspension was stirred at 700 rpm for 4 hours at 60° C., and the suspension was allowed to cool to room temperature. This cycle was repeated twice. Any resulting solids were collected by centrifugation and dried in a 30° C. vacuum oven. The samples were analyzed by XRPD. If XRPD pattern differed, the samples were analyzed by PLM, DSC and TGA. In addition to TPA023B Phosphate Pattern A, Free Base Pattern C and Phosphate pattern D were observed, as shown in Table 18 and FIG. 30.

Figure 31:
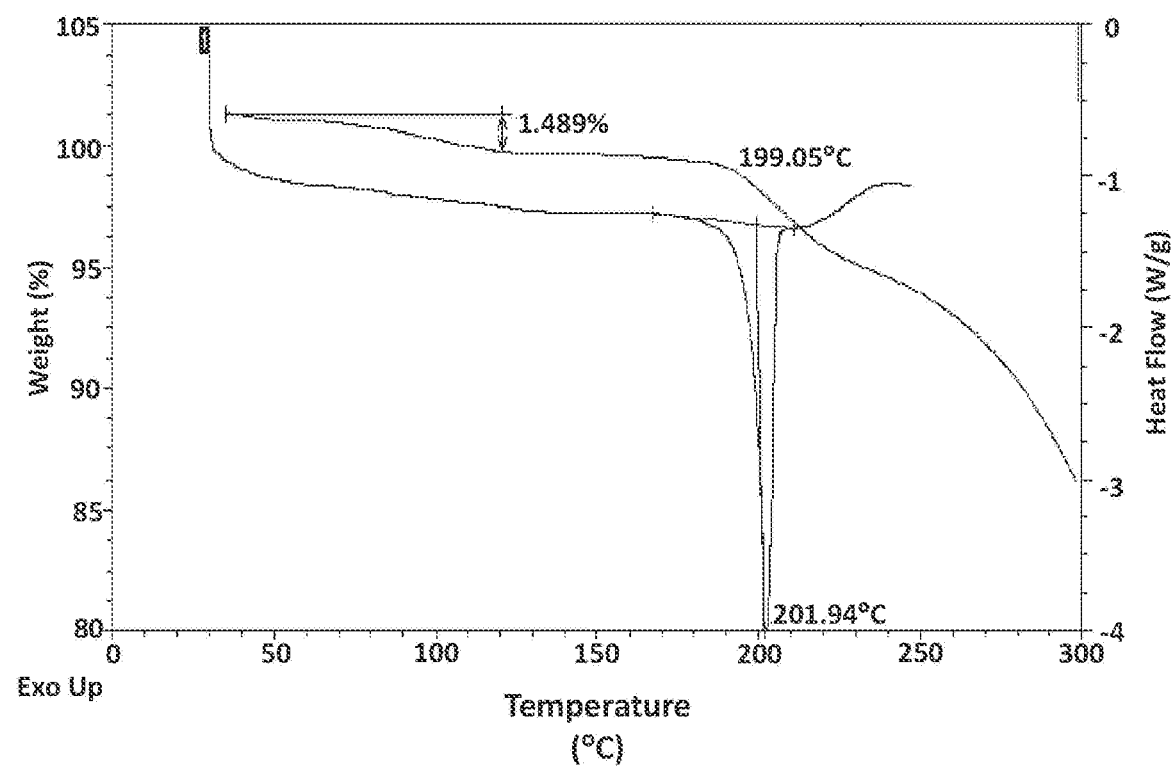
FIG. 31 illustrates a DSC/TGA thermogram for TPA023B phosphate Pattern D

A DSC/TGA thermogram of TPA023B Phosphate Polymorphic Pattern D is illustrated in FIG. 31. As shown in FIG. 31, the DSC trace showed a single endothermic peak with an onset temperature of 199° C. (95.92 J/g) and the TGA result showed that the original form exhibits a three-step weight loss of 1.489% from 30° C. to 150° C., which could be attributed to removal of residual solvent.

TABLE 18

Polymorph Screening of TPA023B Phosphate by Heat-Cooling Method

| Solvent | TPA023B_phosphate weight (mg) | Solvent Volume (μL) | Appearance | XRPD pattern |
|---|---|---|---|---|
| Methanol | 20.08 | 200 | Yellow powder | Free Base Form C |
| Ethanol | 20.03 | 200 | Yellow powder | Phosphate Pattern A |
| Isopropanol | 20.71 | 200 | Yellow powder | Pattern D *(a mixture comprising Free Base Form C and Phosphate Form A) |
| THF | 20.77 | 200 | Yellow powder | Phosphate Pattern A |
| 1,4-Dioxane | 20.00 | 200 | Yellow powder | Phosphate Pattern A |
| DCM | 20.00 | 200 | Yellow powder | Phosphate Pattern A |
| ACN | 20.20 | 200 | Yellow powder | Phosphate Pattern A |
| Acetone/H$_2$O (1/1, v/v) | 20.40 | 200 | Yellow powder | Phosphate Pattern D (a mixture comprising Free Base Form C and Phosphate Form A) |

* Free Base Form C is obtained in a scale-up method, see example 29.

Example 28

Polymorph Screening of TPA023B Phosphate by Anti-Solvent Method

Figure 32:
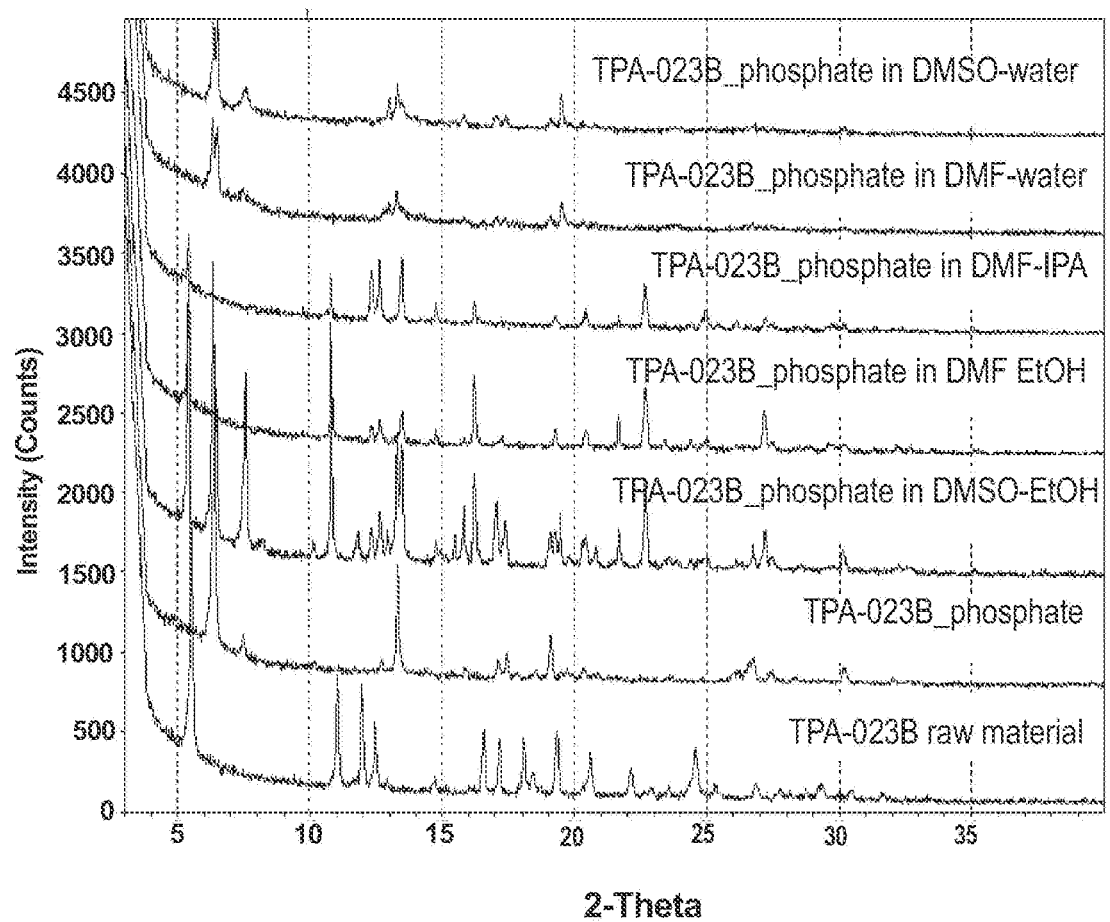
FIG. 32 illustrates XRPD patterns of TPA023B phosphate solids obtained by polymorph screening using the anti-solvent method

TPA023B phosphate (about 150 mg) was dissolved in 1.5 mL of either DMSO or DMF to prepare stock solutions (100 mg/mL). Anti-solvent was added until either precipitation occurred, or the amount of anti-solvent added reached 5× of the amount of solvent. The precipitate was collected by centrifuge and dried overnight in a 30° C. vacuum oven. The obtained samples were analyzed by XRPD. If the XRPD pattern changed, the dried solids were analyzed by PLM, DSC and TGA. As shown in Table 19 and FIG. 32, TPA023B Free Base Form C and TPA023B Phosphate Pattern E (a mixture comprising Phosphate Form A) were observed.

TABLE 19

Polymorph Screening of TPA023B Phosphate by Anti-solvent Method

| Stock Solution | Anti-Solvent | Anti-Solvent Volume (mL) | Observation | XRPD pattern |
|---|---|---|---|---|
| 100 mg/mL of TPA023B phosphate in DMF (200 μL of stock solution for each anti-solvent) | ACN | 1.0 | Clear solution | N/A |
| | Ethanol | 1.0 | Precipitate after stored in 5° C. freezer overnight | Free Base Form C |
| | Isopropanol | 1.0 | precipitate immediately | Free Base Form C |
| | Acetone | 1.0 | Clear solution | N/A |
| | Water | 1.0 | Precipitate immediately | Pattern E (a mixture comprising Phosphate Form A) |
| | EtOAc | 1.0 | Clear solution | N/A |

TABLE 19-continued

Polymorph Screening of TPA023B Phosphate by Anti-solvent Method

| Stock Solution | Anti-Solvent | Anti-Solvent Volume (mL) | Observation | XRPD pattern |
|---|---|---|---|---|
| 100 mg/mL of TPA023B phosphate in DMSO (300 µL of stock solution for each anti-solvent) | ACN | 1.5 | Clear solution | N/A |
| | Ethanol | 1.5 | Precipitate after stored in 5° C. freezer overnight | Pattern D (a mixture comprising Free Base Form C and Phosphate Form A) |
| | Isopropanol | 1.5 | Clear solution | N/A |
| | Acetone | 1.5 | Clear solution | N/A |
| | Water | 1.5 | Precipitate immediately | Pattern E (a mixture comprising Phosphate Form A) |
| | EtOAc | 1.5 | Clear solution | N/A |

Example 29

Scale-Up of Polymorph Screening of TPA023B Phosphate by Heat-Cooling Method

Figure 33:
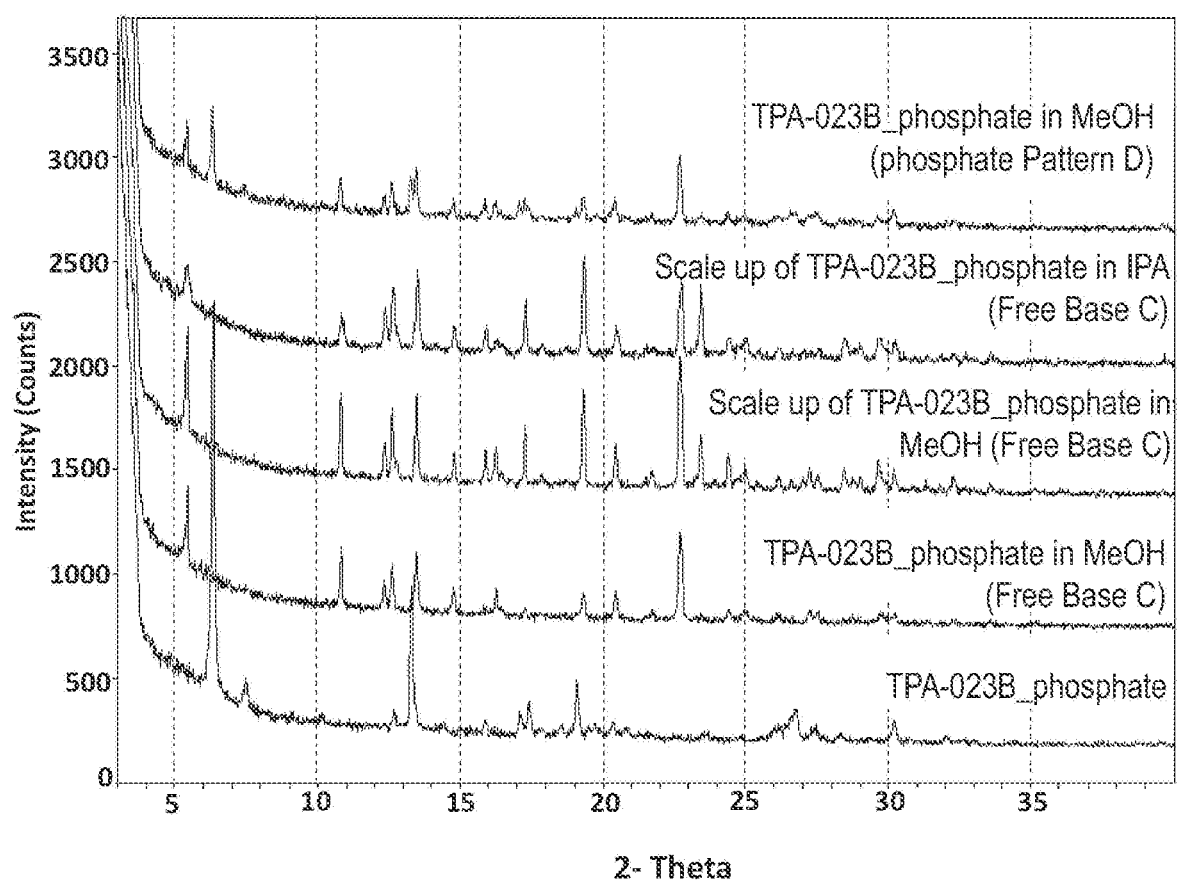
FIG. 33 illustrates additional XRPD patterns of TPA23B Polymorph screening by heat-cooling method

TPA023B phosphate (about 100 mg) was used in a scaled-up repeat of the experiments in Example 27 with solvents methanol and isopropanol, respectively. The solids obtained using methanol exhibited an XRPD pattern of Free Base Form C, the same pattern as shown in example 27. The solids obtained using isopropanol (IPA) also exhibited an XRPD pattern of Free Base Form C in the scale-up. The XRPD patterns of the obtained solids are illustrated in FIG. 33. The yield of the scale-up experiments is shown in Table 20.

Figure 34:
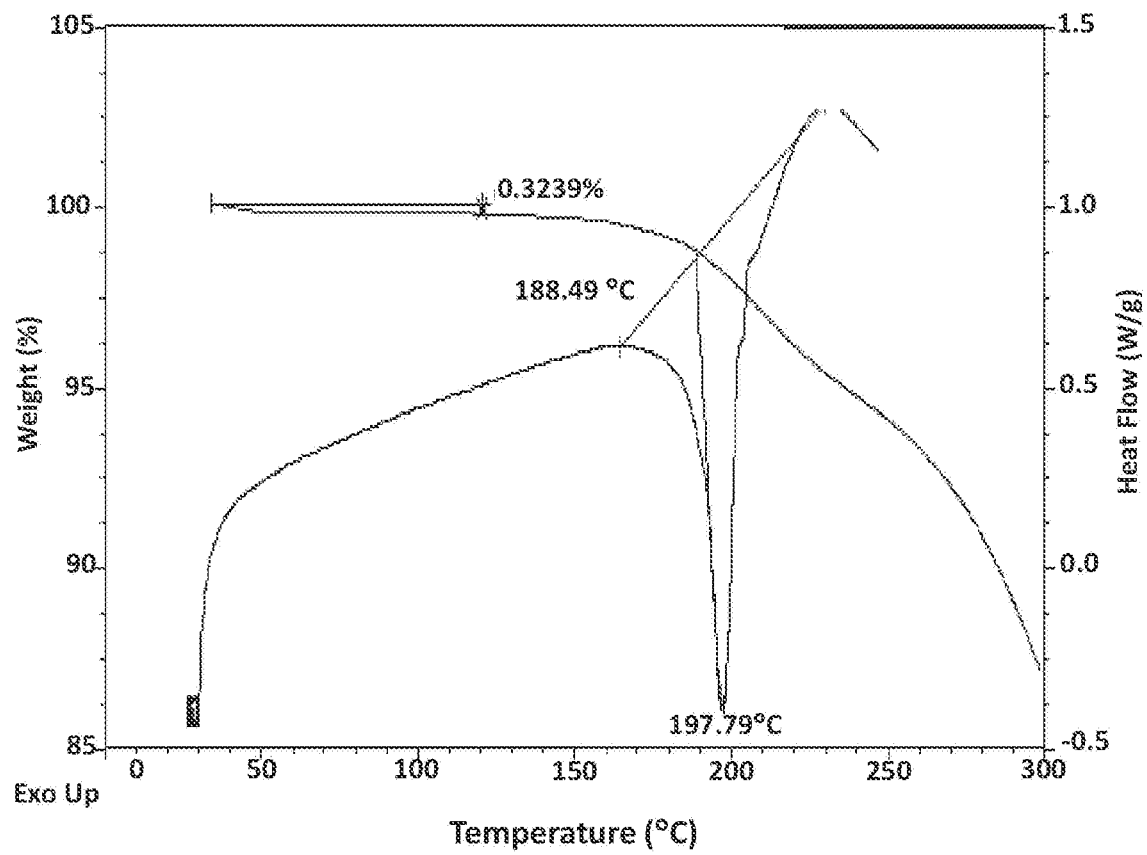
FIG. 34 illustrates an additional DSC/TGA thermogram of TPA023B Polymorph screening in IPA by the heat-cooling method

As shown in FIG. 34, the DSC/TGA thermogram of the product produced in IPA by the heat-cooling method showed one endothermic peak with an onset temperature of 188° C. (112.9 J/g) by DSC. Its TGA trace showed a three-step weight loss of 0.32% from 30° C. to 120° C., which could be attributed to removal of residual solvent.

TABLE 20

Yield of scale-up of TPA023B phosphate with Heat-cooling method

| TPA023B_phosphate weight (mg) | Solvent | Solvent Volume (mL) | Product amount (mg) | Yield (%) |
|---|---|---|---|---|
| 100.39 | MeOH | 1.0 | 62.07 | 61.83 |
| 100.53 | IPA | 1.0 | 73.32 | 72.93 |

What is claimed is:

1. A crystalline salt or co-crystal of 2',6-difluoro-5'-[3-(1-hydroxy-1-methylethyl)imidazo[1,2-b][1,2,4]triazin-7-yl]biphenyl-2-carbonitrile with p-toluenesulfonic acid of the following formula:

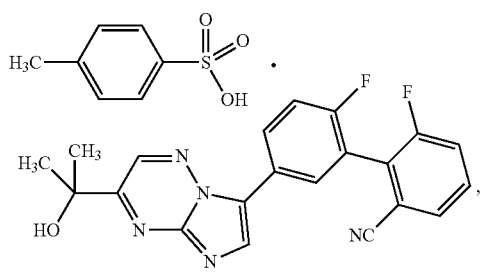

wherein the crystalline salt or co-crystal is Form A; and wherein the crystalline salt or co-crystal is characterized by an X-ray powder diffraction pattern comprising at least three characteristic peaks at angles (°2θ) selected from 7.0°±0.2 °2θ, 12.4°±0.2 °2θ, 12.6°±0.2 °2θ, 13.0°±0.2 °2θ, 14.1°±0.2 °2θ, 15.4°±0.2 °2θ, 15.7°±0.2 °2θ, 16.3°±0.2 °2θ, 17.5°±0.2 °2θ, 18.3°±0.2 °2θ, 19.0°±0.2 °2θ, 21.0°±0.2 °2θ, 22.3°±0.2 °2θ, 23.0°±0.2 °2θ, and 24.9°±0.2 °2θ, when measured using the parameters described in Table 1.

2. The crystalline salt or co-crystal of claim 1, wherein the crystalline salt or co-crystal is further characterized by an X-ray powder diffraction pattern comprising at least six characteristic peaks at angles (° 2θ) selected from 7.0°±0.2 °2θ, 12.4°±0.2 °2θ, 12.6°±0.2 °2θ, 13.0°±0.2 °2θ, 14.1°±0.2 °2θ, 15.4°±0.2 °2θ, 15.7°±0.2 °2θ, 16.3°±0.2 °2θ, 17.5°±0.2 °2θ, 18.3°±0.2 °2θ, 19.0°±0.2 °2θ, 21.0°±0.2 °2θ, 22.3°±0.2 °2θ, 23.0°±0.2 °2θ, and 24.9°±0.2 °2θ.

3. The crystalline salt or co-crystal of claim 1, wherein the crystalline salt or co-crystal is further characterized by an X-ray powder diffraction pattern comprising at least nine characteristic peaks at angles (°2θ) selected from 7.0°±0.2 °2θ, 12.4°±0.2 °2θ, 12.6°±0.2 °2θ, 13.0°±0.2 °2θ, 14.1°±0.2 °2θ, 15.4°±0.2 °2θ, 15.7°±0.2 °2θ, 16.3°±0.2 °2θ, 17.5°±0.2 °2θ, 18.3°±0.2 °2θ, 19.0°±0.2 °2θ, 21.0°±0.2 °2θ, 22.3°±0.2 °2θ, 23.0°±0.2 °2θ, and 24.9°±0.2 °2θ.

4. The crystalline salt or co-crystal of claim 1, wherein the crystalline salt or co-crystal is further characterized by an X-ray powder diffraction pattern comprising at least twelve characteristic peaks at angles (°2θ) selected from 7.0°±0.2 °2θ, 12.4°±0.2 °2θ, 12.6°±0.2 °2θ, 13.0°±0.2 °2θ, 14.1°±0.2 °2θ, 15.4°±0.2 °2θ, 15.7°±0.2 °2θ, 16.3°±0.2 °2θ, 17.5°±0.2 °2θ, 18.3°±0.2 °2θ, 19.0°±0.2 °2θ, 21.0°±0.2 °2θ, 22.3°±0.2 °2θ, 23.0°±0.2 °2θ, and 24.9°±0.2 °2θ.

5. The crystalline salt or co-crystal of claim 1, wherein the crystalline salt or co-crystal is further characterized by an X-ray powder diffraction pattern comprising peaks at angles (°2θ) of 7.0°±0.2 °2θ, 12.4°±0.2 °2θ, 12.6°±0.2 °2θ, 13.0°±0.2 °2θ, 14.1°±0.2 °2θ, 15.4°±0.2 °2θ, 15.7°±0.2 °2θ, 16.3°±0.2 °2θ, 17.5°±0.2 °2θ, 18.3°±0.2 °2θ, 19.0°±0.2 °2θ, 21.0°±0.2 °2θ, 22.3°±0.2 °2θ, 23.0°±0.2 °2θ, and 24.9°±0.2 °2θ.

Figure 17A:
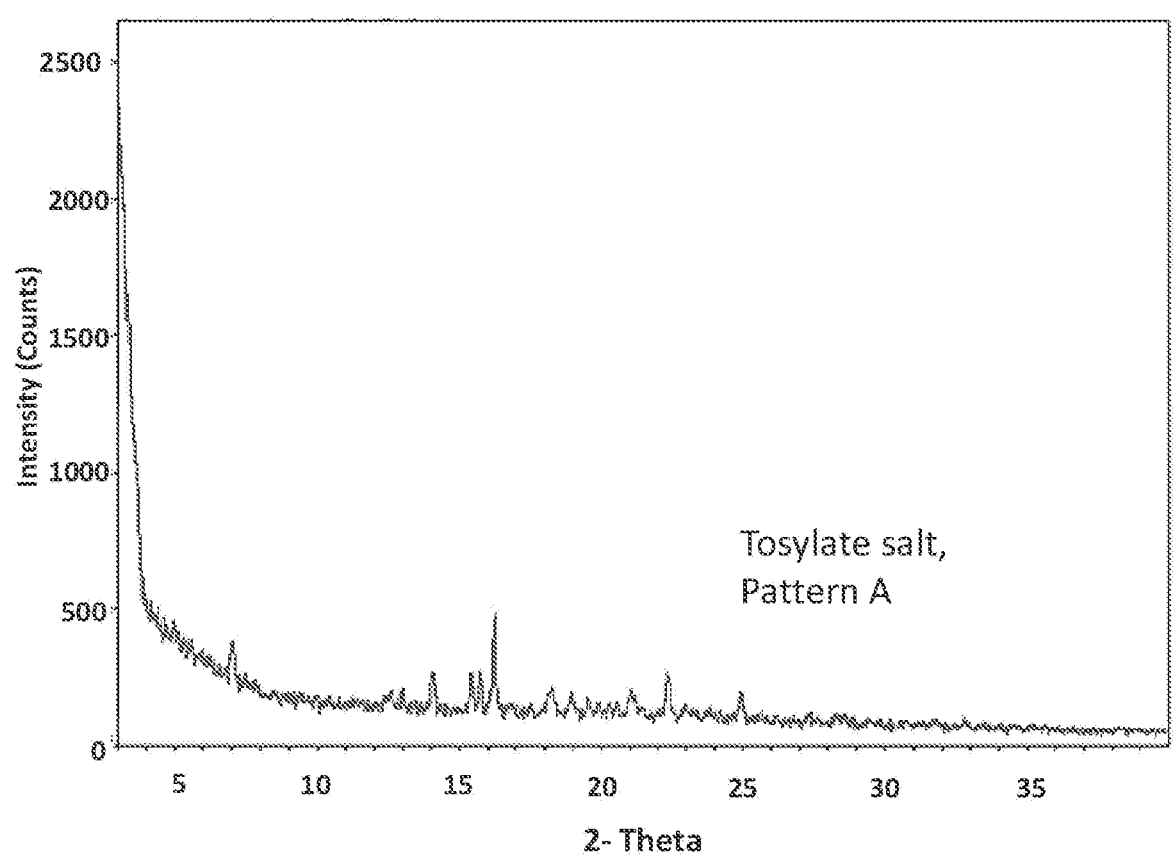
Figure 17B:
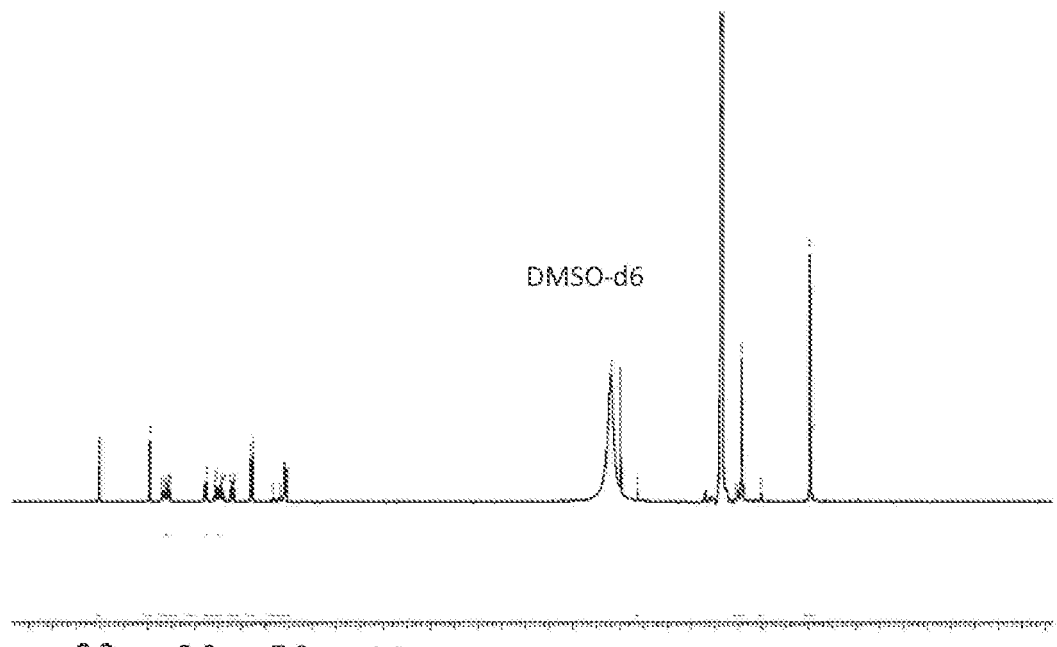

6. The crystalline salt or co-crystal of claim 1, wherein the crystalline salt or co-crystal is further characterized by an X-ray powder diffraction pattern as shown in FIG. 17A.

7. The crystalline salt or co-crystal of claim 1, wherein the crystalline salt or co-crystal is further characterized by a differential scanning calorimetry (DSC) thermogram comprising an endothermic peak at 170° C.

Figure 18:
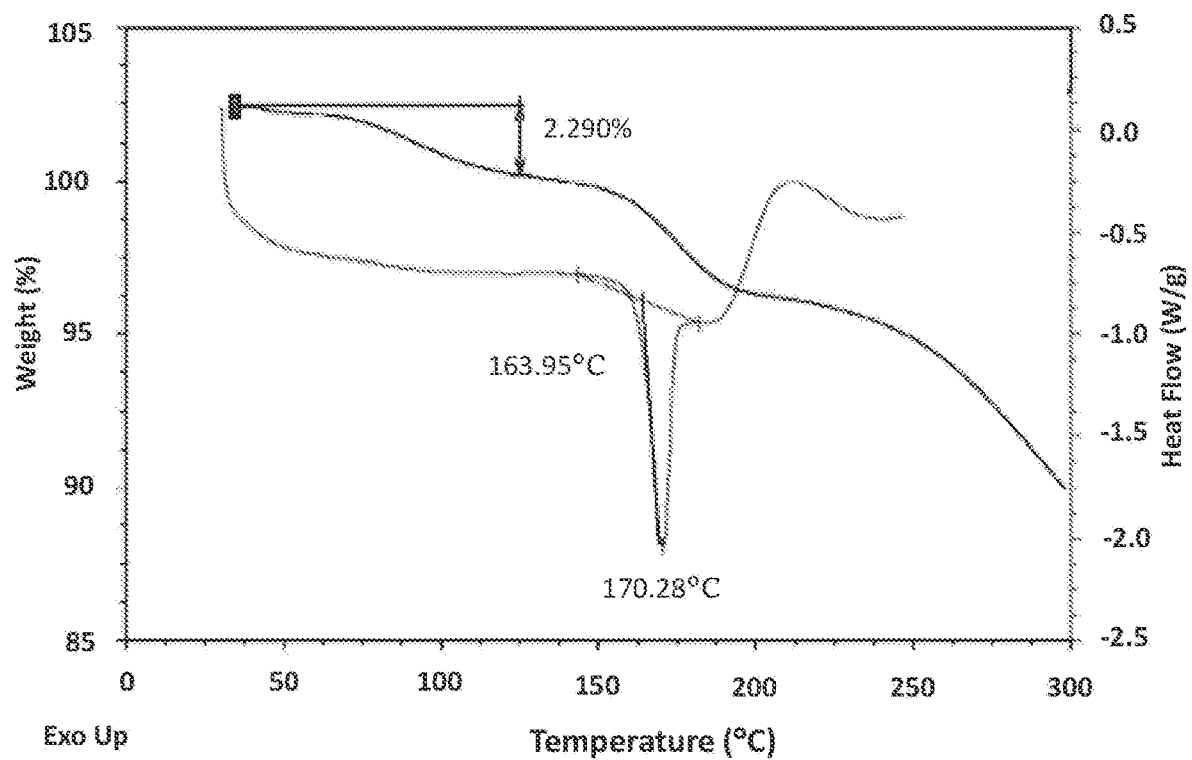
FIG. 18 illustrates a DSC/TGA thermogram for TPA023B tosylate Form A

8. The crystalline salt or co-crystal of claim 1, wherein the crystalline salt or co-crystal is further characterized by a differential scanning calorimetry (DSC) thermogram as shown in FIG. 18.

9. A therapeutic or prophylactic composition comprising the crystalline salt or co-crystal of claim 1.

10. A method for modulating α2/α3 γ-aminobutyric acid type A (GABAA) receptor activity in a subject in need thereof, wherein the method comprises administering to the subject a therapeutically effective amount of the crystalline salt or co-crystal of claim 1.

11. The method of claim 10, wherein the subject has a condition or disorder associated with α2/α3 γ-aminobutyric acid type A (GABAA) receptor selected from the group consisting of alcohol dependence, anxiety, autism, a cognitive impairment, depression, drug addiction, epilepsy, an itch, a muscle spasm, pain, panic disorder, pruritis, and schizophrenia.

12. The method of claim 11, wherein the condition or disorder associated with α2/α3 γ-aminobutyric acid type A (GABAA) receptor is anxiety.

13. The method of claim 12, wherein the anxiety is generalized anxiety disorder.

14. The method of claim 11, wherein the condition or disorder associated with α2/α3 γ-aminobutyric acid type A (GABAA) receptor is autism.

15. The method of claim 14, wherein the autism is selected from the group consisting of an autism related to ion-channel dysfunction, an autism resulting from SCN2a mutation, and fragile X syndrome.

16. The method of claim 12, wherein the condition or disorder associated with α2/α3 γ-aminobutyric acid type A (GABAA) receptor is epilepsy.

17. The method of claim 16, wherein the epilepsy is selected from the group consisting of a benign epilepsy with a centrotemporal spike, a benign familial neonatal infantile seizure, childhood absence epilepsy (CEA), cortical dysplasia-focal epilepsy syndrome, Doose syndrome, Dravet syndrome, early myoclonic encephalopathy, an epilepsy with a continuous spike and wave during slow wave sleep, febrile seizure plus, focal epilepsy, generalized epilepsy, juvenile absence epilepsy, juvenile myoclonic epilepsy (JME), Landau-Kleffner syndrome, Lennox-Gastaut syndrome (LGS), a malignant migrating partial seizure of infancy, myoclonic atonic epilepsy, a nerve agent induced seizure, Ohtahara syndrome, partial epilepsy, Rasmussen's syndrome, staticus epilepticus, sunflower syndrome, traumatic brain injury, a tremor from alcohol withdrawal, tuberous sclerosis complex, and West syndrome.

18. The method of claim 11, wherein the condition or disorder associated with α2/α3 γ-aminobutyric acid type A (GABAA) receptor is an itch.

19. The method of claim 18, wherein the itch is selected from the group consisting of aquagenic itch, atopic dermatitis, chronic itch, neurodermatitis, neurogenic itch, notalgia paresthetica, prurigo nodularis, psoriasis, uremic pruritis, and psychogenic itch.

20. The method of claim 11, wherein the condition or disorder associated with α2/α3 γ-aminobutyric acid type A (GABAA) receptor is pain.

21. The method of claim 20, wherein the pain is selected from the group consisting of burn pain, chemotherapy induced pain, fibromyalgia, human immunodeficiency virus (HIV) associated neuropathy, inflammatory pain, musculoskeletal pain, neuropathic pain, osteoarthritis, phantom limb pain, peripheral diabetic neuropathy, post-herpetic neuralgia, post-operative pain, and rheumatoid arthritis.

\* \* \* \* \*